US012747221B2

(12) United States Patent
Liotta et al.

(10) Patent No.: US 12,747,221 B2
(45) Date of Patent: *Sep. 29, 2026

(54) GLUN2B-SUBUNIT SELECTIVE ANTAGONISTS OF THE N-METHYL-D-ASPARTATE RECEPTORS WITH ENHANCED POTENCY AT ACIDIC PH

(71) Applicants: Emory University, Atlanta, GA (US); Neurop, Inc., Atlanta, GA (US)

(72) Inventors: Dennis Liotta, Atlanta, GA (US); Stephen Traynelis, Atlanta, GA (US); Lawrence Wilson, Atlanta, GA (US); Yesim Altas Tahirovic, Atlanta, GA (US); David Menaldino, Atlanta, GA (US); Scott Myers, Atlanta, GA (US); Kamalesh Poornachary, Atlanta, GA (US)

(73) Assignees: Emory Univeristy, Atlanta, GA (US); Neurop, Inc., Atlanta, GA (US)

( * ) Notice: Subject to any disclaimer, the term of this patent is extended or adjusted under 35 U.S.C. 154(b) by 119 days.

This patent is subject to a terminal disclaimer.

(21) Appl. No.: 18/688,300

(22) PCT Filed: Sep. 2, 2022

(86) PCT No.: PCT/US2022/042496

§ 371 (c)(1),
(2) Date: Feb. 29, 2024

(87) PCT Pub. No.: WO2023/034589

PCT Pub. Date: Mar. 9, 2023

(65) Prior Publication Data

US 2024/0360091 A1 Oct. 31, 2024

Related U.S. Application Data

(60) Provisional application No. 63/240,125, filed on Sep. 2, 2021.

(51) Int. Cl.

| | |
|---|---|
| ***C07D 295/135*** | (2006.01) |
| ***A61K 31/495*** | (2006.01) |
| ***A61K 31/496*** | (2006.01) |
| ***C07D 209/34*** | (2006.01) |
| ***C07D 215/22*** | (2006.01) |
| ***C07D 295/096*** | (2006.01) |

(52) U.S. Cl.

CPC ........ *C07D 295/135* (2013.01); *A61K 31/495* (2013.01); *A61K 31/496* (2013.01); *C07D 209/34* (2013.01); *C07D 215/22* (2013.01); *C07D 295/096* (2013.01)

(58) Field of Classification Search

None

See application file for complete search history.

(56) References Cited

U.S. PATENT DOCUMENTS

| | | | |
|---|---|---|---|
| 8,420,680 | B2 | 4/2013 | Liotta |
| 12,415,790 | B2 | 9/2025 | Liotta et al. |

FOREIGN PATENT DOCUMENTS

| | | |
|---|---|---|
| WO | 2002072542 | 9/2002 |
| WO | 2006023957 | 3/2006 |
| WO | 2009006437 | 1/2009 |
| WO | 2009061935 | 5/2009 |
| WO | 2009137843 | 11/2009 |
| WO | 2011075537 | 6/2011 |
| WO | 2013170072 | 11/2013 |

OTHER PUBLICATIONS

Amador et al., "Modelling and treating GRIN2A developmental and epileptic encephalopathy in mice" Journal of Neurology vol. 43 pp. 2039-2057 (2020).

Burger et al., "Mapping the Binding of GluN2B-Selective N-Methyl-Daspartate Receptor Negative Allosteric Modulators" Mol Pharmacol 82:344-359, (2012).

FDA clinical trial database: https://clinicaltrials.gov/study/NCT03565861?term=neurop&rank=2;: retrieved from the internet Jan. 7, 2025.

Fu et al., "Synthesis and Preliminary Evaluations of a Triazole-Cored Antagonist as a PET Imaging Probe ([18F]N2B-0518) for GluN2B Subunit in the Brain" ACS Chem. Neurosci. , 10, 2263-2275 (2019).

Hansen et al., "Distinct Functional and Pharmacological Properties of Triheteromeric GluN1/GluN2A/GluN2B NMDA Receptors" Neuron 81, 1084-1096, (2014).

(Continued)

*Primary Examiner* — Samantha L Shterengarts

(74) *Attorney, Agent, or Firm* — Pabst Patent Group LLP

(57) ABSTRACT

Compounds that selectively inhibit GluN2B-containing N-methyl-D-aspartic acid receptors (NMDARs) are disclosed. In some cases, the compounds selectively target GluN2B over GluN2A, GluN2C, and/or GluN2D. Generally, the compounds possess an enhanced potency to GluN2B at a pH that is more acidic compared to the physiological pH. Pharmaceutical formulations containing one or more of the compounds are also disclosed. Additionally, methods of treating a condition, disorder or disease using the compounds or their pharmaceutical formulations thereof are disclosed. Exemplary conditions, disorders, and diseases relevant to this disclosure include stroke, subarachnoid hemorrhage, cerebral ischemia, cerebral vasospasm, hypoxia, acute CNS injury, spinal cord injury, traumatic brain injury, coronary artery bypass graft, persistent or chronic cough, substance abuse disorder, opiate withdrawal, opiate tolerance, bipolar disorder, suicidal ideation, pain, fibromyalgia, depression, postpartum depression, resting tremor, dementia, epilepsy, seizure disorder, movement disorder, and neurodegenerative disease.

21 Claims, 6 Drawing Sheets

(56) References Cited

OTHER PUBLICATIONS

Hanson et al., "Implementation of a Fluorescence-Based Screening Assay Identifies Histamine H3 Receptor Antagonists Clobenpropit and lodophenpropit as Subunit-Selective N-Methyl-D-Aspartate Receptor Antagonists" vol. 333, No. 3 pp. 650-662 (2010).
International Search Report: PCT/US2022/042496 mailed Jan. 30, 2023.
Junge, et al., "The contribution of protease-activated receptor 1 to neuronal damage caused by transient focal cerebral ischemia", Proc Natl Acad Sci USA, 100: 13019-13024 (2003).
Makani and Chesler, "Endogenous alkaline transients boost postsynaptic NMDA receptor responses in hippocampal CA1 pyramidal neurons", J Neurosci, 27: 7438-7446 (2007).
Michel, et al., "Behavioural Assessment of the A2a/NR2B combination in the unilateral 6-OHDA-lesioned rat model: a new method to examine the therapeutic potential of non-dopaminergic drugs", PLoS One, 10(8):e0135949 (2015).
Michel, et al., "Unprecedented therapeutic potential with a combination of A2A/NR2B receptor antagonists as observed in the 6-OHDA lesioned rat model of Parkinson's disease", PLoS One, 9(12):e114086 (2014).
Miller, et al., "Analysis of apparent noncompetitive responses to competitive H1-histamine receptor antagonists in fluorescent imaging plate reader-based calcium assays", J Biomol Screen, 4(5):249-258 (1999).
Mosley et al., "Synthesis, structural activity-relationships, and biological evaluation of novel amide-based allosteric binding site antagonists in NR1A/NR2B N-methyl-D-aspartate receptors"Bioorganic & Medicinal Chemistry 17 6463-6480 (2009).
Mott, et al., "Phenylethanolamines inhibit NMDA receptors by enhancing proton inhibition", Nat Neurosci, 1(8): 659 (1998).
Mutch and Hansen, "Extracellular pH changes during spreading depression and cerebral ischemia: mechanisms of brain pH regulation", J Cereb Blood Flow Metab,, 4(1): 17-27 (1984).
Myer et al., "A Glutamate N-Methyl-D-Aspartate (NMDA) Receptor Subunit 2B—Selective Inhibitor of NMDA Receptor Function with Enhanced Potency at Acidic pH and Oral Bioavailability for Clinical Use" J Pharmacol Exp Ther 378:41-52, Sep. 2021.
Ng et al., "Structural insights into phenylethanolamines high-affinity binding site in NR2B from binding and molecular modeling studies" Molecular Brain 1:16 (2008).
Nutt, et al., "Effects of a NR2B selective NMDA glutamate antagonist, CP-101,606, on dyskinesia and parkinsonism", Mov Disord, 23: 1860-1866 (2008).
Porter, et al., "Functional characterization of agonists at recombinant human 5_HT2A, 5_HT2B and 5_HT2C receptors in CHO_K1 cells", Br J Pharmacol, 128:13-20 (1999).
Regan et al., "Structural Mechanism of Functional Modulation by Gene Splicing in NMDA Receptors" Regan et al., , Neuron 98, 521-529 (2018).
Rowland, "Subanesthetic ketamine: how it alters physiology and behavior in humans", Aviat Space Environ Med, 76: C52-C58 (2005).
Search Orphan Drug Designations and Approvals https://www.accessdata.fda.gov/scripts/opdlisting/oopd/detailedIndex.cfm?cfgridkey=781020; : retrieved from the internet Jan. 7, 2025.
Swartjes, et al., "Nonselective and NR2B-selective N-methyl-D-aspartic acid receptor antagonists produce antinociception and long-term relief of allodynia in acute and neuropathic pain", Anesthesiology, 115(1): 165 (2011).
Tahirovic et al., "Enantiomeric Propanolamines as selective N-Methyl-D-aspartate 2B Receptor Antagonists" J. Med. Chem. , 51, 5506-5521 (2008).
Theparambil, et al., "Astrocytes regulate brain extracellular pH via a neuronal activity-dependent bicarbonate shuttle", Nat Commun, 11(1): 5073 (2020).
Tong, et al., "Kinetics of activity-evoked pH transients and extracellular pH buffering in rat hippocampal slices", J Neurophysiol, 95: 3686 (2006).
Traynelis et al., "Control of voltage-independent zinc inhibition of NMDA receptors by the NR1 subunit", J Neurosci, 18(16): 6163 (1998).
Wang et al., "pH-sensitive NMDA inhibitors improve outcome in a murine model of SAH", Neurocrit Care, 20: 119-131 (2014).
Yi et al., "Functional and pharmacological properties of triheteromeric GluN1/2B/2D NMDA receptors" J Physiol. November ; 597(22): 5495-5514. (2019).
Yuan, et al., "Context-dependent GluN2B-selective inhibitors of NMDA receptor function are neuroprotective with minimal side effects", Neuron, , 85(6): 1305-1318 (2015).
NeurOp's website, Available at <http://www.neuropinc.com/news-events/>, 12 pages.
Blagrove, et al., "The incidence of unpleasant dreams after sub-anaesthetic ketamine", Psychopharmacol, 203: 109-120 (2009).
Bristow, et al., "Preclinical characterization of (R)-3-((3S, 4S)-3-fluoro-4-(4-hydroxyphenyl) piperidin-1-yl)-1-(4-methylbenzyl) pyrrolidin-2-one (BMS-986169), a novel, intravenous, glutamate N-methyl-d-aspartate 2B receptor negative allosteric modulator with potential in major depressive disorder", J Pharmacol Exp Ther, 363(3): 377 (2017).
Chaperon, et al., "Substitution for PCP, disruption of prepulse inhibition and hyperactivity induced by N-methyl-D-aspartate receptor antagonists: preferential involvement of the NR2B rather than NR2A subunit", Behav Pharmacol, , 14: 477 (2003).
Chenard, et al., "Separation of. alpha. 1-adrenergic and N-methyl-D-aspartate antagonist activity in a series of ifenprodil compounds", J Med Chem, 34(10): 3085 (1991).
DeVry and Jentzsch, "Role of the NMDA receptor NR2B subunit in the discriminative stimulus effects of ketamine", Behav Pharmacol,, 14: 229-235 (2003).
Diener, et al., "Treatment of acute ischaemic stroke with the low-affinity, use-dependent NMDA antagonist AR-R15896AR: a safety and tolerability study", J Neurol, 249: 561-568 (2002).
Kew, et al., "The contribution of protease-activated receptor 1 to neuronal damage caused by transient focal cerebral ischemia", J Physiol, 497: 761-772 (1996).
Kraig et al., "Alkaline and acid transients in cerebellar microenvironment", J Neurophysiol, 49(3): 831 (1983).
Labas, et al., "Synthesis, evaluation and metabolic studies of radiotracers containing a 4-(4-[18F]-fluorobenzyl) piperidin-1-yl moiety for the PET imaging of NR2B Nmda receptors", Eur J Med Chem, 46(6): 2295 (2011).
Lees, et al., "Glycine antagonist (gavestinel) in neuroprotection (GAIN International) in patients with acute stroke: a randomised controlled trial", Lancet, 355: 1949-1954 (2000).
Nicholson, et al., "The phencyclidine-like discriminative stimulus effects and reinforcing properties of the NR2B-selective N-methyl-D-aspartate antagonist CP-101 606 in rats and rhesus monkeys", Behav Pharmacol, 18: 731-743 (2007).
Preskorn, et al., "An innovative design to establish proof of concept of the antidepressant effects of the NR2B subunit selective N-methyl-D-aspartate antagonist, CP-101,606, in patients with treatment-refractory major depressive disorder", J Clin Psychopharmacol, 28:631-637 (2008).
Sacco, et al., "Glycine antagonist in neuroprotection for patients with acute stroke: GAIN Americas: a randomized controlled trial", JAMA, 285: 1719-1728 (2001).
Sykova et al., "Extracellular pH and stimulated neurons", Ciba Found Symp, 139: 220 (1988).
Tong and Chesler, "Activity-evoked extracellular pH shifts in slices of rat dorsal lateral geniculate nucleus", Brain Res., 815(2): 373 (1999).
Vicentic, et al., "Biochemistry and pharmacology of epitope-tagged α1-adrenergic receptor subtypes", J Pharmacol Exp Ther, 302: 58-65 (2002).
Weed, et al., "Negative allosteric modulators selective for the NR2B subtype of the NMDA receptor impair cognition in multiple domains", Neuropsychopharm, 46: 568-577 (2016).
Woolf and Thompson, "The induction and maintenance of central sensitization is dependent onN-methyl-d-aspartic acid receptor activation; implications for the treatment of post-injury pain hypersensitivity states", Pain, 44(3): 293-299 (1991).

(56) References Cited

OTHER PUBLICATIONS

Yurkewicz, et al., "The effect of the selective NMDA receptor antagonist traxoprodil in the treatment of traumatic brain injury", J Neurotrauma, 22: 1428-1443 (2005).

GLUN2B-SUBUNIT SELECTIVE ANTAGONISTS OF THE N-METHYL-D-ASPARTATE RECEPTORS WITH ENHANCED POTENCY AT ACIDIC PH

CROSS-REFERENCE TO RELATED APPLICATION

This application is a National Phase application under 35 U.S.C. § 371 of PCT/US2022/042496, filed Sep. 2, 2022, which claims the benefit of and priority to U.S. Provisional Application No. 63/240,125, filed Sep. 2, 2021, the entirety of which are incorporated by reference herein.

TECHNICAL FIELD

The present disclosure relates to N-methyl-D-aspartic acid receptor (NMDAR) modulators and, in particular, to GluN2B-subunit selective allosteric modulators of NMDARs that possess an enhanced potency to GluN2B at a pH that is more acidic than the physiological pH. It also relates to pharmaceutical formulations containing such an NMDAR modulator and methods for treating conditions, disorders, and diseases using such an NMDAR modulator.

BACKGROUND

Cerebral ischemia, stroke, subarachnoid hemorrhage (SAH), and traumatic brain injury (TBI) all produce substantial neuronal death that, if not fatal, can create lasting disabilities with significant societal impact. Few therapeutic options are currently available for stroke apart from the dissolution of the vessel clot in a subset of patients or clot retrieval when blockages occur in large arteries. SAH can be treated with calcium channel blockers; however, there remains considerable opportunity for improved therapies as a significant fraction of patients progress to subsequent ischemic episodes and death. No pharmacological strategy for neuroprotection in TBI has been approved yet.

Extracellular glutamate concentrations increase in injured CNS tissue in animal models and human patients with acute injuries (see Supplemental Table S1 in Yuan, et al., *Neuron,* 2015, 85(6):1305-1318). One consequence of increasing extracellular glutamate is the overactivation of NMDARs, which can be neurotoxic (Choi, et al., *J Neurosci,* 1988, 8:185-196). It logically follows that inhibition of NMDARs during insults that raise glutamate should be neuroprotective, and the efficacy of several NMDAR antagonists has been confirmed in animal models of injury. However, promising preclinical results have not yet translated to clinical success, as multiple clinical trials in stroke or TBI using NMDAR antagonists either failed to improve patient outcomes or were associated with unacceptable side effects (Yuan, et al., *Neuron,* 2015, 85(6):1305-1318). Since the discovery of GluN2B-selective antagonists, various scaffolds of highly selective GluN2B-selective antagonists have been reported and tested in preclinical and clinical studies for use in stroke (Yuan, et al., *Neuron,* 2015, 85(6):1305-1318), TBI (Yurkewicz, et al., *J Neurotrauma,* 2005, 22:1428-1443), Parkinson's disease (Michel, et al., *PLoS One,* 2014, 9(12):e114086; Michel, et al., *PLoS One,* 2015, 10(8):e0135949), depression (Bristow, et al., *J Pharmacol Exp Ther,* 2017, 363(3):377-93), and pain (Swartjes, et al., *Anesthesiology,* 2011 115(1):165-74; Labas, et al., *Eur J Med Chem,* 2011, 46(6):2295-309). Despite the apparent achievement of preclinical efficacy, no GluN2B-selective inhibitor has been approved for clinical use.

In some CNS conditions, disorders, and diseases, pH plays an important role in the physiology. Action potential firing of neurons consumes energy due to use of ionic gradients, and this is associated with the movement of multiple organic and inorganic ions across cellular membranes. High neuronal firing rates are known to alter extracellular pH (Kraig et al., *J Neurophysiol,* 1983, 49(3):831-50; Sykova et al., *Ciba Found Symp,* 1988, 139:220-35; Tong and Chesler, *Brain Res.,* 1999, 815(2):373-81), and there is a substantial proton load released by high frequency firing (Theparambil, et al., *Nat Commun,* 2020, 11(1):5073). These protons are buffered by extracellular bicarbonate, but when firing rates are high or accompanied by increased extracellular potassium (Kraig et al., *J Neurophysiol,* 1983, 49(3):831-50), compensatory mechanisms that boost the buffering capacity fail, leading to substantial acidification (Theparambil, et al., *Nat Commun,* 2020, 11(1):5073), as occurs during seizures, ischemia, hypoxia, and TBI (e.g. Mutch and Hansen, *J Cereb Blood Flow Metab,* 1984, 4(1):17-27). Repeated stimulation of small diameter primary afferent pain fibers can lead to a progressive increase in action potential discharge, often referred to as windup (Woolf and Thompson, *Pain,* 1991, 44(3):293-299), and a prolonged increase in the excitability of neurons in the spinal cord. Situations such as this, which produce high levels of action potential firing along pain pathways, are expected to lead to translocation of protons to the extracellular space as described above. In some pathological situations, such as chronic pain, firing rates can be substantial, and may create a local acidification that renders NMDAR sensitive to inhibitors with increased potency at low pH.

Taken together, there is an urgent need for GluN2B-selective NMDAR antagonists with improved pre-clinical and/or clinical outcomes, especially for CNS conditions, disorders, and diseases. Further, there is an urgent need for GluN2B-selective NMDAR antagonists having an enhanced potency to GluN2B at a pH that is more acidic than the physiological pH.

SUMMARY

The present disclosure describes negative allosteric modulators that selectively inhibit NMDARs containing the GluN2B subunit. In some cases, the negative allosteric modulators selectively target GluN2B over GluN2A, GluN2C, and/or GluN2D. Generally, the negative allosteric modulators possess an enhanced potency to GluN2B at a pH that is more acidic compared to the physiological pH.

In some embodiments, the compounds disclosed herein have a structure of Formula I or a pharmaceutically acceptable salt, hydrate, or hydrated salt of Formula I, Formula I

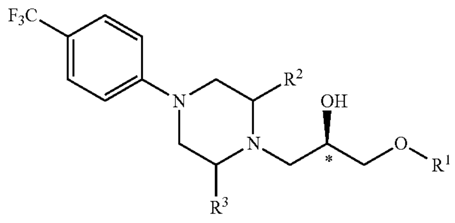

wherein $R^1$ is chosen from:

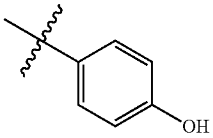
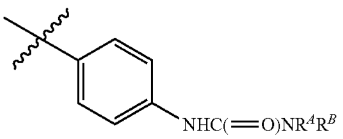
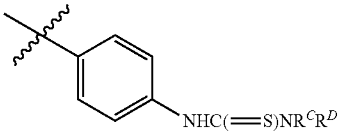
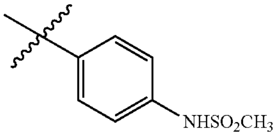
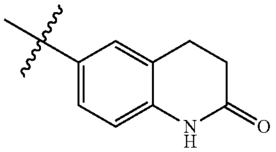
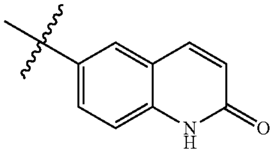
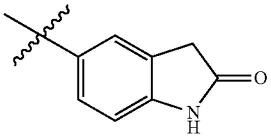
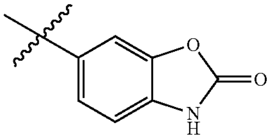
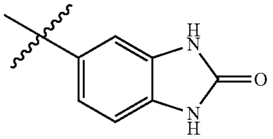
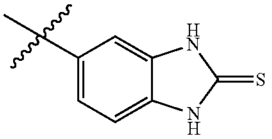
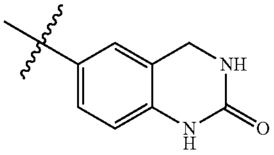
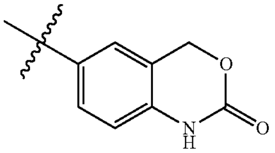
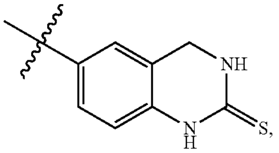

wherein $R^A$, $R^B$, $R^C$, and $R^D$ are independently chosen from hydrogen, methyl, and halomethyl, and wherein $R^2$ and $R^3$ are independently chosen from hydrogen, methyl, and halomethyl.

In some embodiments, $R^1$ is:

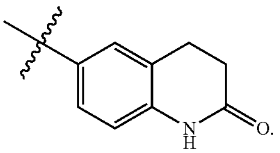 [SMILES: *c1ccc2c(c1)CCC(=O)N2]

In some embodiments, $R^1$ is:

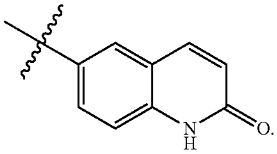 [SMILES: *c1ccc2[nH]c(=O)ccc2c1]

In some embodiments, both $R^2$ and $R^3$ are hydrogen. Exemplary compounds include:

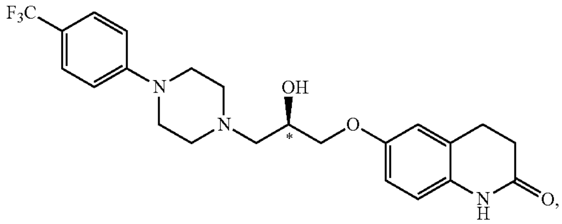
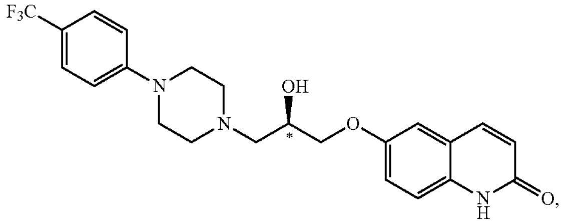
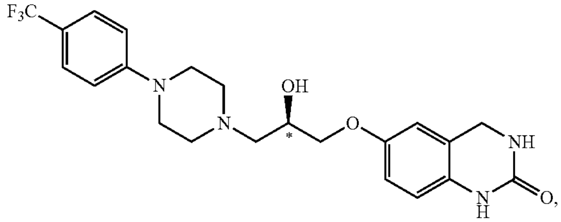

and their corresponding pharmaceutically acceptable salts, hydrates, and hydrated salts.

In some embodiments, the compounds disclosed herein have a structure of Formula II or a pharmaceutically acceptable salt, hydrate, or hydrated salt of Formula II, Formula II

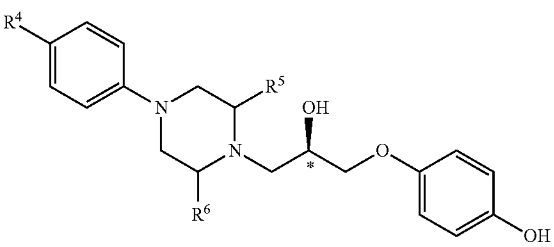

wherein $R^4$ is chosen from hydrogen, methyl, halomethyl, ethyl, haloethyl, isopropyl, and haloisopropyl, and wherein $R^5$ and $R^6$ are independently chosen from hydrogen, methyl, and halomethyl.

In some embodiments, $R^4$ is chosen from methyl and halomethyl.

In some embodiments, both $R^5$ and $R^6$ are hydrogen.

Also disclosed are compositions containing a compound described herein, wherein the compound is in greater than 80%, 85%, 90%, or 95% enantiomeric excess with respect to the stereocenter labeled by the "*" sign in the corresponding formula disclosed herein. In some embodiments, the compound in the compositions is in greater than 95% enantiomeric excess with respect to the stereocenter labeled by the "*" sign in the corresponding formula disclosed herein.

In some embodiments, the compositions contain a compound having a structure of Formula I or a pharmaceutically acceptable salt, hydrate, or hydrated salt of Formula I, wherein the compound is in greater than 80%, 85%, 90%, or 95% enantiomeric excess for the R configuration, with respect to the stereocenter labeled by the * sign, as depicted in Formula I.

In some embodiments, the compositions contain a compound having a structure of Formula II or a pharmaceutically acceptable salt, hydrate, or hydrated salt of Formula II, wherein the compound is in greater than 80%, 85%, 90%, or 95% enantiomeric excess for the R configuration, with respect to the stereocenter labeled by the * sign, as depicted in Formula II.

Also disclosed are pharmaceutical formulations of the disclosed compounds or compositions. In general, the pharmaceutical formulations also contain a pharmaceutically acceptable excipient. In some embodiments, the pharmaceutical formulations are in a form chosen from tablets, capsules, caplets, pills, beads, granules, particles, powders, gels, creams, solutions, suspensions, emulsions, and nanoparticulate formulations. In some embodiments, the pharmaceutical formulations are oral formulations. In some embodiments, the pharmaceutical formulations are intravenous formulations. In some embodiments, the pharmaceutical formulations are in the form of a lyophilized powder. In some embodiments, the pharmaceutical formulations are in the form of a sterile aqueous solution.

This disclosure also relates to (1) the compounds, compositions, and pharmaceutical formulations disclosed herein for treatment of a condition, disorder or disease disclosed herein or use as a medicament, (2) the compounds, compositions, and pharmaceutical formulations disclosed herein for use in the treatment of a condition, disorder or disease disclosed herein, or (3) the compounds, compositions, and pharmaceutical formulations disclosed herein for the manufacture of a medicament for treatment of a condition, disorder or disease disclosed herein.

This disclosure also provides methods of treating a condition, disorder or disease in a subject in need thereof. The method includes administering an effective amount of a compound, composition, or pharmaceutical formulation disclosed herein to the subject. In some embodiments, the compound, composition, or pharmaceutical formulation is administered orally or intravenously.

Exemplary conditions, disorders, and diseases relevant to this disclosure include, but are not limited to, stroke, subarachnoid hemorrhage, cerebral ischemia, cerebral vasospasm, hypoxia, acute CNS injury, spinal cord injury, traumatic brain injury, coronary artery bypass graft, persistent or chronic cough, substance abuse disorder, opiate withdrawal, opiate tolerance, bipolar disorder, suicidal ideation, pain, fibromyalgia, depression, postpartum depression, resting tremor, dementia, epilepsy, seizure disorder, movement disorder, and neurodegenerative disease.

In some embodiments, the condition, disorder or disease is pain, depression, stroke, or subarachnoid hemorrhage.

DETAILED DESCRIPTION

Figure 1:
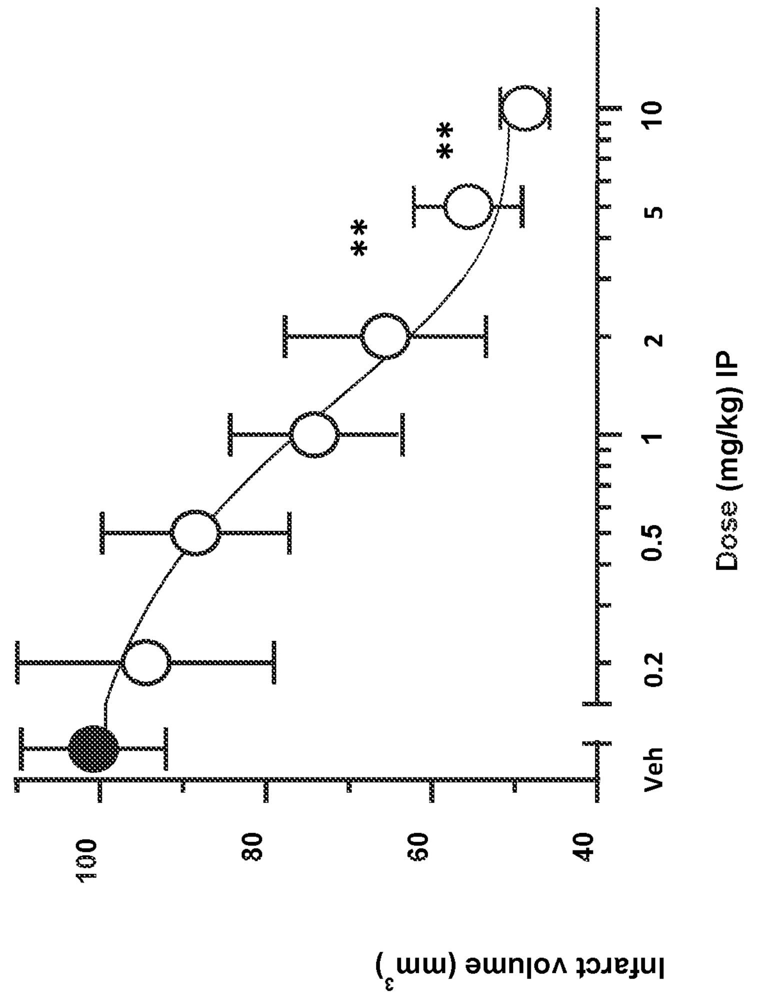
FIG. 1 is a graph showing the infarct volume ($mm^3$) plotted against the IP dose (mg/kg) of an exemplary compound (NP10679) in the MCAO model of transient ischemia in mice. The plot is pooled data across three independent experiments. Data are shown in mean±SEM for n=9 (0.2 mg/kg), 13 (0.5 mg/kg), 21 (1 mg/kg), 12 (2 mg/kg), 12 (5 mg/kg), 24 (10 mg/kg), and 34 (Veh) mice. ** p<0.01 from the vehicle control (ANOVA, Dunnett's).

The present disclosure describes negative allosteric modulators that selectively inhibit NMDARs containing the GluN2B subunit. In some embodiments, the negative allosteric modulators selectively target GluN2B over GluN2A, GluN2C, and/or GluN2D. Generally, the negative allosteric modulators possess an enhanced potency to GluN2B at a pH that is more acidic compared to the physiological pH.

Before the present disclosure is described in greater detail, it is to be understood that this disclosure is not limited to the particular embodiments described herein, and as such may, of course, vary in accordance with the scope of the present disclosure. Unless defined otherwise, all technical and scientific terms used herein have the same meaning as commonly understood by one of ordinary skill in the art to which this disclosure belongs.

All publications and patents cited in this specification are herein incorporated by reference as if each individual publication and patent were specifically and individually indicated to be incorporated by reference. They are incorporated by reference to disclose and describe the methods and/or materials in connection with which the publications and patents are cited.

As will be apparent to those of ordinary skill in the art upon reading this disclosure, each of the particular embodiments described and illustrated herein has discrete components and/or features which may be readily separated from or combined with one or more components and/or features of any of the other embodiments described herein, without departing from the scope or spirit of the present disclosure. Any recited method can be carried out in the order of events recited herein or in any other order that is logically possible.

Embodiments of the present disclosure will employ, unless otherwise indicated, techniques of medicine, organic chemistry, medicinal chemistry, biochemistry, molecular biology, pharmacology, neurology, and the like, which are within the skill of the art. Such techniques are explained fully in the literature, such as those cited herein.

I. Definitions

As used herein, the singular forms "a," "an," and "the" include plural referents unless the context clearly dictates otherwise.

As used herein, the term "subject" refers to an animal, including human and non-human animals. The non-human animals may include domestic pets, livestock and farm animals, and zoo animals. In some cases, the non-human animals may be non-human primates.

As used herein, the terms "prevent" and "preventing" include the prevention of the occurrence, onset, spread, and/or recurrence. It is not intended that the present disclosure is limited to complete prevention. For example, prevention is considered as achieved when the occurrence is delayed, the severity of the onset is reduced, or both.

As used herein, the terms "treat" and "treating" include medical management of a condition, disorder or disease of a subject as would be understood by a person of ordinary skill in the art (see, for example, Stedman's Medical Dictionary). In general, treatment is not limited to cases where the subject is cured and the condition, disorder or disease is eradicated. Rather, treatment also contemplates cases where a treatment regimen containing one of the compounds, compositions or pharmaceutical formulations of the present disclosure provides an improved clinical outcome. The improved clinical outcome may include one or more of the following: abatement, lessening, and/or alleviation of one or more symptoms that result from or are associated with the condition, disorder or disease to be treated; decreased occurrence of one or more symptoms; improved quality of life; diminishment of the extent of the condition, disorder or disease; reaching or establishing a stabilized state (i.e., not worsening) of the condition, disorder or disease; delay or slowing of the progression of the condition, disorder or disease; amelioration or palliation of the state of the condition, disorder or disease; partial or total remission (whether detectable or undetectable); and improvement in survival (whether increase in the overall survival rate or prolonging of survival when compared to expected survival if the subject were not receiving the treatment). For example, the disclosure encompasses treatment that reduces one or more symptoms of and/or cognitive deficit associated with a neurological condition, disorder or disease described herein.

As used herein, the term "physiological pH" refers to the pH that normally prevails in the human body in the absence of pathological states. Typically, it ranges between 7.35 and 7.45, with the average at 7.40.

As used herein, the terms "halogen" and "halo" refer to fluorine, chlorine, bromine, and iodine.

As used herein, the term "pharmaceutically acceptable" refers to compounds, materials, compositions, and/or formulations which are, within the scope of sound medical judgment, suitable for use in contact with the tissues of human beings and non-human animals without excessive toxicity, irritation, allergic response, or other problems or complications that commensurate with a reasonable benefit/risk ratio, in accordance with the guidelines of regulatory agencies of a certain country, such as the Food and Drug Administration (FDA) in the United States or its corresponding agencies in countries other than the United States (e.g., the European Medicines Agency (EMA)).

As used herein, the term "salt" refers to acid or base salts of the original compound. In some cases, the salt is formed in situ during preparation of the original compound, i.e., the designated synthetic chemistry procedures produce the salt instead of the original compound. In some cases, the salt is obtained via modification of the original compound. In some cases, the salt is obtained via ion exchange with an existing salt of the original compound. Examples of salts include, but are not limited to, mineral or organic acid salts of basic residues such as amines, as well as alkali or organic salts of acidic residues such as carboxylic acids and phosphorus acids. For original compounds containing a basic residue, the salts can be prepared by treating the compounds with an appropriate amount of a non-toxic inorganic or organic acid; alternatively, the salts can be formed in situ during preparation of the original compounds. Exemplary salts of the basic residue include salts with an inorganic acid selected from hydrochloric, hydrobromic, sulfuric, sulfamic, phosphoric, and nitric acids or with an organic acid selected from acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic acids. For original compounds containing an acidic residue, the salts can be prepared by treating the compounds with an appropriate amount of a non-toxic base; alternatively, the salts can be formed in situ during preparation of the original compounds. Exemplary salts of the acidic residue include salts with a base selected from ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, and histidine. Optionally, the salt can be prepared by reacting the free acid or base form of the original compound with a stoichiometric amount or more of an appropriate base or acid, respectively, in water (including aqueous solutions), an organic solvent (including organic solutions), or a mixture thereof. Lists of exemplary pharmaceutically acceptable salts can be found in Remington's Pharmaceutical Sciences, 20th Ed., Lippincott Williams & Wilkins, Baltimore, MD, 2000 as well as Handbook of Pharmaceutical Salts: Properties, Selection, and Use, Stahl and Wermuth, Eds., Wiley-VCH, Weinheim, 2002.

As used herein, the term "excipient" refers to all components present in the pharmaceutical formulations disclosed herein, other than the active ingredient (i.e., a compound or composition of the present disclosure).

As used herein, the term "effective amount" of a material refers to a nontoxic but sufficient amount of the material to provide the desired result. The exact amount required may vary from subject to subject, depending on the species, age, and general condition of the subject, the severity of the condition, disorder or disease that is being treated, the active ingredient or therapy used, and the like.

II. Compounds

The present disclosure describes negative allosteric modulators that selectively inhibit GluN2B-containing NMDARs. In some embodiments, the negative allosteric modulators selectively target the GluN2B subunit of NMDARs over the GluN2A, GluN2C, and/or GluN2D subunit(s).

In some embodiments, the potency of the negative allosteric modulators against GluN2B increases as the environment pH decreases, in the pH range from 5.0 to 9.0, from 6.0 to 8.0, from 6.5 to 8.0, or from 6.9 to 7.6. For example, the negative allosteric modulators possess an enhanced potency to GluN2B at a pH that is more acidic compared to the physiological pH. The potency against GluN2B can be assessed by the $IC_{50}$ values of the negative allosteric modulators against GluN2B, which can be readily determined by the methods described in the Examples. A lower $IC_{50}$ value corresponds to a higher potency.

To the extent that chemical formulas described herein contain one or more unspecified chiral centers, the formulas are intended to encompass all stable stereoisomers, enantiomers, and diastereomers. Such compounds can exist as a single enantiomer, a racemic mixture, a mixture of diastereomers, or combinations thereof. It is also understood that the chemical formulas encompass all tautomeric forms if tautomerization may occur.

Methods of making exemplary compounds are disclosed in the Examples. The methods are compatible with a wide variety of functional groups and compounds, and thus a wide variety of derivatives can be obtainable from the disclosed methods.

A. General Structure

Formula I

In some embodiments, the compounds have a structure of Formula I or a pharmaceutically acceptable salt, hydrate, or hydrated salt of Formula I, Formula I

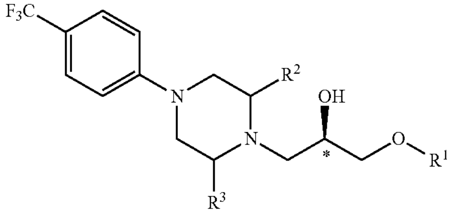

wherein $R^1$ is chosen from:

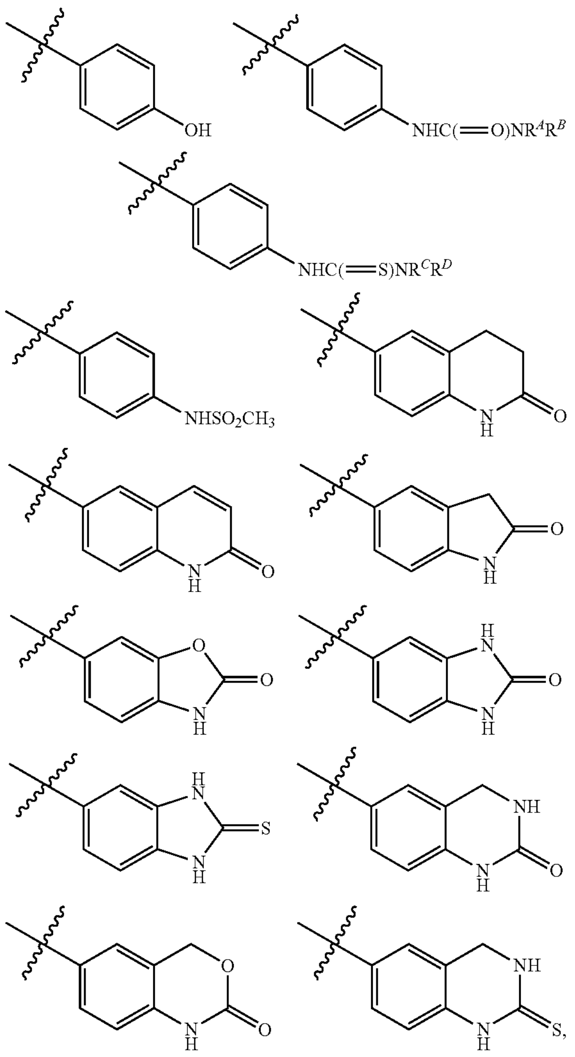

wherein $R^A$, $R^B$, $R^C$, and $R^D$ are independently chosen from hydrogen, methyl, and halomethyl (for example, fluoromethyl such as mono, di, and trifluoro methyl), and wherein $R^2$ and $R^3$ are independently chosen from hydrogen, methyl, and halomethyl (for example, fluoromethyl such as mono, di, and trifluoro methyl).

In some embodiments, the compounds are in a free-base form as shown in Formula I. In some embodiments, the compounds are pharmaceutically acceptable salts of Formula I.

In some embodiments, $R^1$ is:

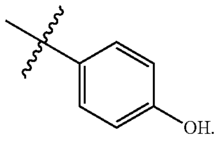 [SMILES: *c1ccc(O)cc1]

In some embodiments, $R^1$ is:

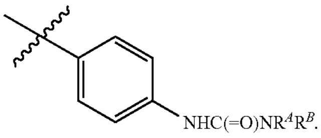

In some embodiments, $R^1$ is:

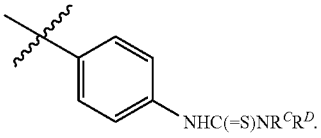

In some embodiments, $R^1$ is:

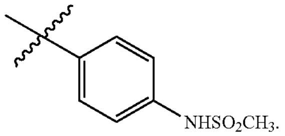

In some embodiments, $R^1$ is:

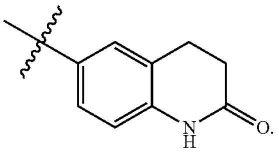 [SMILES: *c1ccc2c(c1)CCC(=O)N2]

In some embodiments, $R^1$ is:

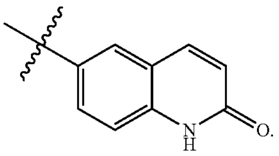 [SMILES: *c1ccc2[nH]c(=O)ccc2c1]

In some embodiments, $R^1$ is:

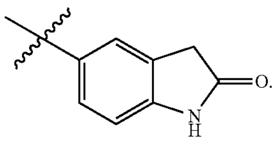 [SMILES: *c1ccc2c(c1)CC(=O)N2]

In some embodiments, $R^1$ is:

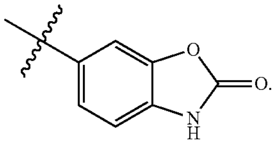 [SMILES: *c1ccc2[nH]c(=O)oc2c1]

In some embodiments, $R^1$ is:

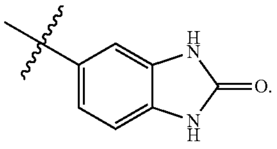 [SMILES: *c1ccc2[nH]c(=O)[nH]c2c1]

In some embodiments, $R^1$ is:

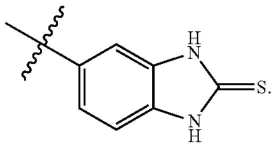 [SMILES: *c1ccc2[nH]c(=S)[nH]c2c1]

In some embodiments, $R^1$ is:

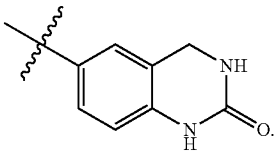 [SMILES: *c1ccc2c(c1)CNC(=O)N2]

In some embodiments, $R^1$ is:

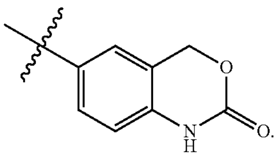 [SMILES: *c1ccc2c(c1)COC(=O)N2]

In some embodiments, $R^1$ is:

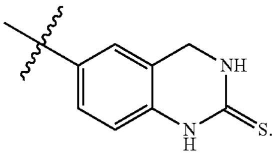 [SMILES: *c1ccc2c(c1)CNC(=S)N2]

In some embodiments, $R^A$ is hydrogen. In some embodiments, $R^B$ is hydrogen. In some embodiments, $R^A$ and $R^B$ are each hydrogen.

In some embodiments, $R^C$ is hydrogen. In some embodiments, $R^D$ is hydrogen. In some embodiments, $R^C$ and $R^D$ are each hydrogen.

In some embodiments, $R^2$ hydrogen. In some embodiments, $R^2$ is methyl. In some embodiments, $R^2$ is halomethyl, for example, fluoromethyl such as mono, di, and trifluoro methyl.

In some embodiments, $R^3$ hydrogen. In some embodiments, $R^3$ is methyl. In some embodiments, $R^3$ is halomethyl, for example, fluoromethyl such as mono, di, and trifluoro methyl.

In some embodiments, $R^2$ and $R^3$ are each hydrogen. In some embodiments, $R^2$ is hydrogen and $R^3$ is methyl or halomethyl. In some embodiments, $R^2$ is methyl or halomethyl and $R^3$ is hydrogen. In some embodiments, $R^2$ and $R^3$ are independently methyl or halomethyl.

In some embodiments, the compounds have a structure of Formula IA or a pharmaceutically acceptable salt, hydrate, or hydrated salt of Formula IA, Formula IA

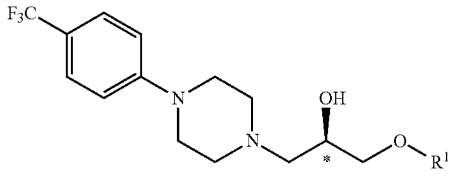

wherein $R^1$ is the same as that described above for Formula I.

Exemplary compounds include:

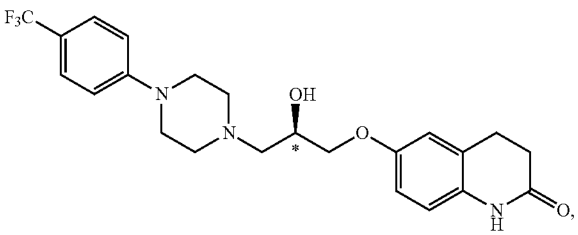

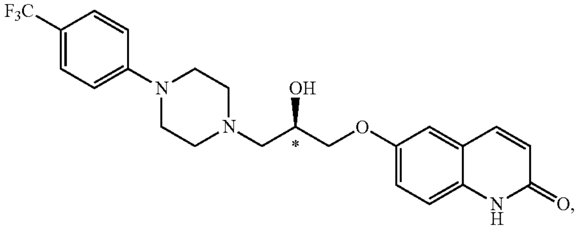

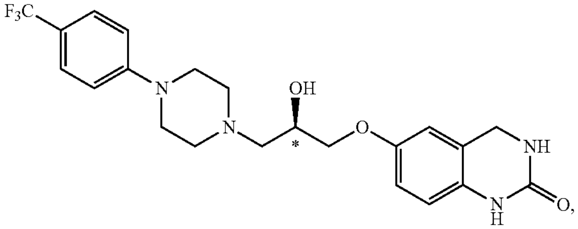

and their corresponding pharmaceutically acceptable salts, hydrates, and hydrated salts.

Formula II

In some embodiments, the compounds have a structure of Formula II or a pharmaceutically acceptable salt, hydrate, or hydrated salt of Formula II, Formula II

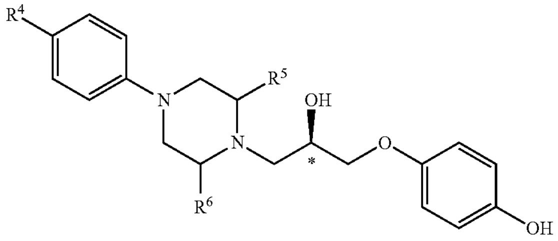

wherein $R^4$ is chosen from hydrogen, methyl, halomethyl (for example, fluoromethyl such as mono, di, and trifluoro methyl), ethyl, haloethyl (for example, fluoroethyl such as mono, di, and trifluoroethyl), isopropyl, and haloisopropyl (for example, fluoroisopropyl such as mono, di, and trifluoro isopropyl), and wherein $R^5$ and $R^6$ are independently chosen from hydrogen, methyl, and halomethyl (for example, fluoromethyl such as mono, di, and trifluoro methyl).

In some embodiments, the compounds are in a free-base form as shown in Formula II. In some embodiments, the compounds are pharmaceutically acceptable salts of Formula II.

In some embodiments, $R^4$ is hydrogen. In some embodiments, $R^4$ is methyl. In some embodiments, $R^4$ is halomethyl, for example, fluoromethyl such as mono, di, and trifluoro methyl. In some embodiments, $R^4$ is ethyl. In some embodiments, $R^4$ is haloethyl, for example, fluoroethyl such as mono, di, and trifluoroethyl. In some embodiments, $R^4$ is isopropyl. In some embodiments, $R^4$ is haloisopropyl, for example, fluoroisopropyl such as mono, di, and trifluoro isopropyl.

In some embodiments, $R^4$ is chosen from methyl and halomethyl (for example, fluoromethyl such as mono, di, and trifluoro methyl).

In some embodiments, $R^5$ hydrogen. In some embodiments, $R^5$ is methyl. In some embodiments, $R^5$ is halomethyl, for example, fluoromethyl such as mono, di, and trifluoro methyl.

In some embodiments, $R^6$ hydrogen. In some embodiments, $R^6$ is methyl. In some embodiments, $R^6$ is halomethyl, for example, fluoromethyl such as mono, di, and trifluoro methyl.

In some embodiments, $R^5$ and $R^6$ are each hydrogen. In some embodiments, $R^5$ is hydrogen and $R^6$ is methyl or halomethyl. In some embodiments, $R^5$ is methyl or halomethyl and $R^6$ is hydrogen. In some embodiments, $R^5$ and $R^6$ are independently methyl or halomethyl.

In some embodiments, the compounds have a structure of Formula IIA or a pharmaceutically acceptable salt, hydrate, or hydrated salt of Formula IIA, Formula IIA

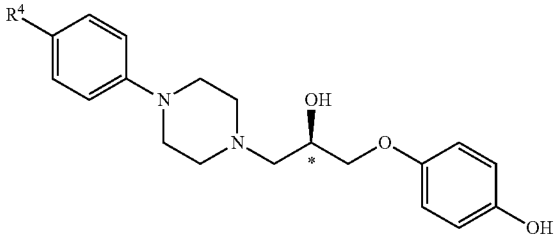

wherein $R^4$ is the same as that described above for Formula II.

B. Stereochemistry and pH Sensitivity

The compounds disclosed above are in an R configuration with respect to the chiral center labelled by the "*" sign in the formulas.

In certain embodiments, the compounds have higher potency against GluN2B than their corresponding S enantiomers. The potency against GluN2B can be assessed by the $IC_{50}$ values of the compounds against GluN2B, which can be readily determined by the methods described in the Examples. A lower $IC_{50}$ value corresponds to a higher potency.

In some embodiments, the potency of the compounds against GluN2B increases as the environment pH decreases, in the pH range from 5.0 to 9.0, from 6.0 to 8.0, from 6.5 to 8.0, or from 6.9 to 7.6. For example, the compounds possess an enhanced potency to GluN2B at a pH that is more acidic compared to the physiological pH. Here, the ratio of the $IC_{50}$ value determined at pH 7.6 to the $IC_{50}$ value determined at pH 6.9 for a particular compound is defined as the "pH boost" of the compound.

In some embodiments, the compounds have a comparable or higher pH boost compared to their corresponding S enantiomers. As used herein, "comparable" refers to a value within 25% variation to the compared value. In some embodiments, the compounds have a pH boost that is equal to more than 75% of the pH boost of their corresponding S enantiomers. In some embodiments, the compounds have a pH boost that is equal to more than 80% of the pH boost of their corresponding S enantiomers. In some embodiments, the compounds have a pH boost that is equal to more than 85% of the pH boost of their corresponding S enantiomers. In some embodiments, the compounds have a pH boost that is equal to more than 90% of the pH boost of their corresponding S enantiomers. In some embodiments, the compounds have a pH boost that is equal to more than 95% of the pH boost of their corresponding S enantiomers.

III. Compositions

Disclosed are compositions containing a compound disclosed herein. In some embodiments, the compound in the composition is in greater than 80%, 85%, 90%, or 95% enantiomeric excess, with respect to the stereocenter labeled by the "*" sign in any one of Formulas I, IA, II, and IIA. In some embodiments, the compound in the compositions is in greater than 95% enantiomeric excess with respect to the stereocenter labeled by the "*" sign in any one of Formulas I, IA, II, and IIA.

In some embodiments, the compositions contain a compound having a structure of Formula I or a pharmaceutically acceptable salt, hydrate, or hydrated salt of Formula I, wherein the compound in the compositions is in greater than 80%, 85%, 90%, or 95% enantiomeric excess for the R configuration as depicted by Formula I, with respect to the stereocenter labeled by the * sign. In some embodiments, the compound in the compositions is in greater than 95% enantiomeric excess for the R configuration as depicted by Formula I, with respect to the stereocenter labeled by the * sign.

In some embodiments, the compositions contain a compound having a structure of Formula IA or a pharmaceutically acceptable salt, hydrate, or hydrated salt of Formula IA, wherein the compound in the compositions is in greater than 80%, 85%, 90%, or 95% enantiomeric excess for the R configuration as depicted by Formula IA, with respect to the stereocenter labeled by the * sign. In some embodiments, the compound in the compositions is in greater than 95% enantiomeric excess for the R configuration as depicted by Formula IA, with respect to the stereocenter labeled by the * sign.

In some embodiments, the compositions contain a compound having a structure of Formula II or a pharmaceutically acceptable salt, hydrate, or hydrated salt of Formula II, wherein the compound in the compositions is in greater than 80%, 85%, 90%, or 95% enantiomeric excess for the R configuration as depicted by Formula II, with respect to the stereocenter labeled by the * sign. In some embodiments, the compound in the compositions is in greater than 95% enantiomeric excess for the R configuration as depicted by Formula II, with respect to the stereocenter labeled by the * sign.

In some embodiments, the compositions contain a compound having a structure of Formula IIA or a pharmaceutically acceptable salt, hydrate, or hydrated salt of Formula IIA, wherein the compound in the compositions is in greater than 80%, 85%, 90%, or 95% enantiomeric excess for the R configuration as depicted by Formula IIA, with respect to the stereocenter labeled by the * sign. In some embodiments, the compound in the compositions is in greater than 95% enantiomeric excess for the R configuration as depicted by Formula IIA, with respect to the stereocenter labeled by the * sign.

The disclosed compounds may be present in a mixture of a salt form and a non-salt form. In some embodiments, more than 50%, 60%, 70%, 80%, 90%, 95%, or 98% of the compound in the mixture may be in the non-salt form, calculated as the ratio of the weight of the non-salt form to the total weight of the salt form and the non-salt form. In some embodiments, more than 90% of the compound in the mixture may be in the non-salt form. In some embodiments, more than 50%, 60%, 70%, 80%, 90%, 95%, or 98% of the compound in the mixture may be in the salt form, calculated as the ratio of the weight of the salt form to the total weight of the salt form and the non-salt form. In some embodiments, more than 90% of the compound in the mixture may be in the salt form.

IV. Formulations

Disclosed are pharmaceutical formulations containing a compound or composition described herein. Generally, the pharmaceutical formulations also contain one or more pharmaceutically acceptable excipients.

The pharmaceutical formulations can be in a form chosen from tablets, capsules, caplets, pills, powders, beads, granules, particles, creams, gels, solutions (such as aqueous solutions, e.g., saline and buffered saline), emulsions, suspensions (including nano- and micro-suspensions), nanoparticulate formulations, etc. In some embodiments, the pharmaceutical formulations are oral formulations. In some embodiments, the pharmaceutical formulations are intravenous formulations. In some embodiments, the pharmaceutical formulations are topical formulations.

In some embodiments, the pharmaceutical formulations are in the form of a lyophilized powder. In some embodiments, the lyophilized powder is manufactured by dissolving the active ingredient (i.e., a compound or composition disclosed herein) in an aqueous solution followed by lyophilization. For example, the lyophilized powder can be prepared by dissolving the active ingredient in a phosphate-buffered hydroxy R cyclodextrin solution followed by lyophilization.

In some embodiments, the pharmaceutical formulations are in the form of a sterile aqueous solution. In some embodiments, the sterile aqueous solution is sterile PBS. In some embodiments, the sterile aqueous solution is manufactured by dissolving a lyophilized powder containing the active ingredient (i.e., a compound or composition disclosed herein) in an aqueous solution. For example, the sterile aqueous solution can be prepared by dissolving a lyophilized powder containing the active ingredient in a dose-appropriate volume of sterile PBS. In some embodiments, the lyophilized powder containing the active ingredient is the same as those described in the paragraph above.

As used herein, "emulsion" refers to a mixture of non-miscible components homogenously blended together. In some forms, the non-miscible components include a lipophilic component and an aqueous component. For example, an emulsion may be a preparation of one liquid distributed in small globules throughout the body of a second liquid. The dispersed liquid is the discontinuous phase, and the dispersion medium is the continuous phase. When oil or oleaginous substance is the dispersed liquid and water or an aqueous solution is the continuous phase, it is known as an oil-in-water emulsion, whereas when water or an aqueous solution is the dispersed phase and oil or oleaginous substance is the continuous phase, it is known as a water-in-oil emulsion.

As used herein, "biocompatible" refers to materials that are neither themselves toxic to the host (e.g., a non-human animal or human), nor degrade (if the material degrades) at a rate that produces monomeric or oligomeric subunits or other byproducts at toxic concentrations in the host.

As used herein, "biodegradable" refers to degradation or breakdown of a polymeric material into smaller (e.g., non-polymeric) subunits, or digestion of the material into smaller subunits.

As used herein, "enteric polymers" refers to polymers that become soluble in the higher pH environment of the lower gastrointestinal tract or slowly erode as the dosage form passes through the gastrointestinal tract.

As used herein, "nanoparticulate formulations" generally refers to "nanoparticles," which are particles having a diameter from about 1 nm to 1000 nm, from about 10 nm to 1000 nm, from about 100 nm to 1000 nm, or from about 250 nm to 1000 nm. In some embodiments, "nanoparticulate formulations" can also refer to "microparticles," which are particles having a diameter from about 1 micron to about 100 microns, from about 1 to about 50 microns, from about 1 to about 30 microns, from about 1 micron to about 10 microns. In some embodiments, the nanoparticulate formulation can be a mixture of nanoparticles, as defined above, and microparticles, as defined above.

As used herein, "surfactant" refers to any agent which preferentially absorbs to an interface between two immiscible phases, such as the interface between water (or aqueous solution) and an organic solvent (or organic solution), water/air interface, and organic solvent/air interface. Surfactants generally possess a hydrophilic moiety and a lipophilic moiety.

As used herein, "gel" is a semisolid system containing a dispersion of the active ingredient, i.e., a compound or composition according to the present disclosure, in a liquid vehicle that is rendered semisolid by the action of a thickening agent or polymeric material dissolved or suspended in the liquid vehicle. The liquid vehicle may include a lipophilic component, an aqueous component or both.

As used herein, "hydrogel" refers to a swollen, water-containing network of finely-dispersed polymer chains that are water-insoluble, where the polymeric molecules are in the external or dispersion phase and water (or an aqueous solution) forms the internal or dispersed phase. The polymer chains can be chemically cross-linked (chemical gels) or physically cross-linked (physical gels). Chemical gels possess polymer chains that are connected through covalent bonds, whereas physical gels have polymer chains linked by non-covalent interactions, such as van der Waals interactions, ionic interactions, hydrogen bonding interactions, and hydrophobic interactions.

As used herein, "beads" refers to beads made with the active ingredient (i.e., a compound or composition according to the present disclosure) and one or more pharmaceutically acceptable excipients. The beads can be produced by applying the active ingredient to an inert support, e.g., The beads can be produced by applying the active ingredient to an inert support, e.g., inert sugar core coated with the active ingredient. Alternatively, the beads can be produced by creating a "core" comprising both the active ingredient and at least one of the one or more pharmaceutically acceptable excipients. As used herein, "granules" refers to a product made by processing particles of the active ingredient (i.e., a compound or composition according to the present disclosure) that may or may not include one or more pharmaceutical acceptable excipients. Typically, granules do not contain an inert support and are bigger in size compared to the particles used to produce them. Although beads, granules and particles may be formulated to provide immediate release, beads and granules are usually employed to provide delayed release.

As used herein, "enzymatically degradable polymers" refers to polymers that are degraded by bacterial enzymes present in the intestines and/or lower gastrointestinal tract.

A. Physical Forms and Unit Dosages

Depending upon the manner of introduction, the compounds or compositions described herein may be formulated in a variety of ways. The pharmaceutical formulations can be prepared in various forms, such as tablets, capsules, caplets, pills, granules, powders, nanoparticle formulations, solutions (such as aqueous solutions, e.g., saline and buffered saline), suspensions (including nano- and micro-suspensions), emulsions, creams, gels, and the like.

In some embodiments, the pharmaceutical formulations are in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, suspensions (including nano- and micro-suspensions), and emulsions can also be utilized. Intravenous formulations are usually in liquid dosage forms, including solutions, emulsions, and suspensions. Suitable topical formulations include, but are not limited to, creams and gels.

In some embodiments, the pharmaceutical formulations are in a unit dosage form, and may be suitably packaged, for example in a box, blister, vial, bottle, sachet, ampoule or in any other suitable single-dose or multi-dose holder or container, optionally with one or more leaflets containing product information and/or instructions for use.

In certain embodiments, the amount of a compound disclosed herein in a unit dosage is the amount suitable for once daily dosing. In certain embodiments, multiple unit dosages are required to reach a desired total daily dosage.

In certain embodiments, a unit dosage may contain between 5 and 300 mg of a compound disclosed herein. In certain embodiments, the amount of a compound disclosed herein in a unit dosage is in the range of about 5 to about 300, about 15 to about 300, about 25 to about 300, about 50 to about 300, about 75 to about 300, about 5 to about 250, about 15 to about 250, about 25 to about 250, about 50 to about 250, about 75 to about 250, about 5 to about 200, about 15 to about 200, about 25 to about 200, about 50 to about 200, about 75 to about 200, about 5 to about 175, about 15 to about 175, about 25 to about 175, about 50 to about 175, about 75 to about 175, about 5 to about 150, about 15 to about 150, about 25 to about 150, about 50 to about 150, about 75 to about 150, or about 100 to about 150 mg.

In some embodiments, the unit dosage contains between 5 and 200 mg of a compound disclosed herein.

In some embodiments, the unit dosage contains between 25 and 200 mg of a compound disclosed herein.

In some embodiments, the unit dosage contains between 25 and 175 mg of a compound disclosed herein. In some embodiments, the unit dosage contains between 25 and 150 mg of a compound disclosed herein. In some embodiments, the unit dosage contains between 50 and 200 mg of a compound disclosed herein. In some embodiments, the unit dosage contains between 75 and 200 mg of a compound disclosed herein. In some embodiments, the unit dosage contains between 50 and 175 mg of a compound disclosed herein. In some embodiments, the unit dosage contains between 75 and 150 mg of a compound disclosed herein.

In certain embodiments, the amount of a compound disclosed herein in a unit dosage is about 25 mg, about 50 mg, about 75 mg, about 100 mg, about 125 mg, about 150 mg, about 175 mg, about 200 mg, about 225 mg, about 250 mg, about 275 mg, or about 300 mg. In a particular embodiment, the amount of a compound disclosed herein in a unit dosage is about 100 mg. In a particular embodiment, the amount of a compound disclosed herein in a unit dosage is about 150 mg.

Generally, a total daily dosage, to be administered in one or more doses to a human subject in need thereof, is between 5 and 300 mg of a compound disclosed herein. In certain embodiments, the total daily dosage, of a compound disclosed herein is in the range of about 5 to about 300, about 15 to about 300, about 25 to about 300, about 50 to about 300, about 75 to about 300, about 5 to about 250, about 15 to about 250, about 25 to about 250, about 50 to about 250, about 75 to about 250, about 5 to about 200, about 15 to about 200, about 25 to about 200, about 50 to about 200, about 75 to about 200, about 5 to about 175, about 15 to about 175, about 25 to about 175, about 50 to about 175, about 75 to about 175, about 5 to about 150, about 15 to about 150, about 25 to about 150, about 50 to about 150, about 75 to about 150, or about 100 to about 150 mg.

Generally, a total daily dosage, to be administered in one or more doses to a human subject, is between about 11 and about 667 mmol of a compound disclosed herein. In certain embodiments, the total daily dosage, of a compound disclosed herein is in the range of about 11 to about 667, about 33 to about 667, about 56 to about 667, about 111 to about 667, about 167 to about 667, about 11 to about 556, about 33 to about 556, about 56 to about 556, about 111 to about 556, about 167 to about 556, about 11 to about 445, about 33 to about 445, about 56 to about 445, about 111 to about 445, about 167 to about 445, about 11 to about 389, about 33 to about 389, about 56 to about 389, about 111 to about 389, about 167 to about 389, about 11 to about 334, about 33 to about 334, about 56 to about 334, about 111 to about 334, about 167 to about 334, or about 222 to about 334 mmol.

In certain embodiments, a course of treatment includes a loading dose per day for one or more days, following by a reduced or normal dose per day for one or more days. For example, a course of treatment may include a loading dose for the first day, followed by a reduced or normal dose per day for the rest of the course. Suitable loading doses can be selected from the exemplary total daily dosages described above. Suitable reduced or normal doses can also be selected from the exemplary total daily dosages described above. In certain embodiments, the loading dose is about 150 mg, and the reduced or normal dose is 100 mg. For example, a course of treatment may include a loading dose at 150 mg for the first day, followed by a reduced or normal dose at 100 mg per day for the rest of the course.

B. Pharmaceutically Acceptable Excipients

Exemplary pharmaceutically acceptable excipients include, but are not limited to, diluents (fillers), binders, lubricants, disintegrants, pH-modifying or buffering agents, preservatives, antioxidants, solubility enhancers, wetting or emulsifying agents, plasticizers, colorants (such as pigments and dyes), flavoring or sweetening agents, thickening agents, emollients, humectants, stabilizers, glidants, solvent or dispersion medium, surfactants, pore formers, and coating or matrix materials.

In some embodiments, the tablets, beads, granules, and particles, as described herein, contain one or more of the following pharmaceutically acceptable excipients: diluents, binders, lubricants, disintegrants, pigments, stabilizers, and surfactants. If desired, the tablets, beads, granules, and particles may also contain minor amount of nontoxic auxiliary substances such as wetting or emulsifying agents, dyes, pH-buffering agents, and preservatives.

Examples of the coating or matrix materials include, but are not limited to, cellulose polymers (such as methylcellulose, ethyl cellulose, cellulose acetate, cellulose acetate phthalate, hydroxypropyl cellulose, hydroxyethyl cellulose, hydroxymethyl cellulose, hydroxypropyl methylcellulose, hydroxypropyl methylcellulose phthalate, hydroxypropyl methylcellulose acetate succinate, cellulose acetate trimellitate, and carboxymethylcellulose sodium), vinyl polymers and copolymers (such as polyvinyl pyrrolidone, polyvinyl acetate, polyvinyl acetate phthalate, vinyl acetate-crotonic acid copolymer, and ethylene-vinyl acetate copolymer), acrylic acid polymers and copolymers (such as those formed from acrylic acid, methacrylic acid, methyl acrylate, ethyl acrylate, methyl methacrylate, ethyl methacrylate, and other methacrylic resins that are commercially available under the tradename EUDRAGIT®), enzymatically degradable polymers (such as azo polymers, pectin, chitosan, amylose and guar gum), zein, shellac, and polysaccharides. In some embodiments, the coating or matrix materials may contain one or more excipients such as plasticizers, colorants, glidants, stabilizers, pore formers, and surfactants.

In some embodiments, the coating or matrix materials are pH-sensitive or pH-responsive polymers, such as the enteric polymers commercially available under the tradename EUDRAGIT®. For example, EUDRAGIT® L30D-55 and L100-55 are soluble at pH 5.5 and above; EUDRAGIT® L100 is soluble at pH 6.0 and above; EUDRAGIT® S is soluble at pH 7.0 and above, as a result of a higher degree of esterification.

In some embodiments, the coating or matrix materials are water-insoluble polymers having different degrees of permeability and expandability, such as EUDRAGIT® NE, RL, and RS.

Depending on the coating or matrix materials, the decomposition/degradation or structural change of the pharmaceutical formulations may occur at different locations of the gastrointestinal tract. In some embodiments, the coating or matrix materials are selected such that the pharmaceutical formulations can survive exposure to gastric acid and release the active ingredient in the intestines after oral administration.

Diluents, also referred to as "fillers," can increase the bulk of a solid dosage formulation so that a practical size is provided for compression of tablets or formation of beads, granules, or particles. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate, powdered sugar, and combinations thereof.

Binders are used to impart cohesive qualities to a solid dosage formulation, and thus ensure that a tablet, bead, granule, or particle remains intact after the formation of the solid dosage formulation. Suitable binder materials include, but are not limited to, starch, pregelatinized starch, gelatin, sugars (such as sucrose, glucose, dextrose, lactose, and sorbitol), polyethylene glycol, waxes, natural and synthetic gums (such as acacia, tragacanth, and sodium alginate), cellulose (such as hydroxypropylmethylcellulose, hydroxypropylcellulose, and ethylcellulose), veegum, and synthetic polymers (such as acrylic acid copolymers, methacrylic acid copolymers, methyl methacrylate copolymers, aminoalkyl methacrylate copolymers, polyacrylic acid, polymethacrylic acid, and polyvinylpyrrolidone), and combinations thereof.

Lubricants are used to facilitate tablet manufacture. Suitable lubricants include, but are not limited to, magnesium stearate, calcium stearate, stearic acid, glycerol behenate, polyethylene glycol, talc, and mineral oil.

Disintegrants are used to facilitate disintegration or "breakup" of a solid dosage formulation after administration, and generally include, but are not limited to, starch, sodium starch glycolate, sodium carboxymethyl starch, sodium carboxymethylcellulose, hydroxypropyl cellulose, pregelatinized starch, clays, cellulose, gums, and cross-linked polymers, such as cross-linked polyvinylpyrrolidone (e.g., POLYPLASDONE® XL from GAF Chemical Corp.).

Plasticizers are normally present to produce or promote plasticity and flexibility and to reduce brittleness. Examples of plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil, and acetylated monoglycerides.

Stabilizers are used to inhibit or retard decomposition reactions of the active ingredient in the pharmaceutical formulations or stabilize particles in a dispersion. For example, when the decomposition reactions involve an oxidation reaction of the active ingredient in the pharmaceutical formulations, the stabilizer can be an antioxidant or a reducing agent. Stabilizers also include nonionic emulsifiers such as sorbitan esters, polysorbates, and polyvinylpyrrolidone.

Glidants are used to reduce sticking effects during film formation and drying. Exemplary glidants include, but are not limited to, talc, magnesium stearate, and glycerol monostearates.

Preservatives can inhibit the deterioration and/or decomposition of a pharmaceutical formulation. Deterioration or decomposition can be brought about by one or more of microbial growth, fungal growth, and undesirable chemical or physical changes. Suitable preservatives include benzoate salts (e.g., sodium benzoate), ascorbic acid, methyl hydroxybenzoate, ethyl p-hydroxybenzoate, n-propyl p-hydroxybenzoate, n-butyl p-hydroxybenzoate, potassium sorbate, sorbic acid, propionate salts (e.g., sodium propionate), chlorobutanol, benzyl alcohol, and combinations thereof.

Surfactants may be anionic, cationic, amphoteric or nonionic surface-active agents. Exemplary anionic surfactants include, but are not limited to, those containing a carboxylate, sulfonate, or sulfate ion. Examples of anionic surfactants include sodium, potassium, ammonium of long-chain (e.g., 13-21) alkyl sulfonates (such as sodium lauryl sulfate), alkyl aryl sulfonates (such as sodium dodecylbenzene sulfonate), and dialkyl sodium sulfosuccinates (such as sodium bis-(2-ethylthioxyl)-sulfosuccinate). Cationic surfactants include, but are not limited to, quaternary ammonium compounds such as benzalkonium chloride, benzethonium chloride, cetrimonium bromide, stearyl dimethylbenzyl ammonium chloride, polyoxyethylene, and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, poloxamers (such as poloxamer 401), stearoyl monoisopropanolamide, and polyoxyethylene hydrogenated tallow amide. Examples of amphoteric surfactants include, but are not limited to, sodium N-dodecyl-β-alanine, sodium N-lauryl-β-iminodipropionate, myristoamphoacetate, lauryl betaine, and lauryl sulfobetaine.

Pharmaceutical formulations in liquid forms typically contain a solvent or dispersion medium such as water, aqueous solution (e.g., saline, buffered saline, etc.), ethanol, polyol (such as glycerol, propylene glycol, and liquid polyethylene glycol), oil (such as vegetable oil, e.g., peanut oil, corn oil, sesame oil, etc.), and combinations thereof. In some embodiments, the pharmaceutical formulations in liquid forms are aqueous formulations. Suitable solvent or dispersion medium for intravenous formulations include, but are not limited to, water, saline, buffered saline (such as phosphate-buffered saline), and Ringer's solution.

C. Pharmaceutical Acceptable Carriers

In some embodiments, the pharmaceutical formulations are prepared using a pharmaceutically acceptable carrier, which encapsulates, embeds, entraps, dissolves, disperses, absorbs, and/or binds to a compound or composition disclosed herein. The pharmaceutical acceptable carrier is composed of materials that are considered safe and can be administered to a subject without causing undesirable biological side effects or unwanted interactions. Preferably, the pharmaceutically acceptable carrier does not interfere with the effectiveness of the compound or composition in performing its function. The pharmaceutically acceptable carrier can be formed of biodegradable materials, non-biodegradable materials, or combinations thereof. The pharmaceutical acceptable excipient described above may be partially or entirely present in the pharmaceutical acceptable carrier.

In some embodiments, the pharmaceutical acceptable carrier is a controlled-release carrier, such as delayed-release carriers, sustained-release (extended-release) carriers, and pulsatile-release carriers.

In some embodiments, the pharmaceutical acceptable carrier is pH-sensitive or pH-responsive. In some forms, the pharmaceutical acceptable carrier can decompose or degrade in a certain pH range. In some forms, the pharmaceutical acceptable carrier can experience a structural change when experiencing a change in the pH.

Exemplary pharmaceutical acceptable carriers include, but are not limited to: nanoparticles, microparticles, and combinations thereof, liposomes; hydrogels; polymer matrices; and solvent systems.

In some embodiments, the pharmaceutical acceptable carrier is nanoparticles, microparticles, or a combination thereof. In some embodiments, the compound or composition is embedded in the matrix formed by materials of the nanoparticles, microparticles, or combination thereof.

The nanoparticles, microparticles, or combination thereof can be biodegradable, and optionally are capable of biodegrading at a controlled rate for delivery of the compound or composition. The nanoparticles, microparticles, or combination thereof can be made of a variety of materials. Both inorganic and organic materials can be used. Both polymeric and non-polymeric materials can be used.

For example, the nanoparticles, microparticles, or combination thereof are formed of one or more biocompatible polymers. In some forms, the biocompatible polymers are biodegradable. In some forms, the biocompatible polymers are non-biodegradable. In some forms, the nanoparticles, microparticles, or combination thereof are formed of a mixture of biodegradable and non-biodegradable polymers. The polymers used to form the nanoparticles, microparticles, or combination thereof may be tailored to optimize different characteristics of the nanoparticles, microparticles, or combination thereof, including: (i) interactions between the compound and the polymer to provide stabilization of the compound and retention of activity upon delivery; (ii) rate of polymer degradation and, thereby, rate of release; (iii) surface characteristics and targeting capabilities via chemical modification; and (iv) particle porosity.

Exemplary polymers include, but are not limited to, polymers prepared from lactones such as poly(caprolactone) (PCL), polyhydroxy acids and copolymers thereof such as poly(lactic acid) (PLA), poly(glycolic acid) (PGA), poly(lactic acid-co-glycolic acid) (PLGA), and blends thereof, polyalkyl cyanoacralate, polyurethanes, polyamino acids such as poly-L-lysine (PLL), poly(valeric acid), and poly-L-glutamic acid, hydroxypropyl methacrylate (HPMA), polyanhydrides, polyorthoesters, poly(ester amides), polyamides, poly(ester ethers), polycarbonates, ethylene vinyl acetate polymer (EVA), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), celluloses including derivatized celluloses such as alkyl celluloses, hydroxyalkyl celluloses, cellulose ethers, cellulose esters, nitro celluloses, hydroxypropylcellulose, and carboxymethylcellulose, polymers of acrylic acids, such as poly(methyl (meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), and poly(octadecyl acrylate) (jointly referred to herein as "polyacrylic acids"), polydioxanone and its copolymers, polyhydroxyalkanoates, polypropylene fumarate, polyoxymethylene, poloxamers, poly(butyric acid), trimethylene carbonate, polyphosphazenes, polysaccharides, peptides or proteins, and blends thereof.

In some embodiments, the one or more biocompatible polymers forming the nanoparticles, microparticles, or combination thereof include an FDA-approved biodegradable polymer such as polyhydroxy acids (e.g., PLA, PLGA, and PGA), polyanhydride, and polyhydroxyalkanoate such as poly(3-butyrate) and poly(4-butyrate).

Materials other than polymers may be used to form the nanoparticles, microparticles, or combination thereof. Suitable materials include surfactants. The use of surfactants in the nanoparticles, microparticles, or combination thereof may improve surface properties by, for example, reducing particle-particle interactions, and render the surface of the particles less adhesive. Both naturally occurring surfactants and synthetic surfactants can be incorporated into the nanoparticles, microparticles, or combination thereof. Exemplary surfactants include, but are not limited to, phosphoglycerides such as phosphatidylcholines (e.g., L-α-phosphatidylcholine dipalmitoyl), diphosphatidyl glycerol, hexadecanol, fatty alcohols, polyoxyethylene-9-lauryl ether, fatty acids such as palmitic acid and oleic acid, sorbitan trioleate, glycocholate, surfactin, poloxomers, sorbitan fatty acid esters such as sorbitan trioleate, tyloxapol, and phospholipids.

The nanoparticles, microparticles, or combination thereof may contain a plurality of layers. The layers can have similar or different release kinetic profiles for the active ingredient. For example, the nanoparticles, microparticles, or combination thereof can have a controlled-release core surrounded by one or more additional layers. The one or more additional layers can include an instant-release layer, preferably on the surface of the nanoparticles, microparticles, or combination thereof. The instant-release layer can provide a bolus of the active ingredient shortly after administration.

The composition and structure of the nanoparticles, microparticles, or combination thereof can be selected such that the nanoparticles, microparticles, or combination thereof are pH-sensitive or pH-responsive. In some embodiments, the nanoparticles, microparticles, or combination thereof are formed of pH-sensitive or pH-responsive polymers such as the enteric polymers commercially available under the tradename EUDRAGIT®, as described above. Depending on the particle materials, the decomposition/degradation or structural change of the nanoparticles, microparticles, or combination thereof may occur at different locations of the gastrointestinal tract. In some embodiments, the particle materials are selected such that the nanoparticles, microparticles, or combination thereof can survive exposure to gastric acid and release the active ingredient in the intestines after oral administration.

D. Controlled Release

In some embodiments, the pharmaceutical formulations can be controlled-release formulations. Examples of controlled-release formulations include extended-release formulations, delayed-release formulations, and pulsatile-release formulations.

1. Extended Release

In some embodiments, the extended-release formulations are prepared as diffusion or osmotic systems, for example, as described in "Remington—The science and practice of pharmacy" (20th Ed., Lippincott Williams & Wilkins, 2000).

A diffusion system is typically in the form of a matrix, generally prepared by combining the active ingredient with a slowly dissolving carrier, optionally into a tablet form. Suitable types of materials used in the preparation of the matrix include plastics, hydrophilic polymers, and fatty compounds. Suitable plastics include, but are not limited to, methyl acrylate-methyl methacrylate copolymer, polyvinyl chloride, and polyethylene. Suitable hydrophilic polymers include, but are not limited to, cellulosic polymers such as methyl ethyl cellulose, hydroxyalkylcelluloses (such as hydroxypropylcellulose and hydroxypropylmethylcellulose), sodium carboxymethylcellulose, CARBOPOL® 934, polyethylene oxides, and combinations thereof. Suitable fatty compounds include, but are not limited to, various waxes such as carnauba wax and glyceryl tristearate, wax-type substances such as hydrogenated castor oil and hydrogenated vegetable oil, and combinations thereof.

In some embodiments, the plastic is a pharmaceutically acceptable acrylic polymer. In some embodiments, the pharmaceutically acceptable acrylic polymer is chosen from acrylic acid and methacrylic acid copolymers, methyl methacrylate copolymers, ethoxyethyl methacrylate copolymers, cyanoethyl methacrylate copolymers, aminoalkyl methacrylate copolymers, poly(acrylic acid), poly(methacrylic acid), methacrylic acid alkylamine copolymers, poly(methyl methacrylate), poly(methacrylic acid), polymethacrylate, polyacrylamide, poly(methacrylic acid anhydride), and glycidyl methacrylate copolymers.

In some embodiments, the pharmaceutically acceptable acrylic polymer can be an ammonio methacrylate copolymer. Ammonio methacrylate copolymers are well known in the art and are described as fully polymerized copolymers of acrylic and methacrylic acid esters with a low content of quaternary ammonium groups.

In some embodiments, the pharmaceutically acceptable acrylic polymer is an acrylic resin lacquer such as those commercially available under the tradename EUDRAGIT®. In some embodiments, the pharmaceutically acceptable acrylic polymer contains a mixture of two acrylic resin lacquers, EUDRAGIT® RL (such as EUDRAGIT® RL30D) and EUDRAGIT® RS (EUDRAGIT® RS30D). EUDRAGIT® RL30D and EUDRAGIT® RS30D are copolymers of acrylic and methacrylic acid esters with a low content of quaternary ammonium groups, the molar ratio of ammonium groups to the remaining neutral methacrylic esters being 1:20 in EUDRAGIT® RL30D and 1:40 in EUDRAGIT® RS30D. The code designations RL (high permeability) and RS (low permeability) refer to the permeability properties of these polymers. EUDRAGIT® RL/RS mixtures are insoluble in water and in digestive fluids. However, multi-particulate systems formed to include the same are swellable and permeable in aqueous solutions and digestive fluids. The EUDRAGIT® RL/RS mixtures may be prepared in any desired ratio in order to ultimately obtain a sustained-release formulation having a desirable release profile. Suitable sustained-release multi-particulate systems may be obtained, for instance, from 90% EUDRAGIT® RL+10% EUDRAGIT® RS, to 50% EUDRAGIT® RL+50% EUDRAGIT® RS, and to 10% EUDRAGIT® RL+90% EUDRAGIT® RS. In some embodiments, the pharmaceutically acceptable acrylic polymer can also be or include other acrylic resin lacquers, such as EUDRAGIT® S-100, EUDRAGIT® L-100, and mixtures thereof.

Matrices with different release mechanisms or profiles can be combined in a final dosage form containing single or multiple units. Examples of multiple units include, but are not limited to, multilayer tablets and capsules containing beads, granules, and/or particles of the active ingredient. An immediate release portion can be added to the extended-release system by means of either applying an immediate release layer on top of the extended-release core using a coating or compression process or in a multiple unit system such as a capsule containing both extended- and immediate-release beads.

Extended-release tablets containing one or more of the hydrophilic polymers can be prepared by techniques commonly known in the art such as direct compression, wet granulation, and dry granulation.

Extended-release tablets containing one or more of the fatty compounds can be prepared using methods known in the art such as direct blend methods, congealing methods, and aqueous dispersion methods. In the congealing methods, the active ingredient is mixed with the fatty compound(s) and either spray-congealed or congealed and screened and processed.

Alternatively, the extended-release formulations can be prepared using osmotic systems or by applying a semi-permeable coating to a solid dosage form. In the latter case, the desired release profile can be achieved by combining low permeable and high permeable coating materials in suitable proportions.

2. Delayed Release

Delayed-release formulations can be prepared by coating a solid dosage form with a coating. In some embodiments, the coating is insoluble and impermeable in the acidic environment of the stomach, and becomes soluble or permeable in the less acidic environment of the intestines and/or the lower GI tract. In some embodiments, the solid dosage form is a tablet for incorporation into a capsule, a tablet for use as an inner core in a "coated core" dosage form, or a plurality of beads, granules, and/or particles containing the active ingredient, for incorporation into either a tablet or capsule.

Suitable coating materials include bioerodible, gradually hydrolyzable, gradually water-soluble, and enzymatically degradable polymers, such as those described above. In some embodiments, the coating material is or contains enteric polymers. Combinations of different coating materials may also be used. Multilayer coatings using different coating materials may also be applied.

Suitable weights for the coating or coating material may be readily determined by those skilled in the art by evaluating individual release profiles of the formulations prepared with different quantities of the coating material.

The coating material may also contain one or more conventional additives, such as plasticizers (optionally representing about 10 wt % to 50 wt % relative to the dry weight of the coating material), colorants, stabilizers, glidants, etc., such as those described above.

3. Pulsatile Release

Pulsatile-release formulations release a plurality of doses of the active ingredient at spaced-apart time intervals. Generally, upon administration, such as oral administration, of the pulsatile-release formulations, release of the initial dose is substantially immediate, e.g., the first release "pulse" occurs within about three hours, two hours, or one hour of administration. This initial pulse may be followed by a first time-interval (lag time) during which very little or no active ingredient is released from the formulations, after which a second dose may be released. Similarly, a second lag time (nearly release-free interval) between the second and third release pulses may be designed. The duration of the lag times will vary depending on the formulation design, especially on the length of the dosing interval, e.g., a twice daily dosing profile, a three times daily dosing profile, etc.

For pulsatile-release formulations providing a twice daily dosage profile, they deliver two release pulses of the active ingredient. In some embodiments, the nearly release-free interval between the first and second release pulses may have a duration of between 3 hours and 14 hours.

For pulsatile-release formulations providing a three daily dosage profile, they deliver three release pulses of the active ingredient. In some embodiments, the nearly release-free interval between two adjacent pulses may have a duration of between 2 hours and 8 hours.

In some embodiments, the pulsatile-release formulations contain a plurality of pharmaceutically acceptable carriers with different release kinetics.

In some embodiments, the pulsatile-release formulations contain a pharmaceutically acceptable carrier with a plurality of layers loaded with the active ingredient. In some embodiments, the layers may have different release kinetics. In some embodiments, the layers may be separated by a delayed-release coating. For example, the pulsatile-release formulations may have a first layer loaded with the active ingredient on the surface for the first release pulse and a second layer, e.g., a core loaded with the active ingredient, for the second release pulse; the second layer may be surrounded by a delayed-release coating, which creates a lag time between the two release pulses.

In some embodiments, the pulsatile-release profile is achieved with formulations that are closed and optionally sealed capsules housing at least two "dosage units" wherein each dosage unit within the capsules provides a different release profile. In some embodiments, at least of one of the dosage units is a delayed-release dosage unit. Control of the delayed-release dosage unit(s) may be accomplished by a controlled-release polymer coating on the dosage unit(s), or by incorporation of the active ingredient in a controlled-release polymer matrix. In some embodiments, each dosage unit may comprise a compressed or molded tablet, wherein each tablet within the capsule provides a different release profile.

E. Exemplary Formulations for Different Routes of Administration

A subject suffering from a condition, disorder or disease as described herein, can be treated by either targeted or systemic administration, via oral, inhalation, topical, trans- or sub-mucosal, subcutaneous, parenteral, intramuscular, intravenous, or transdermal administration of a pharmaceutical formulation containing a compound or composition described herein. In some embodiments, the pharmaceutical formulation is suitable for oral administration. In some embodiments, the pharmaceutical formulation is suitable for inhalation or intranasal administration. In some embodiments, the pharmaceutical formulation is suitable for transdermal or topical administration. In some embodiments, the pharmaceutical formulation is suitable for subcutaneous, intravenous, intraperitoneal, intramuscular, parenteral, or submucosal administration.

In some embodiments, the pharmaceutical formulation is an oral pharmaceutical formulation. In some embodiments, the active ingredient may be incorporated with one or more pharmaceutically acceptable excipients as described above and used in the form of tablets, pills, caplets, or capsules. For example, the corresponding oral pharmaceutical formulation may contain one or more of the following pharmaceutically acceptable excipients or those of a similar nature: a binder as described above, a disintegrant as described above, a lubricant as described above, a glidant as described above, a sweetening agent (such as sucrose and saccharin), and a flavoring agent (such as methyl salicylate and fruit flavorings). In some embodiments, when the oral pharmaceutical formulation is in the form of capsules, it may contain, in addition to the material(s) listed above, a liquid carrier (such as a fatty oil). In some embodiments, when the oral pharmaceutical formulation is in the form of capsules, each capsule may contain a plurality of beads, granules, and/or particles of the active ingredient. In some embodiments, the oral pharmaceutical formulation may contain one or more other materials which modify the physical form or one or more pharmaceutical properties of the dosage unit, for example, coatings of polysaccharides, shellac, or enteric polymers as described in previous sections.

In some embodiments, the oral pharmaceutical formulation can be in the form of an elixir, suspension, syrup, wafer, chewing gum or the like. A syrup may contain, in addition to the active ingredient, one or more sweetening agents (such as sucrose and saccharine), one or more flavoring agents, one or more preservatives, and/or one or more dyes or colorings.

In some embodiments, the pharmaceutical formulation is a parenteral pharmaceutical formulation. In some embodiments, the parenteral pharmaceutical formulation can be enclosed in an ampoule, syringe, or a single or multiple dose vial made of glass or plastic. In some embodiments, the parenteral pharmaceutical formulation is an intravenous pharmaceutical formulation. In some embodiments, the intravenous pharmaceutical formulation contains a liquid, pharmaceutically acceptable carrier for the active ingredient. Suitable liquid, pharmaceutically acceptable carriers include, but are not limited to, physiological saline, bacteriostatic water, Cremophor EL™ (BASF, Parsippany, NJ), phosphate buffered saline (PBS), and combinations thereof.

In some embodiments, the pharmaceutical formulation is a topical pharmaceutical formulation. Suitable forms of the topical pharmaceutical formulation include lotions, suspensions, ointments, creams, gels, tinctures, sprays, powders, pastes, slow-release transdermal patches, and suppositories for application to rectal, vaginal, nasal or oral mucosa. In some embodiments, thickening agents, emollients (such as mineral oil, lanolin and its derivatives, and squalene), humectants (such as sorbitol), and/or stabilizers can be used to prepare the topical pharmaceutical formulations. Examples of thickening agents include petrolatum, beeswax, xanthan gum, and polyethylene.

In some embodiments, the pharmaceutical formulation is an intranasal pharmaceutical formulation. In some embodiments, the intranasal pharmaceutical formulation is in the form of an aqueous suspension, which can be optionally placed a pump spray bottle. Other than water, the aqueous suspension may contain one or more pharmaceutically acceptable excipients, such as suspending agents (e.g., microcrystalline cellulose, sodium carboxymethylcellulose, hydroxypropyl-methyl cellulose), humectants (e.g., glycerol and propylene glycol), acids, bases, and/or pH-buffering agents for adjusting the pH (e.g., citric acid, sodium citrate, phosphoric acid, sodium phosphate, and combinations thereof), surfactants (e.g., Polysorbate 80), and preservatives (e.g., benzalkonium chloride, phenylethyl alcohol, and potassium sorbate).

In some embodiments, the pharmaceutical formulation is an inhalation pharmaceutical formulation. In some embodiments, the inhalation pharmaceutical formulation may be in the form of an aerosol suspension, a dry powder, or a liquid suspension. The inhalation pharmaceutical formulation may be prepared for delivery as a nasal spray or an inhaler, such as a metered dose inhaler (MDI). In some embodiments, MDIs can deliver aerosolized particles suspended in chlorofluorocarbon propellants such as CFC-11 and CFC-12, or non-chlorofluorocarbons or alternate propellants such as fluorocarbons (e.g., HFC-134A, HFC-227, etc.), with or without surfactants or suitable bridging agents. Dry-powder inhalers can also be used, either breath activated or delivered by pressure.

In some embodiments, the active ingredient is prepared with a pharmaceutically acceptable carrier that will protect it against rapid degradation or elimination from the body of the subject after administration, such as the controlled-release formulations as described in previous sections.

V. Methods of Use

Disclosed are methods of treating a condition, disorder or disease in a subject in need thereof. The methods include administering an effective amount of a compound, composition or pharmaceutical formulation disclosed herein to the subject.

The compound, composition or pharmaceutical formulation can be administered in a variety of manners, depending on whether local or systemic administration is desired. In some embodiments, the compound, composition or pharmaceutical formulation is directly administered to a specific bodily location of the subject, e.g., topically administration and intranasal administration. In some embodiments, the compound, composition or pharmaceutical formulation is administered in a systemic manner, such as enteral administration (e.g., oral administration) and parenteral administration (e.g., injection, infusion, and implantation). Exemplary administration routes include oral administration, intravenous administration such as intravenous injection or infusion, intranasal administration, and topical administration. In some embodiments, the compound, composition or pharmaceutical formulation is administered orally. In some embodiments, the compound, composition or pharmaceutical formulation is administered intravenously. In some embodiments, the compound, composition or pharmaceutical formulation is administered intranasally.

In some embodiments, the subject is a human. In some embodiments, the subject is a human under the age of 18. In some embodiments, the subject is a non-human animal, such as domestic pets, livestock and farm animals, and zoo animals. In some embodiments, the non-human animal may be a non-human primate.

A. Indications

Normal synaptic transmission does not produce detectable acidification. Rather, excitatory synaptic transmission typically produces a brief alkalinization (Tong, et al., *J Neurophysiol,* 2006, 95:3686-97; Makani and Chesler, *J Neurosci,* 2007, 27:7438-7446). Therefore, under normal excitatory synaptic transmission, the compounds disclosed herein do not appreciably engage their pH sensitivity. In addition, reduced extracellular pH usually does not occur at extrasynaptic NMDARs in normal brain. Therefore, the compounds disclosed herein are less effective in inhibiting GluN2B-containing NMDARs under normal conditions.

The pH sensitivity and high potency of the compounds disclosed herein are suitable for conditions, disorders and diseases that are accompanied by acidification of the extracellular environment of GluN2B-containing NMDARs. Notably, the pH sensitivity of the compounds can be effective in a range of indications that may lead to local acidification in the brain, such as stroke and subarachnoid hemorrhage.

The enhanced potency of the compounds against GluN2B-containing NMDARs under acidified extracellular environment can facilitate their neuroprotective effect following acute injury (such as ischemia). Ischemia, driven by both elevated $CO_2$ producing $HCO_3^-$ and $H^+$ and a shift to anaerobic metabolism with production of lactic acid, typically reduces pH throughout the extracellular space. These mechanisms, which are strong drivers of infarct and penumbral acidification during ischemia, can affect both synaptic and non-synaptic GluN2B-containing NMDARs.

The utility of the compounds of this disclosure may also be applied to conditions, disorders, and diseases with high-frequency neuronal firing that produces metabolic changes in pH and local acidification, such as inflammatory pain.

Exemplary conditions, disorders, and diseases that can be treated by the disclosed compounds, compositions, and formulations include, but are not limited to, stroke, subarachnoid hemorrhage, cerebral ischemia, cerebral vasospasm, hypoxia, acute CNS injury, spinal cord injury, traumatic brain injury, coronary artery bypass graft, persistent or chronic cough, substance abuse disorder, opiate withdrawal, opiate tolerance, bipolar disorder, suicidal ideation, pain, fibromyalgia, depression, postpartum depression, resting tremor, dementia, epilepsy, seizure disorder, movement disorder, and neurodegenerative disease.

In some embodiments, the condition, disorder or disease is chosen from pain, depression, stroke, and subarachnoid hemorrhage.

In some embodiments, the condition, disorder or disease is stroke. In some embodiments, the compound, composition or pharmaceutical formulation is used to treat or prevent stroke-associated damages. In some embodiments, the compound, composition or pharmaceutical formulation is administered under emergency care for stroke, for maintenance treatment of stroke, and/or for rehabilitation of stroke.

In some embodiments, the condition, disorder or disease is subarachnoid hemorrhage (SAH), such as aneurysmal SAH. In some embodiments, the compound, composition or pharmaceutical formulation is used to treat or prevent SAH-associated damages. In some embodiments, the compound, composition or pharmaceutical formulation is administered under emergency care for a SAH, for maintenance treatment of SAH, and/or for rehabilitation of SAH.

SAH refers to an abnormal condition in which blood collects beneath the arachnoid mater, a membrane that covers the brain. This area, called the subarachnoid space, normally contains cerebrospinal fluid. The accumulation of blood in the subarachnoid space, and the vasospasm of the vessels which results from it, can lead to stroke, seizures, and other complications. SAH can be spontaneous or caused by a head injury. The compound, composition or pharmaceutical formulation can be used to treat a subject experiencing SAH. For example, the compound, composition or pharmaceutical formulation can be used to prevent or limit one or more of the toxic effects of SAH, including, for example, stroke and ischemia that can result from SAH. Alternatively, the compound, composition or pharmaceutical formulation can be used to treat a subject with traumatic subarachnoid hemorrhage caused by a head injury.

In certain embodiments, the compound, composition or pharmaceutical formulation can be used to ameliorate neurological deficits arising from SAH, for example aneurysmal SAH. In certain embodiments, the compound, composition or pharmaceutical formulation is administered early in treatment of the condition, for example around the time of surgery to stop cranial bleeding. Delayed cerebral ischemia (DCI) occurs in ~30% of cases after aneurysmal SAH. In certain embodiments, the compound, composition or pharmaceutical formulation is administered for prevention of DCI associated with SAH. In certain embodiments, the compound, composition or pharmaceutical formulation is administered through the time of highest risk for DCI, e.g., 3-14 days post initial bleed.

In some embodiments, the condition, disorder or disease is pain. In some embodiments, the pain is chronic pain. In some embodiments, the pain is cancer pain. In some embodiments, the pain is neuropathic pain. Examples of neuropathic pain include peripheral diabetic neuropathy, postherpetic neuralgia, complex regional pain syndromes, peripheral neuropathies, rheumatoid arthritis, chemotherapy-induced neuropathic pain, cancer neuropathic pain, neuropathic low back pain, HIV neuropathic pain, trigeminal neuralgia, and central post-stroke pain.

In some embodiments, the neuropathic pain results from peripheral or CNS pathologic events, including, but not limited to, trauma, ischemia, infections (such as HIV infection, herpes zoster shingles, and postherpetic neuralgia), metabolic diseases and endocrinologic disorders (such as diabetes mellitus, diabetic neuropathy, amyloidosis, and amyloid polyneuropathy (primary and familial)), vasculitic neuropathy, neuropathy associated with Guillain-Barre syndrome, neuropathy associated with Fabry's disease, entrapment due to anatomic abnormalities, trigeminal and other CNS neuralgias, malignancies, cryptogenic causes (such as idiopathic distal small-fiber neuropathy), inflammatory conditions or autoimmune disorders (such as demyelinating inflammatory disorders, rheumatoid arthritis, systemic lupus erythematosus, and Sjogren's syndrome), compression of nerve fibers (such as radiculopathies and carpal tunnel syndrome), exposure to toxins or drugs, dietary or absorption abnormalities, immunoglobulinemias, and hereditary abnormalities and amputations (including mastectomy).

In some embodiments, the condition, disorder or disease is depression or postpartum depression. In some embodiments, the depression is treatment-resistant depression.

In some embodiments, the condition, disorder or disease is neurodegenerative disease. In some embodiments, the neurodegenerative disease is Huntington's disease, Alzheimer's disease, or Parkinson's disease. In some embodiments, the compound, composition or pharmaceutical formulation is used to reduce one or more symptoms of the neurodegenerative disease. Exemplary symptoms include dementia (for Alzheimer's disease) and dystonia and related movement disorders (for Parkinson's disease). In some embodiments, the compound, composition or pharmaceutical formulation is used to provide cognitive enhancement to the subject that suffers from the neurodegenerative disease.

In some embodiments, the condition, disorder or disease is epilepsy or seizure disorder. In some embodiments, the epilepsy or seizure disorder of the subject in need of treatment may include epilepsy that are inadequately controlled by existing medications (i.e., treatment-resistant epilepsy), infantile spasms, and epilepsy or seizure disorder caused by a rare disease or genetic condition (e.g., genetic mutation) that produces epilepsy, seizures, spasms, abnormally hypersynchronous brain activity, and/or other conditions associated with enhanced neuronal synchrony. In some embodiments, the subject may be pediatric patients suffering from the epilepsy or seizure disorder. In some embodiments, the compound, composition or pharmaceutical formulation is used to reduce the severity and/or intensity of the epilepsy or seizure disorder of the subject. In some embodiments, the compound, composition or pharmaceutical formulation is used to reduce the frequency of the epilepsy or seizure disorder of the subject.

In some embodiments, the condition, disorder or disease is dementia. In some embodiments, the dementia is AIDS-induced dementia.

In some embodiments, the condition, disorder or disease is hypoxia. In some embodiments, the compound, composition or pharmaceutical formulation is used to treat or prevent hypoxia-associated damages. In some embodiments, the compound, composition or pharmaceutical formulation is administered under emergency care for a hypoxia event, for maintenance treatment of hypoxia, and/or for rehabilitation of hypoxia. In some embodiments, the hypoxia is induced by respiratory insufficiency, prolonged use of ventilator, or both. In some embodiments, the respiratory insufficiency, prolonged use of ventilator, or both is associated with COVID-19, including hospitalization caused by COVID-19.

In some embodiments, the condition, disorder or disease is cerebral ischemia. In some embodiments, the compound, composition or pharmaceutical formulation is used to treat or prevent cerebral ischemia-associated damages. In some embodiments, the compound, composition or pharmaceutical formulation is administered under emergency care for a cerebral ischemia event, for maintenance treatment of cerebral ischemia, and/or for rehabilitation of cerebral ischemia. In some embodiments, the cerebral ischemia is caused by traumatic brain injury, coronary artery bypass graft, carotid angioplasty, or neonatal ischemia following hypothermic circulatory arrest.

In some embodiments, the condition, disorder or disease is cerebral vasospasm. In some embodiments, the cerebral vasospasm is caused or induced by SAH.

B. Dosing and Administration

In some embodiments, the compound, composition or pharmaceutical formulation is administered for a sufficient time period to alleviate one or more undesired symptoms and/or one or more clinical signs associated with the condition, disorder or disease being treated. In some embodiments, the compound, composition or pharmaceutical formulation is administered less than three times daily. In some embodiments, the compound, composition or pharmaceutical formulation is administered once or twice daily. In some embodiments, the compound, composition or pharmaceutical formulation is administered once daily. In some embodiments, the compound, composition or pharmaceutical formulation is administered in a single oral dosage once a day. In some embodiments, the compound, composition or pharmaceutical formulation is administered in a single intravenous dosage once a day.

For each administration, the dose of the compound may be between 5 and 300 mg, or as described above. In some embodiments, the dose of the compound for each administration is between 25 and 200 mg. In some embodiments, the dose of the compound for each administration is between 25 and 175 mg. In some embodiments, the dose of the compound for each administration is between 25 and 150 mg. In some embodiments, the dose of the compound for each administration is between 50 and 200 mg. In some embodiments, the dose of the compound for each administration is between 75 and 200 mg. In some embodiments, the dose of the compound for each administration is between 50 and 175 mg. In some embodiments, the dose of the compound for each administration is between 75 and 150 mg.

In certain embodiments, the compound, composition or pharmaceutical formulation is administered at a loading dose of the compound per day for one or more days and then at a reduced or normal dose of the compound per day for one or more days to complete a treatment course. For example, the compound, composition or pharmaceutical formulation is administered at a loading dose of the compound for the first day and then at a reduced or normal dose per day for the rest of the course. Suitable loading doses of the compound can be selected from the exemplary total daily dosages described above. Suitable reduced or normal doses of the compound can also be selected from the exemplary total daily dosages described above. In certain embodiments, the loading dose of the compound is about 150 mg, and the reduced or normal dose of the compound is 100 mg. For example, the compound, composition or pharmaceutical formulation is administered at a 150 mg loading dose of the compound for the first day and then at a 100 mg reduced or normal dose of the compound per day for the rest of the course.

EXAMPLES

The examples below describe studies to generate and evaluate GluN2B-selective negative allosteric NMDAR modulators that possess an enhanced potency to GluN2B at pH 6.9 compared to pH 7.6.

Example 1. Synthesis and Characterization Exemplary Compounds

NP10679

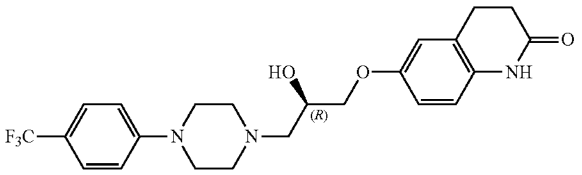

NP10309

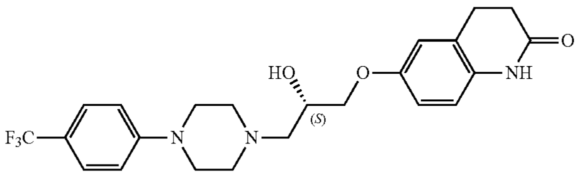

A. Synthetic Procedures

A suspension of (R)-6-(oxiran-2-ylmethoxy)-3,4-dihydroquinolin-2(1H)-one (100 g, 0.456 mol) and 1-(4-(trifluoromethyl)phenyl)piperazine (105 g, 0.456 mol) in ethanol (1 L) was stirred at 75° C. for 21 hours with monitoring by HPLC. The reaction became a clear solution within 15 minutes at 75° C. The reaction mixture was cooled to 50° C. and the precipitated solid was filtered and washed with ethanol (200 mL). The collected solid was dried under vacuum to afford the crude product (175 g, 85.3%).

Crude NP10679 (260 g from multiple batches) was placed in a 5 L round bottom flask to which was added a premixed solution of methanol:acetone (1:1) with constant stirring. The suspension was heated to 50° C. with stirring until it became clear (approximately 30 min) and then filtered through a 2 μM filter. The clear solution was cooled to 30° C. over 15 minutes and added to water (13 L) under vigorous stirring over a 10-minute period. The precipitated solid was stirred for 30 minutes at 30° C., filtered, washed with water (7.8 L), and dried in a vacuum tray drier at 70° C. for 48 hours. This recrystallization produces 255 g of a white solid (98% yield). The purity and chiral purity of the recrystallized product were determined to be >99% (by HPLC) and >98% (by chiral HPLC), respectively.

NP10309 was synthesized using a similar method with (S)-6-(oxiran-2-ylmethoxy)-3,4-dihydroquinolin-2(1H)-one and 1-(4-(trifluoromethyl)phenyl)piperazine as the starting materials.

Other compounds in Tables 1 and 2 were synthesized using similar methods as described above as well as the methods described in U.S. Pat. No. 8,420,680 and Wang et al., *Neurocrit Care,* 2014, 20:119-131. In general, the chiral center in the compounds were created via ring-opening reactions of the corresponding epoxides.

For example, synthesis of the benzyl urea-containing compound, 10075, was described in Wang et al., *Neurocrit Care,* 2014, 20:119-131. Other benzyl urea-containing compounds, including 10131, 10165, 10166, 10189, 10214, 10215, 10222, 10224, 10225, 10272, and 10294, were synthesized in the same way.

Synthesis of the phenol-containing compound, 10045, was described in U.S. Pat. No. 8,420,680. Other phenol-containing compounds, including NP10030, 10039, 10040, 10052, 10082, 10171, 10235, 10243, 10244, 10245, 10247, and 10249 were synthesized in the same way.

Synthesis of the benzimidazolinone-containing compound, 10146, was described in U.S. Pat. No. 8,420,680. Other fused-ring (bicyclic) compounds, such as 10228, were synthesized in the same way.

B. Chemical Characterizations

NP10679: $^1$H NMR (400 MHz, DMSO-$d_6$): δ 9.90 (brs, 1H), δ 7.50 (d, J=16 Hz, 1H), 7.05 (d, J=16 Hz, 1H), 6.85-6.70 (m, 3H), 4.90 (brd, 1H), 4.00-3.80 (m, 3H), 3.30-3.20 (m, 4H), 2.90-2.75 (m, 2H), 2.70-2.30 (m, 8H). $^{13}$C NMR (75 MHz, CDCl3): δ 171.82, 154.63, 153.09, 131.21, 130.04, 126.36, 124.94, 122.87, 121.22, 120.79, 120.36, 119.92, 116.30, 114.52, 113.95, 113.24, 70.70, 65.80, 60.48, 53.02, 47.98, 30.51, 25.58. m/z calculated for $C_{23}H_{26}F_3N_3O_3$ 500.47; found 500.30 [M+H].

Example 2. Measurement of the GluN2B Potency and pH Dependence

A. Materials and Methods

The GluN2B potency and pH dependence of NP10679, NP10309, and other compounds in Tables 1 and 2 were evaluated on human GluN1-la/GluN2B receptors (hereafter GluN1/GluN2B) expressed in *Xenopus laevis* oocytes by measuring the $IC_{50}$ values at pH 6.9 and 7.6, respectively.

Two Electrode Voltage-Clamp Recordings from *Xenopus laevis* Oocytes

Stage V-VI *Xenopus laevis* unfertilized oocytes were purchased from Ecocyte (Austin, Texas) and injected with 5 ng of GluN1 and 10 ng of GluN2B cRNAs. The cDNAs for human GluN1 and GluN2B, encoding NCBI reference sequences NM_007327.3 and NM_000834.3, respectively, were linearized and cRNAs made as previously described (Traynelis et al., *J Neurosci,* 1998, 18(16):6163-75). After injection, the oocytes were incubated in Barth's culture solution (88 mM NaCl, 1 mM KCl, 2.4 mM $NaHCO_3$, 10 mM HEPES, 0.82 mM $MgSO_4$, 0.33 mM $Ca(NO_3)_2$, 0.41 mM $CaCl_2$), 10 U/mL PenStrep, and 0.1 mg/mL gentamycin, pH 7.4) at 18° C. Two electrode voltage-clamp (TEVC) recordings were made at 22-23° C., 2-7 days after the injection, using Warner OC725C amplifiers ($V_{HOLD}$=−40 mV). Briefly, the oocytes were perfused in a recording solution (90 mM NaCl, 1 mM KCl, 10 mM HEPES, 0.01 mM EDTA, and 0.5 mM $BaCl_2$) adjusted to either pH 7.6 or 6.9 by addition of NaOH or HCl, respectively (pH 6.9 solutions were prepared by addition of HCl to pH 7.6 solutions to maintain an equal concentration of $Na^+$ ions in both solutions). Concentration-response curves of the compounds were obtained by application of increasing concentrations of each individual compound until steady state conditions were obtained, in the presence of saturating agonist concentrations (i.e., 100 μM glutamate and 30 μM glycine). In general, oocyte recordings were made from 4-10 oocytes per experiment (i.e., oocyte injection cycle) from ≥two experiments. The concentration-response relationship for each oocyte was fit by equation (1), $$\text{Percent Response}=(100-\text{minimum})/(1+([\text{concentration}]/IC_{50})^{nH})+\text{minimum} \quad (1)$$

where minimum is the residual response in saturating concentration of each individual compound (constrained to be ≥0), and $IC_{50}$ is the concentration of compound that causes half-maximal inhibition, and nH is the Hill slope.

For NP10679, activity was also tested at GluN2A (NM_000833), GluN2C (NM_000835), and GluN2D (NM_000836) NMDAR in a similar manner as for GluN2B, except that NP10679 was tested at a single concentration of 3 μM.

B. Results

The $IC_{50}$ values of the compounds against GluN2B measured at pH 6.9 and 7.6 are shown in Tables 1 and 2.

Table 1 shows the $IC_{50}$ values against GluN2B for nine pairs of enantiomers. Among these compounds, the R enantiomers exhibited much lower pH boost compared to their corresponding S enantiomers. Here, the pH boost of a specific compound is defined as the ratio of its $IC_{50}$ value determined at pH 7.6 to its $IC_{50}$ value determined at pH 6.9.

In Table 1, some R enantiomers, such as 10233, 10249, and 10228 exhibited lower potency (i.e., higher $IC_{50}$) against GluN2B compared to their corresponding S enantiomers, whereas other R enantiomers exhibited comparable or higher potency against GluN2B compared to their corresponding S enantiomers.

TABLE 1

Activity against GluN2B for nine pairs of enantiomers

| Compound | Chirality | $IC_{50}$ (μM) pH 6.9 | $IC_{50}$ (μM) pH 7.6 | pH Boost |
|---|---|---|---|---|
| 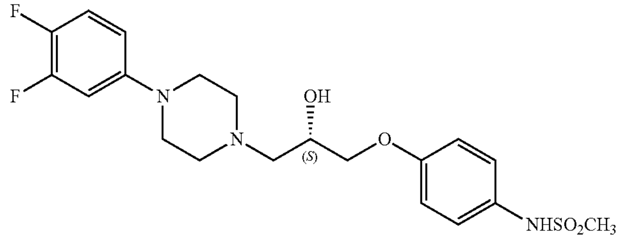 (93-108) | S | 0.031 | 0.558 | 18.0 |
| 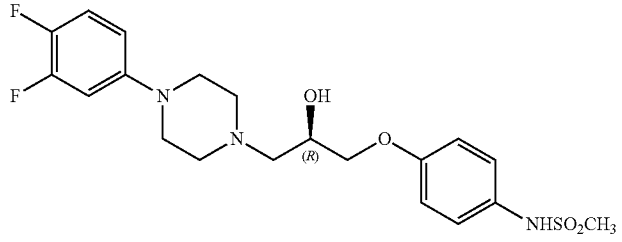 (10233) | R | 0.047 | 0.294 | 6.3 |
| 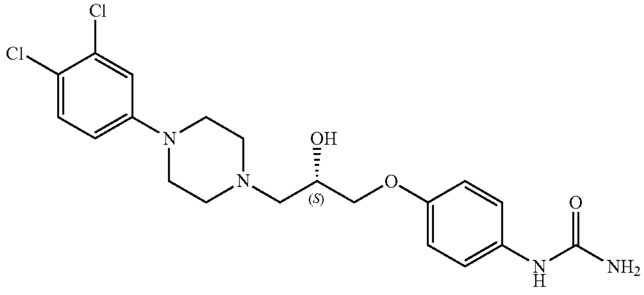 (10131) | S | 0.103 | 0.947 | 9.2 |

TABLE 1-continued
Activity against GluN2B for nine pairs of enantiomers
| Compound | Chirality | $IC_{50}$ (μM) pH 6.9 | $IC_{50}$ (μM) pH 7.6 | pH Boost |
|---|---|---|---|---|
| 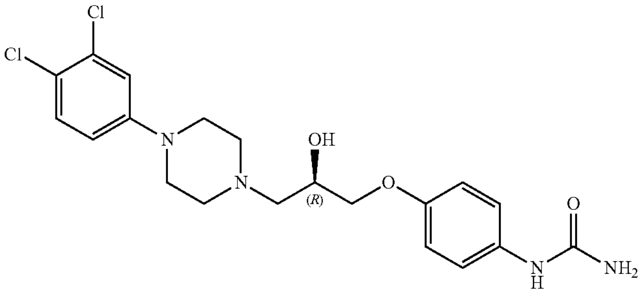 (10166) | R | 0.030 | 0.132 | 4.4 |
| 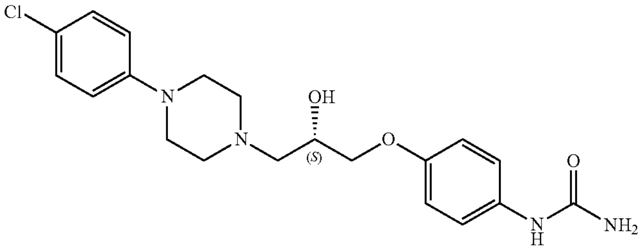 (10075) | S | 0.046 | 0.452 | 9.8 |
| 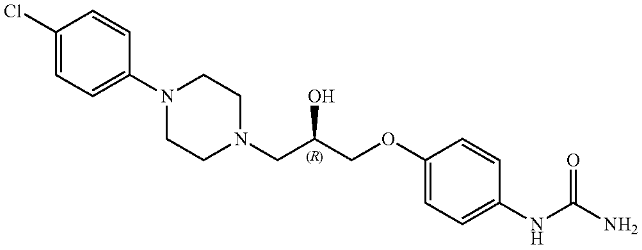 (10165) | R | 0.019 | 0.060 | 3.2 |
| 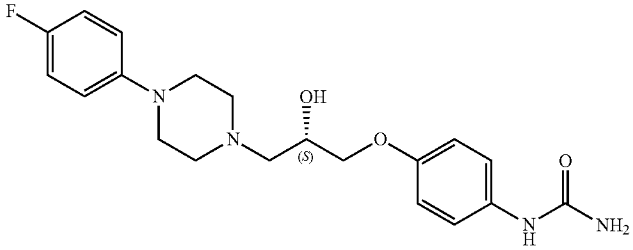 (10214) | S | 0.221 | 2.180 | 9.9 |
| 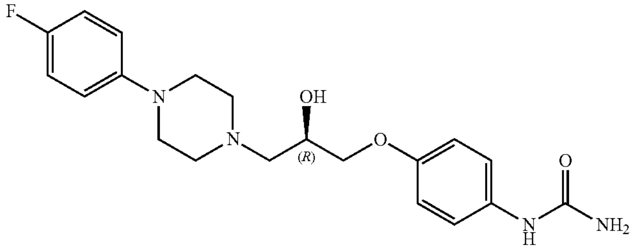 (10225) | R | 0.097 | 0.527 | 5.4 |

TABLE 1-continued
Activity against GluN2B for nine pairs of enantiomers
| Compound | Chirality | $IC_{50}$ (μM) pH 6.9 | $IC_{50}$ (μM) pH 7.6 | pH Boost |
|---|---|---|---|---|
| 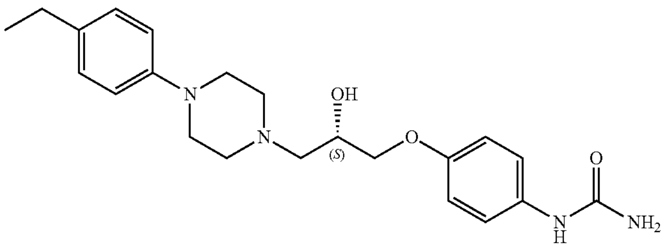 (10189) | S | 0.094 | 1.000 | 10.6 |
| 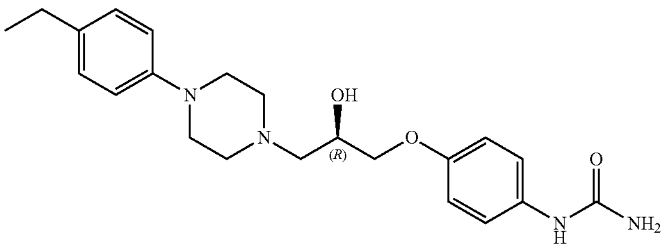 (10222) | R | 0.052 | 0.183 | 3.5 |
| 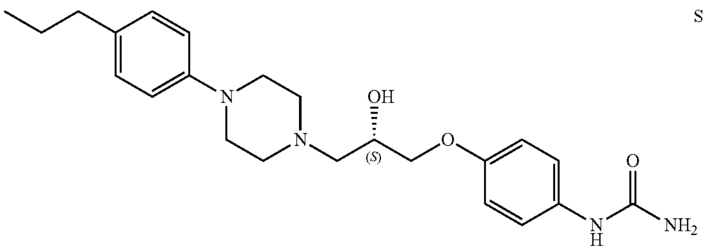 (10215) | S | 0.130 | 1.300 | 10.0 |
| 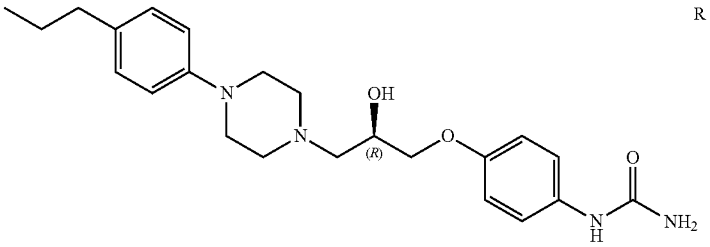 (10224) | R | 0.034 | 0.171 | 5.0 |
| 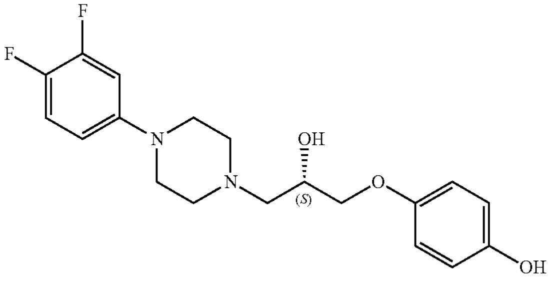 (10030) | S | 0.087 | 0.978 | 11.2 |

TABLE 1-continued
| Activity against GluN2B for nine pairs of enantiomers | | | | |
|---|---|---|---|---|
| Compound | Chirality | $IC_{50}$ (μM) pH 6.9 | $IC_{50}$ (μM) pH 7.6 | pH Boost |
| 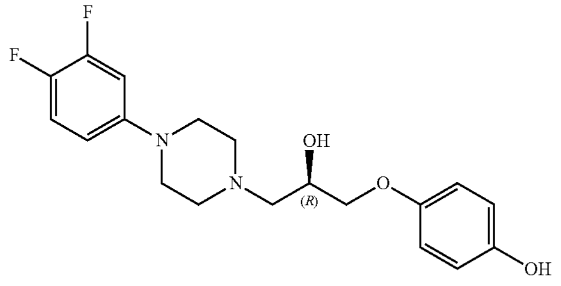 (10052) | R | 0.050 | 0.272 | 5.4 |
| 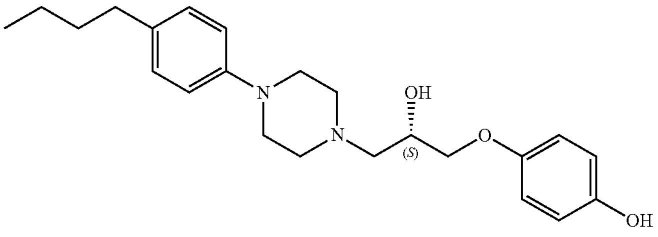 (10235) | S | 0.398 | 4.380 | 11.0 |
| 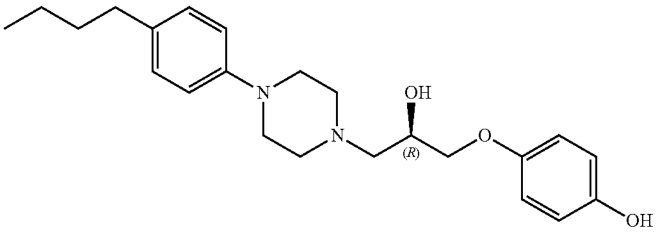 (10249) | R | 0.549 | 3.420 | 6.2 |
| 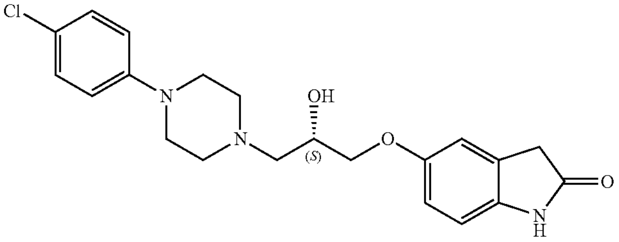 (10146) | S | 0.029 | 0.370 | 12.8 |

TABLE 1-continued

Activity against GluN2B for nine pairs of enantiomers

| Compound | Chirality | $IC_{50}$ (μM) pH 6.9 | $IC_{50}$ (μM) pH 7.6 | pH Boost |
|---|---|---|---|---|
| 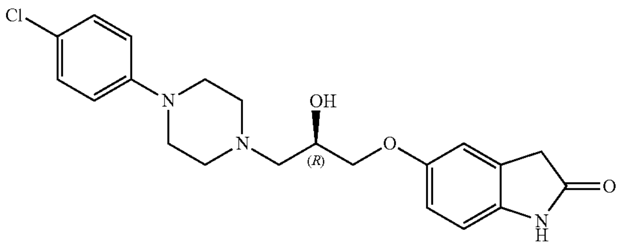 (10228) | R | 0.121 | 0.592 | 4.9 |

$IC_{50}$ values for inhibition of human GluN1/GluN2B expressed in *Xenopus* oocytes were determined as described in the "Materials and methods" section above from composite inhibition curves. The pH boost was calculated as the ratio of the $IC_{50}$ value at pH 7.6 to the $IC_{50}$ value at pH 6.9.

Table 2 shows the $IC_{50}$ values against GluN21B for six pairs of enantiomers. Among these compounds, the structure-activity relationship is very different than that obtained from Table 1. Notably, the R enantiomers exhibited comparable or even higher pH boost compared to their corresponding S enantiomers. Moreover, every R enantiomer exhibited comparable or higher potency against GluN21B than its corresponding S enantiomer.

For example, NP10679 exhibited an $IC_{50}$ value of 23 nM at pH 6.9 and an $IC_{50}$ value of 142 nM at pH 7.6, corresponding to a pH boost of 6.2. In comparison, its S enantiomer, NP10309, exhibited an $IC_{50}$ value of 111 nM at pH 6.9 and an $IC_{50}$ value of 717 nM at pH 7.6, corresponding to a pH boost of 6.5.

TABLE 2

Activity against GluN2B for six pairs of enantiomers

| Compound | Chirality | $IC_{50}$ (μM) pH 6.9 | $IC_{50}$ (μM) pH 7.6 | pH Boost |
|---|---|---|---|---|
| 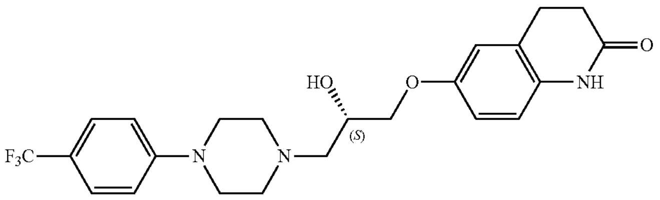 (NP10309) | S | 0.111 | 0.717 | 6.5 |
| 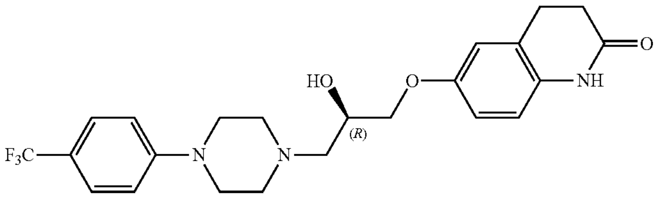 (NP10679) | R | 0.023 | 0.142 | 6.2 |
| 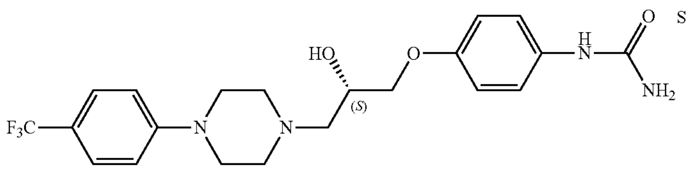 (10294) | S | 0.030 | 0.209 | 7.0 |

TABLE 2-continued
Activity against GluN2B for six pairs of enantiomers
| Compound | Chirality | $IC_{50}$ (μM) pH 6.9 | $IC_{50}$ (μM) pH 7.6 | pH Boost |
|---|---|---|---|---|
| 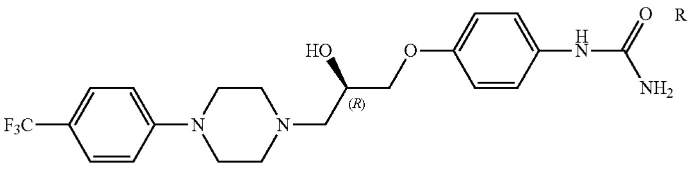 (10272) | R | 0.022 | 0.128 | 5.8 |
| 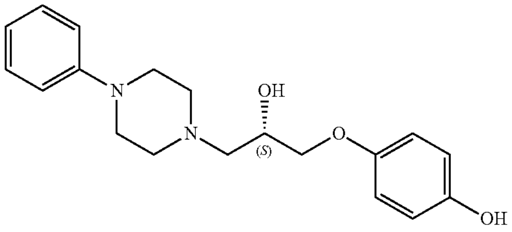 (10039) | S | 0.217 | 0.476 | 2.2 |
| 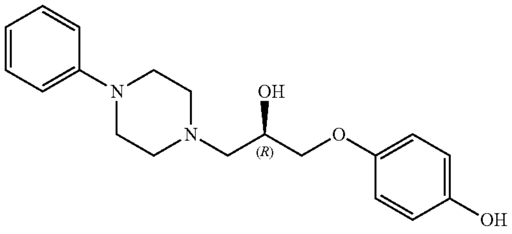 (10243) | R | 0.071 | 0.574 | 8.1 |
| 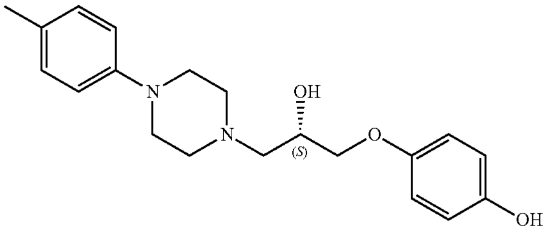 (10040) | S | 0.074 | 0.260 | 3.5 |
| 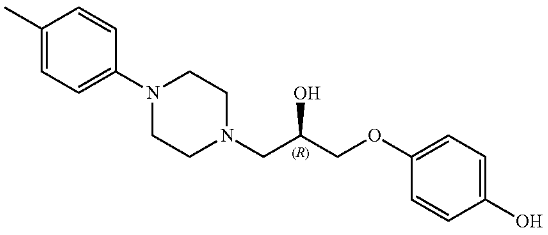 (10244) | R | 0.047 | 0.305 | 6.5 |

TABLE 2-continued

| Activity against GluN2B for six pairs of enantiomers | | | | |
|---|---|---|---|---|
| Compound | Chirality | $IC_{50}$ (μM) pH 6.9 | $IC_{50}$ (μM) pH 7.6 | pH Boost |
| 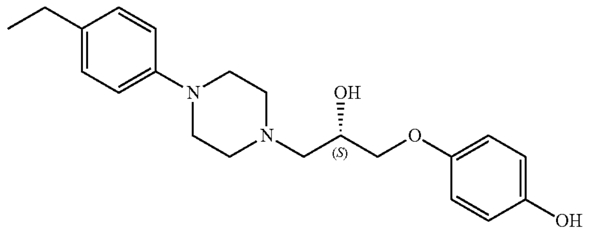 (10171) | S | 0.046 | 0.316 | 6.9 |
| 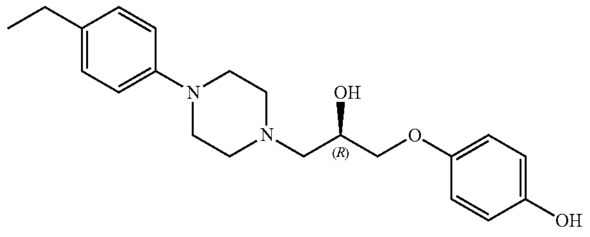 (10245) | R | 0.025 | 0.385 | 15.4 |
| 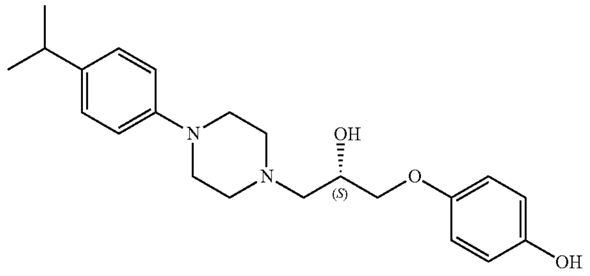 (10082) | S | 0.356 | 1.370 | 3.8 |
| 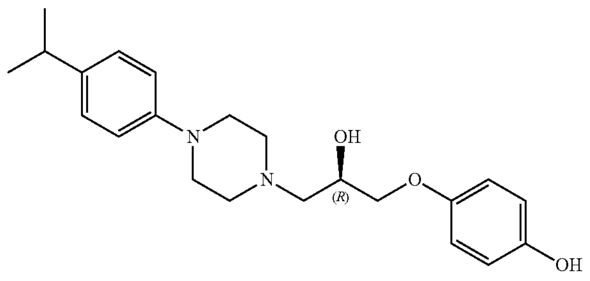 (10247) | R | 0.144 | 0.675 | 4.7 |

$IC_{50}$ values for inhibition of human GluN1/GluN2B expressed in *Xenopus* oocytes were determined as described in the "Materials and methods" section above from composite inhibition curves. The pH boost was calculated as the ratio of the $IC_{50}$ value at pH 7.6 to the $IC_{50}$ value at pH 6.9.

Furthermore, the activity of NP 10679 against GluN2A, GluN2C, and GluN2D were measured at pH 6.9. NP10679 is highly selectivity for the GluN21B subunit over GluN2A, GluN2C, and GluN2D. There was no noticeable off-target inhibition against GluN2A, GluN2C, and GluN2D at 3 μM (Table 3).

TABLE 3

Activity of NP10679 against GluN2A, GluN2C, and GluN2D

| Compound | GluN2A % residual[A] | GluN2C % residual[A] | GluN2D % residual[A] |
|---|---|---|---|
| NP10679 | 99.0 (pH 6.9) | 100.1 (pH 6.9) | 98.3 (pH 6.9) |

[A]Values are % current remaining after application of 3 μM compound and were the mean of ≥4 oocytes recorded at pH 6.9 or 7.4.

Example 3. In Vitro Drug Profiling

A. Materials and Methods

Liver Microsome Stability, Cytochrome P450 Inhibition, and Plasma Protein Binding Metabolic stability was assessed using human and mouse liver microsomes (Xenotech, USA). The final composition of the assay included 1 μM of the test compound or reference standards (imipramine and diclofenac sodium) prepared from DMSO or acetonitrile stock, so that the final concentration of DMSO and acetonitrile was 0.2% and 0.8%, respectively. The test compound was incubated with 0.5 mg/mL microsomal protein without (100 mM potassium phosphate buffer alone, pH 7.4) or with cofactors (5.0 mM glucose-6-phosphate, 0.06 U glucose-6-phosphate dehydrogenase, 2.0 mM $MgCl_2$, 1.0 mM $NADP^+$/NADPH). The test compound and standards were incubated at 37° C. with human and mouse liver microsomes; aliquots of the reaction mixture (100 μL) were removed at 0, 5, 15, 30, 60 and 120 min. The reaction in the aliquots was stopped by the addition of 2.5 mL tert-butyl methyl ether and the samples were subjected to shaking for 15 min. Afterwards, the samples were spun at 4000 rpm for 15 min at 10° C. and the organic phase evaporated to dryness, then reconstituted with solvent for LC-MS/MS analysis. The percent of the test compound remaining after the specified incubation period was calculated with respect to the peak areas of the test compound at time 0 min.

Inhibition of CYP2D6 and CYP3A4 was accomplished using recombinant human isoforms and a Vivid CYP blue screening kit (Invitrogen, USA) by incubating 2-fold serial dilutions (9 samples) of the test compound with kit reagents and reaction buffer according to the manufacturer's methods in a 96-well plate. The plate was then incubated at room temperature for 30 min before fluorescence was measured with a plate reader. For these studies, reference standards ketoconazole (CYP3A4) and quinidine (CYP2D6) were used as controls.

Plasma protein binding was performed with a rapid equilibrium dialysis (RED) device containing dialysis membrane with a molecular weight cut-off of 8,000 Daltons according to the manufacturer's instructions (ThermoFisher, USA). The plasma samples (pH 7.4) and the test compound solution (1 or 5 μM) or reference standards (Warfarin and Propranolol, 10 μM) were combined (DMSO final conc 0.1%). 300 μL of this spiked plasma sample was added to the sample chamber, and 500 μL of blank PBS buffer (pH 7.4) was added into the buffer chamber. The RED device was sealed with adhesive film and then incubated at 37° C. with shaking at 300 rpm for 4 h. Following incubation, an aliquot (50 μL) was removed from each well (spiked plasma and buffer side) and diluted with equal volume of the corresponding opposite matrix (blank buffer or blank plasma) to nullify the matrix effect, and then extracted for analysis by LC-MS/MS. The amount of free material was determined by:

% Free=(LC-MS/MS peak area of test compound in buffer side/LC-MS/MS peak area of test compound in plasma side)×100%

Off-Target Screening

The in vitro effects of NP10679 on the hERG (human ether-à-go-go-related gene) potassium channel current (a surrogate for IKr, the rapidly activating, delayed rectifier cardiac potassium current) were evaluated at room temperature in HEK mammalian cells stably expressing hERG, using the QPatch HT® (Sophion Bioscience A/S, Denmark) and an automatic parallel patch clamp system (ChanTest, Cleveland, OH). NP10679 was evaluated at 0.1, 0.3, 1 and 3 μM diluted in HB-PS solution composed of (in mM): NaCl, 137; KCl, 4.0; $CaCl_2$), 1.8; $MgCl_2$, 1; HEPES, 10; glucose, 10; pH adjusted to 7.4. Each test concentration was tested in two or more cells (n≥2). Duration of exposure to each test article concentration was 3 minutes. A positive control (0.5 μM E-4301) was used to confirm the sensitivity of the cells to an hERG inhibitor.

Off-target radioligand binding displacement studies of NP10679 was conducted at the National Institutes of Mental Health Psychoactive Drug Screening Program (NIMH PDSP) at the University of North Carolina at Chapel Hill. Briefly, the compound was submitted to the NIMH PDSP and screened at a single concentration (10 μM) of test article under equilibrium conditions for ability to displace specific radioligands from binding to their targets expressed in mammalian cell membranes in vitro. Each receptor target was assayed in quadruplicate and the % inhibition of radioligand binding at each target determined at pH 7.4. If the % inhibition was >50%, a full competition displacement binding study was conducted to determine an $IC_{50}$ value and from this a $K_i$ value using the Cheng-Prusoff equation ($K_i=IC_{50}/[1+(L/K_d)]$) in which L is the radioligand concentration used in the competition binding assay and $K_d$ is the radioligand equilibrium binding affinity determined in the saturation binding assays above.

The following targets (with radioligand in parentheses) were tested: 5-HT1A ([$^3$H]8-OH-DPAT), 5-HT1B ([$^3$H]5-carboxamidotryptamine), 5-HT1D ([$^3$H]5-carboxamidotryptamine), 5-HT1E ([$^3$H]5HT), 5-$HT_{2A}$ ([$^3$H]Ketanserin), 5-HT2B ([$^3$H]LSD), 5-HT2C ([$^3$H]Mesulergine), 5-HT3 ([$^3$H]LY278584), 5-HT5A ([$^3$H]LSD), 5-HT6 ([$^3$H]LSD), 5-HT7 ([$^3$H]LSD), Alpha1A ([$^3$H]Prazosin), Alpha1B ([$^3$H]Prazosin), Alpha1D ([$^3$H]Prazosin), Alpha2A ([$^3$H]-Rauwolscine), Alpha2B ([$^3$H]-Rauwolscine), Alpha2C ([$^3$H]-Rauwolscine), Beta1 ([$^{125}$I]Pindolol), Beta2 ([$^3$H]CGP12177), Beta3 ([$^3$H]CGP12177), BZP Rat Brain Site ([$^3$H]Flunitrazepam), D1 ([$^3$H]SCH23390), D2 ([$^3$H]N-Methylspiperone), D3 ([$^3$H]N-Methylspiperone), D4 ([$^3$H]N-Methylspiperone), D5 ([$^3$H]SCH23390), DAT ([$^3$H]WIN35428), DOR ([$^3$H]DADLE), GABAA ([$^3$H]Muscimol), H1 ([$^3$H]Pyrilamine), H2 ([$^3$H]Tiotidine), H3 ([$^3$H]Alpha-methylhistamine), H4 ([$^3$H]Histamine), KOR ([$^3$H]U69593), M1 ([$^3$H]QNB), M2 ([$^3$H]QNB), M3 ([$^3$H]QNB), M4 ([$^3$H]QNB), M5 ([$^3$H]QNB), MOR ([$^3$H]DAMGO), NET ([$^3$H]Nisoxetine), PBR ([$^3$H]PK11195), SERT ([$^3$H]Citalopram), Sigma 1 ([$^3$H]Pentazocine(+)), and Sigma 2 ([$^3$H]DTG).

Some receptor targets were also tested in functional studies to establish if NP10679 acted as an agonist or an antagonist. These receptor targets include the 5-$HT_{2A}$ receptor, the functional study of which was performed at pH 7.4 (Porter, et al., *Br J Pharmacol,* 1999, 128:13-20; CEREP, France). To evaluate agonism, HEK293 cells transfected with human 5-$HT_{2A}$ were incubated with increasing concentrations of NP10679 (duplicate wells/concentration) at 37° C. for 30 min. Activation of the receptor was determined by changes in IP1 levels detected by the HTRF® method. Separate wells stimulated with 10 μM serotonin served as a positive control. To determine antagonism by NP10679, the cells were incubated with increasing concentrations of the compound (duplicate wells per concentration) at 37° C. for 30 min. The cells were stimulated with 100 nM serotonin. Activation of the receptor was determined by changes in IP1 levels detected by the HTRF® method. A control inhibitor, ketanserine, was run separately to confirm the accuracy and reliability of the assay data.

Similar studies were performed to evaluate agonism and antagonism in CHO cells transfected with human $\alpha_{1A}$-adrenergic receptors incubated with increasing concentrations of NP10679 (duplicate wells per concentration) at room temperature at pH 7.4 (Vicentic, et al., *J Pharmacol Exp Ther,* 2002, 302:58-65). Activation of the receptor was determined by changes in intracellular [$Ca^{2+}$] by a fura-2 fluorimetry detection method (CEREP, France). Separate wells were stimulated with 30 nM epinephrine as a positive control. To evaluate antagonism, the cells were incubated with increasing concentrations of NP10679 (duplicate wells/concentration) at room temperature and then the cells were stimulated with 3 nM epinephrine. Activation of the receptor was determined by changes in intracellular [$Ca^{2+}$] by a fura-2 fluorimetry detection method (CEREP, France).

To evaluate agonism and antagonism at the human $H_1$-histamine receptor, HEK293 cells transfected with $H_1$ receptors were incubated with increasing concentrations of NP10679 (duplicate wells per concentration) at pH 7.4 at room temperature (Miller, et al., *J Biomol Screen,* 1999, 4(5):249-258). Activation of the receptor was determined by changes in intracellular [$Ca^{2+}$] by a fura-2 fluorimetry detection method. Separate wells stimulated with 10 μM histamine as a positive control. To evaluate antagonism by NP10679, the cells were incubated with increasing concentrations of the compound (duplicate wells per concentration) at room temperature and then the cells were stimulated with 300 nM histamine. Activation of the receptor was determined by changes in intracellular [$Ca^{2+}$] by a fura-2 fluorimetry detection method. A control inhibitor, pyrilamine, was run separately to confirm the accuracy and reliability of the assay data (CEREP, France).

B. Results

Metabolic stability was carried out using human and mouse liver microsomes with 1 μM NP10679 prepared from DMSO stock (DMSO 0.2% final). The compound and standards were incubated with human and mouse liver microsomes with or without cofactors, and the samples were extracted and analyzed using LC-MS/MS, as described above. NP10679 exhibited excellent stability in both human and mouse liver microsomes such that 72% of NP10679 remained in incubations with human microsomes and 54% remained in incubations with mouse liver microsomes in the presence of the cofactors after a one-hour incubation at 37° C.

Moreover, NP10679 at 1 μM did not inhibit human recombinant cytochrome 450 isoforms CYP3A4 or CYP2D6.

Further, NP10679 bound to human, mouse, and dog plasma proteins at 97.7% (n=2), 98.2% (n=2), and 98.2% (n=1), respectively.

NP10679 was also tested at 10 μM for binding to 41 neurotransmitter receptors, enzymes, and channels via displacement of a radioligand in competitive receptor binding assays. Targets for which 10 μM NP10679 displaced >50% of the radioligand were followed up with full dose-effect displacement studies, which identified sub-micromolar $K_i$ values for five of these targets, the 5-$HT_{2A}$ serotonin receptor (0.638 μM), the $\alpha_{1A}$ (0.603 μM) and $\alpha_{1D}$ (0.495 μM) adrenergic receptors, the $H_1$ histamine receptor (0.040 μM), and the serotonin transporter SERT (0.135 μM). See Table 4. Three receptors (5-$HT_{2A}$, $\alpha_{1A}$ adrenergic, and $H_1$ histamine) were also tested for functional agonism and antagonism; in all cases, the compound behaved as an antagonist (Table 4). Inhibition of the human delayed rectifier cardiac potassium current channel (hERG channel) was measured in mammalian HEK cells transfected with the hERG potassium channel cDNA via patch-clamp electrophysiology across four concentrations of NP10679, which revealed an $IC_{50}$ for inhibition of 0.617 μM (Table 4).

TABLE 4

Potency of NP10679 at Off-Target Proteins

| Target | $K_i$ (μM) | Functional $IC_{50}$ (μM) |
|---|---|---|
| 5-HT1B | >10 | nd |
| 5-HT1D | 2.29 | nd |
| 5-HT2A | 0.638 | 1.71 |
| 5-HT2B | 1.92 | nd |
| Alpha1A | 0.603 | 0.154 |
| Alpha1B | 1.92 | nd |
| Alpha1D | 0.495 | nd |
| Alpha2C | 3.09 | nd |
| H1 | 0.040 | 0.073 |
| SERT | 0.135 | nd |
| Sigma 2 | 1.98 | nd |
| hERG | nd | 0.617 |

All assays were conducted at pH 7.4; "nd": not done.

Example 4. In Vivo Efficacy and Pharmacokinetic Studies

A. Materials and Methods

Formulation and Drug Dosing

For MCAO, locomotor, and rotarod studies, NP10679, MK-801, and ifenprodil were formulated in 2% or 10% N',N'-dimethylacetamide, 10% propylene glycol, and 30% 2-hydroxypropyl-beta-cyclodextrin in water, with a dose volume of 10 mL/kg and administered via the intraperitoneal (IP) route. Formulation for pharmacokinetic studies used 2% or 10% N',N'-dimethylacetamide, 10% propylene glycol, and 30% 2-hydroxypropyl-beta-cyclodextrin in water and a dose volume of 10 mL/kg (all routes of administration).

In Vivo Model of Transient Focal Ischemia

All protocols involving animals were approved by the Georgia State University IACUC, an AAALAC accredited program, and was under the supervision of a licensed veterinarian. Mice were group housed, provided nestlets and shelters with access to food pellets and water ad libitum under a 12-hour light/dark cycle. Mice were brought to a separate room and housed for at least 30 min prior to initiation of the surgery.

Mice (C57B16, >90 days old, Jackson Labs) were subjected to transient (60 min) middle cerebral artery occlusion (MCAO) and the infarct volume measured 24 hours post reperfusion, similar as previously described (Yuan, et al., *Neuron,* 2015, 85(6):1305-1318). Male mice were used for this experiment to reduce potential confound by progesterone variation through estrous cycles, which can have neuroprotective actions. Briefly, transient ischemia was induced in anesthetized (2% isoflurane/98% $O_2$) mice by insertion of an intraluminal suture into the MCA for 60 minutes (Junge, et al., *Proc Natl Acad Sci USA,* 2003, 100: 13019-13024). The body temperature of each mouse was monitored with a rectal thermometer and maintained at 37° C. through use of a homeothermic blanket. Changes in local cerebral blood flow were monitored with a laser Doppler flowmeter probe (Perimed) secured via glue to the skull 4-6 mm lateral and 2 mm posterior of bregma. An 11-mm 5-0 Dermalon or Look (SP185) black nylon non-absorbable suture with the tip flame-rounded was introduced into the left internal carotid artery through the external carotid artery stump up to 10.5-11 mm of suture insertion. Only mice with a reduction in blood flow to <20% for 60 min and with recovery of blood flow to >90% following removal of the suture were progressed to complete the study. Following the occlusion period, mice were placed back in their cages on a warming blanket (37° C.) for several hours and monitored for righting reflex and ability to ambulate upon a gentle touch. At 24 hours post occlusion, mice were euthanized by isoflurane overdose, the brain quickly removed and cut into 2 mm sections and incubated in 2% 2,3,5-triphenyltetrazolium chloride (TTC) in phosphate buffered saline (pH 7.4) at 37° C. for 20 min, then placed at 4° C. for imaging. The infarct area was then measured using the NIH IMAGE software (Scion Corporation, Beta 4.0.2 release). The lesioned area of each section was determined by digital threshold reductions in TTC staining to ≤20% lower intensity than that observed in the contralateral cortex. The infarct region was then manually outlined with a curser and the cubic volume of the infarct determined for each slice, then summed across all four slices from each animal to obtain total infarct volume. A ratio of the contralateral to ipsilateral hemisphere volume was multiplied by the corresponding infarct section volume to correct for edema. Drug was administered by IP injection 5 min prior to initiation of surgery (approximately 15 min prior to vessel occlusion). All drug doses were randomized, and investigator(s) blinded throughout the study from surgical procedure through analysis of stained sections to measurement of infarct volume.

Statistics

Based on historical variability and an anticipated effect size of 45-50%, we estimated that n=12 per group (4 groups per study) were adequate to detect significant effects ($\alpha$=0.05) with sufficient power, ($\beta$=0.90) (G*Power 3.1). The infarct volume following administration of a drug dose was compared to the vehicle control by one-way ANOVA and Dunnett's tests ($p<0.05$).

Pharmacokinetic Studies

Pharmacokinetic studies on NP10679 were outsourced to Anthem Biosciences (Bangalore, India), and were performed after obtaining the Institutional Animal Ethics Committee (IAEC) permission in accordance with the CPCSEA guidelines.

Evaluation of NP10679 properties was performed in male BALB/c mice (8-10 weeks old, 20-30 g). Briefly, mice were administered a 2 mg/kg or a 5 mg/kg dose (n=3 each) by IP injection (10 mL/kg dose volume) and blood samples collected at 0.08, 0.25, 0.5, 1, 2, 4, 8 and 24 hours post dose in tubes containing sodium heparin on ice. 100 μL of plasma was combined with 50 μL of internal standard (haloperidol, 10 μg/mL) and tubes were then spun at 4000 g for 10 min (4° C.) and plasma transferred to clean tubes and stored at −80° C. until analysis. The analyte NP10679 was quantified with an API 3200 Q-trap LC-MS/MS and compared to standards and data analyzed by WinNonlin 6.3 (Pharsight).

In a separate study, BALB/c mice were administered either with an oral dose (10 mg/kg) or an intravenous dose (3 mg/kg) of NP10679 (10 mL/kg injection volume). Blood samples were collected on ice in sodium heparin tubes at 0.08, 0.25, 0.5, 1, 2, 4, 8, and 24 hours post dose. Samples were prepared and analyzed as described above except here the internal standard was fluconazole (10 μg/mL).

NP10679 was also measured in the brain compartment compared to blood at 0.25 and 1 hour post 3 mg/kg IV dosing in two separate studies with blood samples collected and prepared as described above. Here, brain samples were first washed in deionized water to remove blood, the weight recorded, then transferred into fresh 1 mL water, homogenized, and stored at −80° C. until analysis. The ratio of compound in brain (g) compared to blood (mL) was then calculated.

B. Results

Prior generations of non-selective NMDAR inhibitors that blocked all NMDARs regardless of subunit composition produce both off- and on-target adverse effects, which complicated or aborted clinical development. The most prominent side effects reported included motor dysfunction, cognitive impairment, and psychotomimetic effects such as hallucinations and disorganized thought (Lees, et al., *Lancet,* 2000, 355:1949-1954; Sacco, et al., *JAMA,* 2001, 285:1719-1728; Diener, et al., *J Neurol,* 2002, 249:561-568; Rowland, Aviat Space Environ Med, 2005, 76:C52-C58; Blagrove, et al., *Psychopharmacol,* 2009, 203:109-120). Although GluN2B-selective NMDAR negative allosteric modulators appear to be tolerated better than competitive antagonists or channel blockers, they still can exhibit side effects (Chaperon, et al., *Behav Pharmacol,* 2003, 14:477-487; DeVry and Jentzsch, *Behav Pharmacol,* 2003, 14:229-235; Yurkewicz, et al., *J Neurotrauma,* 2005, 22:1428-1443; Nicholson, et al., *Behav Pharmacol,* 2007, 18:731-743; Preskorn, et al., *J Clin Psychopharmacol,* 2008, 28:631-637; Nutt, et al., *Mov Disord,* 2008, 23: 1860-1866).

In the MCAO experiments, NP10679 was administered prior to transient ischemia induced by occlusion of the middle cerebral artery. Vehicle-treated mice exhibited substantial neuronal cell death with a 101±8.7 $mm^3$ infarct volume after 60 min of transient ischemia. By comparison, infarct volume was reduced in a dose-dependent manner by NP10679 with an $ED_{50}$ of 1 mg/kg IP dose and a maximum infarct volume reduction of 52% (FIG. 1). Both the 5 mg/kg (56±6.6 $mm^3$) and 10 mg/kg (49±3.0 $mm^3$) doses significantly reduced infarct volumes compared to the vehicle control (FIG. 1).

Figure 2A:
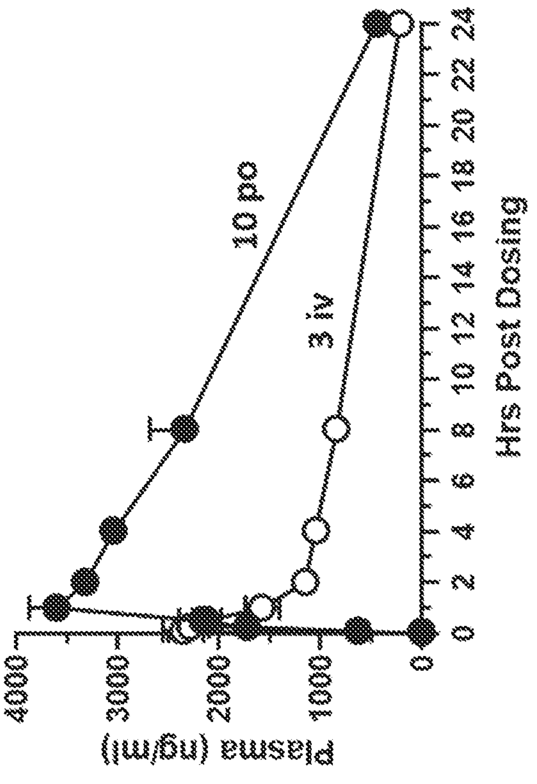
FIG. 2A is graph showing the total plasma levels (ng/mL) of an exemplary compound (NP10679) plotted against time (hour), following a 10 mg/kg oral dose (black symbols) or a 3 mg/kg IV dose (open symbols) in mice. Data are shown in mean±SEM (n=3 per data point).

In pharmacokinetic studies mice were dosed with a solution orally (10 mg/kg) or via IV injection (3 mg/kg) to determine both oral bioavailability and plasma pharmacokinetics for NP10679 (FIG. 2A, Table 5). The plasma terminal half-life for the oral route was 7.06 hours and for IV administration was 8.56 hours, with a high volume of distribution of 1.59 L/kg and clearance of 2.44 mL/min/kg, and high oral bioavailability (75.7%). See Table 5.

Figure 2B:
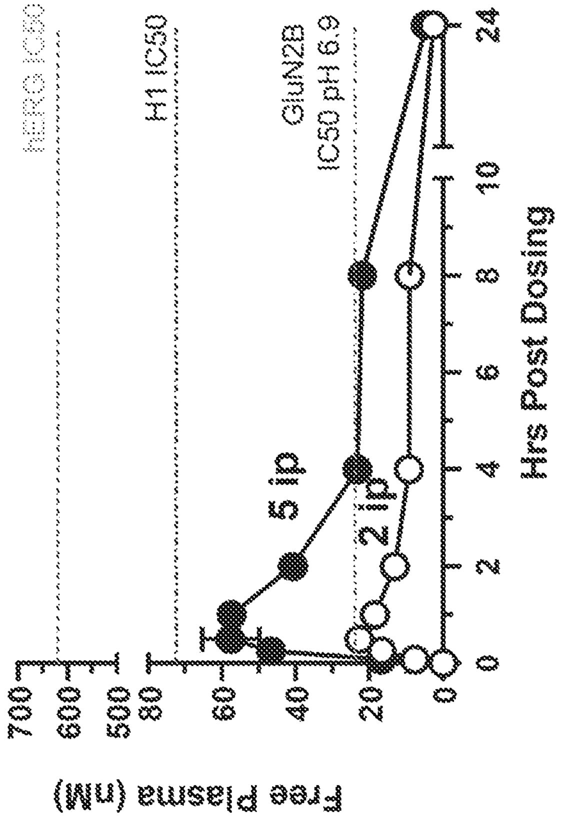
FIG. 2B is a graph showing free plasma levels (nM) of an exemplary compound (NP10679) plotted against time (hour), following a 2 mg/kg (open symbols) or a 5 mg/kg (black symbols) IP dose in mice. Data are shown in mean±SEM (n=3 per data point). The $IC_{50}$ of NP10679 against GluN2B at pH 6.9, the functional $IC_{50}$ against H1 histamine receptors, and the functional $IC_{50}$ against hERG are indicated in the graph as dotted lines.

In a separate study, mice were dosed IP with 2 and 5 mg/kg of NP10679 to provide drug disposition information in mice following the same dose and route of administration as used in the MCAO neuroprotection studies. Here, NP10679 displayed a dose-dependence with peak levels of 581 and 1431 ng/mL in plasma 30 min post dosing, respectively, and with plasma half-lives of 7.5 to 9.9 hours (Table 5). Thus, a single IP administration of NP10679 provided ample exposures to drive neuroprotection over a large fraction of the 24-hour post ischemia period. FIG. 2B shows the calculated free plasma levels (unbound drug) at both the 2 and 5 mg/kg IP doses, demonstrating that free drug levels after 5 mg/kg dose were above the $IC_{50}$ against GluN2B at pH 6.9. The free plasma levels of NP10679 were calculated based on the free drug fraction determined by the plasma binding studies described above.

Further, the pharmacokinetics studies in the brain compartment show that NP10679 exhibited high brain penetration, with a range of 1.3- to 2.6-fold higher levels found in the brain compartment compared to plasma levels in mice one hour after IV dosing (Table 5). Based on these brain: plasma ratios, it is estimated that following a 5 mg/kg IP dose used in the MCAO studies the free drug concentration in the brain can reach 60-134 nM, 51-103 nM, 33-66 nM, and 28-56 nM at 1, 2, 4, and 8 hours post dosing, respectively. Given that the potency of NP10679 for GluN2B at pH 6.9 is 23 nM, the occupancy of GluN2B receptors at pH 6.9 in the brain compartment is sufficiently high to drive significant GluN2B inhibition.

averaged for each drug. Results were analyzed by ANOVA and Dunnett's post hoc test to compare horizontal activity of drug-treated groups to vehicle controls. Male animals were used for these behavioral tests given only male mice were used in the MCAO transient ischemia studies.

For rotarod experiments, male C57BL/6 mice (>90 days old) were tested using a Rotamax 4/8 rotarod (Columbus Instruments, Columbus, Ohio). Prior to training and testing, the mice were brought to the testing room and allowed to acclimate for two hours prior to any further handling. Mice were placed on a rotating rod (5 rpm), 3.8 cm in diameter and 8 cm wide, elevated 30 cm from the floor of a chamber. After 10 sec of rotation at a fixed velocity, the rotation was slowly accelerated from 5 to 35 rpm over a 5 min period. The duration of time that the mouse could stay on the rotarod, without hanging on for a full rotation or without falling, was recorded. Mice were trained 4 times at 25 min inter-trial intervals on each day for two days. On day three, mice were randomly assigned to treatment groups and administered test drug or vehicle (via IP administration) 25 min prior to testing (4 trials with inter-trial interval of 25 min). Individuals performing the experiment were blinded to

TABLE 5

Pharmacokinetic parameters determined in mice for NP10679

| Species | Oral Bioavailability Mouse BALB/c | | IP Dosing Mouse BALB/c | | Brain:Plasma Ratios[A] Mouse BALB/c | | |
|---|---|---|---|---|---|---|---|
| Dose (mg/kg) | 10 | 3 | 2 | 5 | | 3 | |
| Route | PO | IV | IP | IP | | IV | |
| Study[B] | — | — | — | — | 1 | 2A | 2B |
| Plasma $C_{max}$ (ng/mL) | 3600 | 2350 | 581 | 1470 | 2300 | 600 | 817 |
| Plasma $T_{max}$ (h) | 1.0 | 0.08 | 0.5 | 0.5 | 1.0 | 1.0 | 1.0 |
| Brain Conc. (ng/g) | — | — | — | — | 1740 | 1420 | 2100 |
| Brain:Plasma Ratio | — | — | — | — | 1.3 | 2.4 | 2.6 |
| Plasma $AUC_{last}$ (h * ng/mL) (0 to 24 h) | 45000 | 17800 | 4750 | 11800 | — | — | — |
| Plasma $AUC_{inf}$ (h * ng/mL) | 49500 | — | 5690 | 13100 | — | — | — |
| Plasma $AUC_{extrap}$ (%) | 9.18 | — | 16.6 | 9.8 | — | — | — |
| Plasma $T_{1/2}$ (h) | 7.06 | 8.56 | 9.9 | 7.5 | — | — | — |
| Plasma $MRT_{last}$ | 7.16 | 7.08 | 7.5 | 6.7 | — | — | — |
| $V_{ss}$ (L/kg) | — | 1.59 | — | — | — | — | — |
| CL (mL/min/kg) | — | 2.44 | — | — | — | — | — |
| Bioavailability (F %) | 75.7 | — | — | — | — | — | — |

Data are given up to three significant figures.

[A]Brain:plasma ratio studies reported only at 1 hour.

[B]All studies used 10% DMA/10% PG/30% HPBCD/50% sterile water formulation, except Study 2A which used 2% DMA/10% PG/30% HPBCD/58% sterile water.

Example 5. Locomotor Activity and Rotarod Performance

A. Materials and Methods

Measurement of Locomotor Activity and Rotarod Performance

The locomotor and rotarod studies were approved by the Georgia State University IACUC, an AAALAC accredited institution under the supervision of licensed veterinarians. Mice were group housed, provided nestlets and shelters with access to food pellets and water ad libitum under a 12-hour light/dark cycle.

For locomotor activity measurements, mice (C57B16, >90 days old, Jackson Labs) were placed in a closed (with light on) activity monitoring box for one hour to habituate prior to drug testing. After one hour, animals were removed and injected (IP) with drug and then returned to the activity monitoring box and total locomotor activity was monitored for two hours. The total number of light beam breaks in the cage (horizontal) was determined by a computer and results the identity of each treatment group. Results were analyzed by ANOVA and Dunnett's post hoc test to compare duration of time on the rotating rod of drug-treated groups to the vehicle controls.

B. Results

Figure 3:
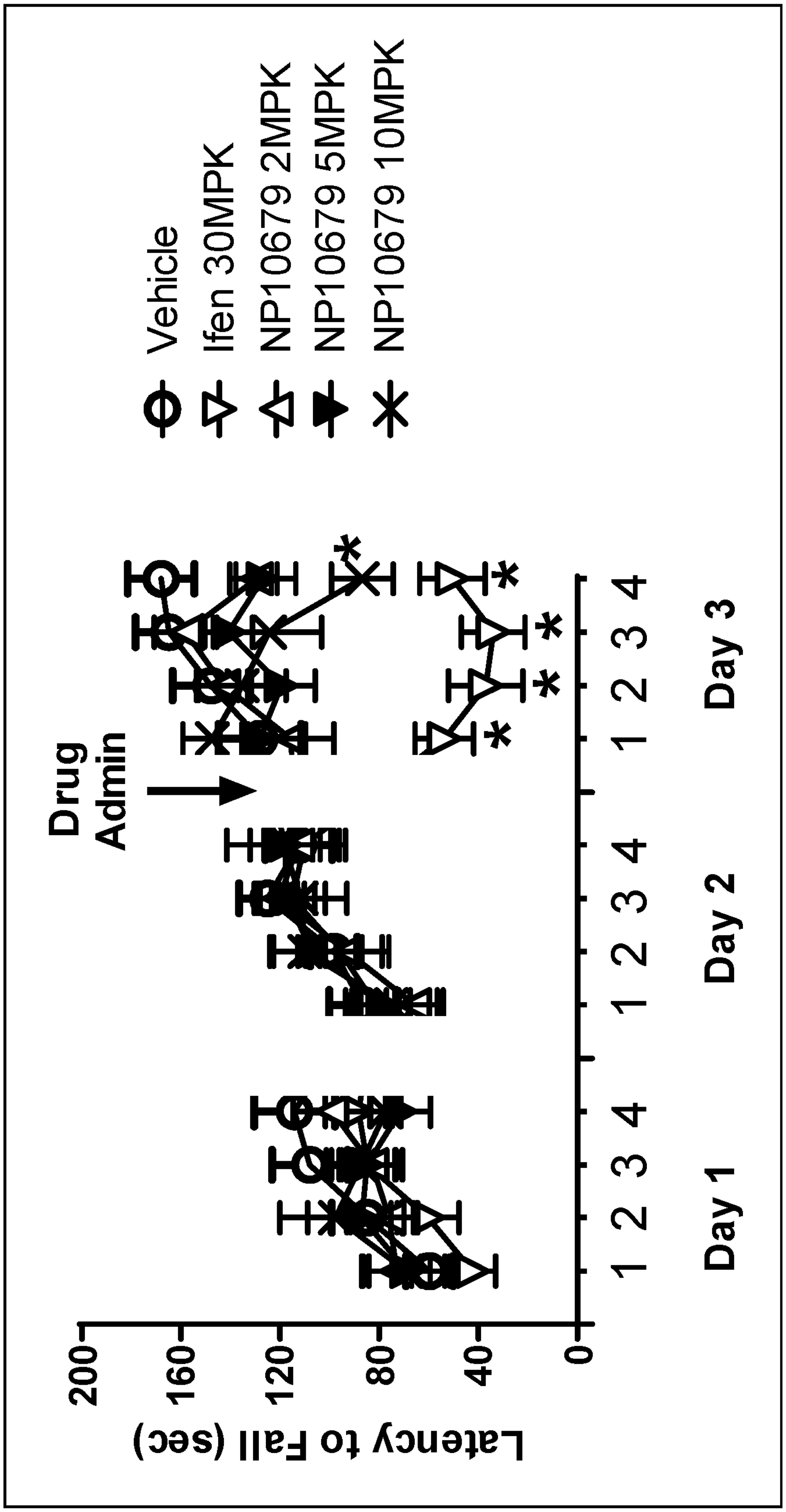
FIG. 3 is a graph showing the mice's latency to fall (second) on a rotarod plotted against time (day). Mice were trained on the rotarod on two consecutive days (Day 1 and 2), with 4 trials per day and an inter-trial interval of 25 min. On Day 3, the mice were randomized to groups and administered with the vehicle control (open circles), ifenprodil at 30 mg/kg (open downward-facing triangles), or an exemplary compound (NP10679) at 2 mg/kg (open upward-facing triangles), 5 mg/kg (solid downward-facing triangles), or 10 mg/kg (cross marks). The latency to fall was calculated for each group and is shown in mean±SEM (n=8). * p<0.01 from the vehicle control for individual trials on Day 3 (ANOVA, Dunnett's).

Studies were performed to evaluate whether NP10679 perturbed motor coordination or function. The mice were tested in a rotarod challenge study after dosed with NP10679. Here, the mice were trained on two consecutive days for ability to stay on the rotating and accelerating bar with 4 trials each day (inter-trial interval of 25 min). The mice showed improved performance from Day 1 to Day 2 across intra-day trials as shown in FIG. 3. On Day 3, the mice were randomly assigned to treatment groups, dosed with vehicle or drug, and then tested four times beginning 25 mins post dose, and the mean latency to fall was established for each trial (FIG. 3). There was no significant impairment by NP10679 when dosed at 2 mg/kg or 5 mg/kg across all four trials. The 10 mg/kg NP10679 dose group had a reduced latency to fall in the fourth trial (87±13 sec) compared to the vehicle control (168±14 sec). However, no statistically significant change from the vehicle control was observed in trials 1, 2, or 3 for this treatment group. By contrast, a 30 mg/kg dose of ifenprodil led to a significant reduction in the latency-to-fall score in all four trials tested (FIG. 3). The higher dose for ifenprodil was selected given that it is less potent than NP10679 against GluN2B (Kew, et al., *J Physiol,* 1996, 497:761-772; Mott, et al., *Nat Neurosci,* 1998, 1(8):659-67) and requires a higher concentration to generate neuroprotection in vitro (Chenard, et al., *J Med Chem,* 1991, 34(10):3085-90).

Figure 4:
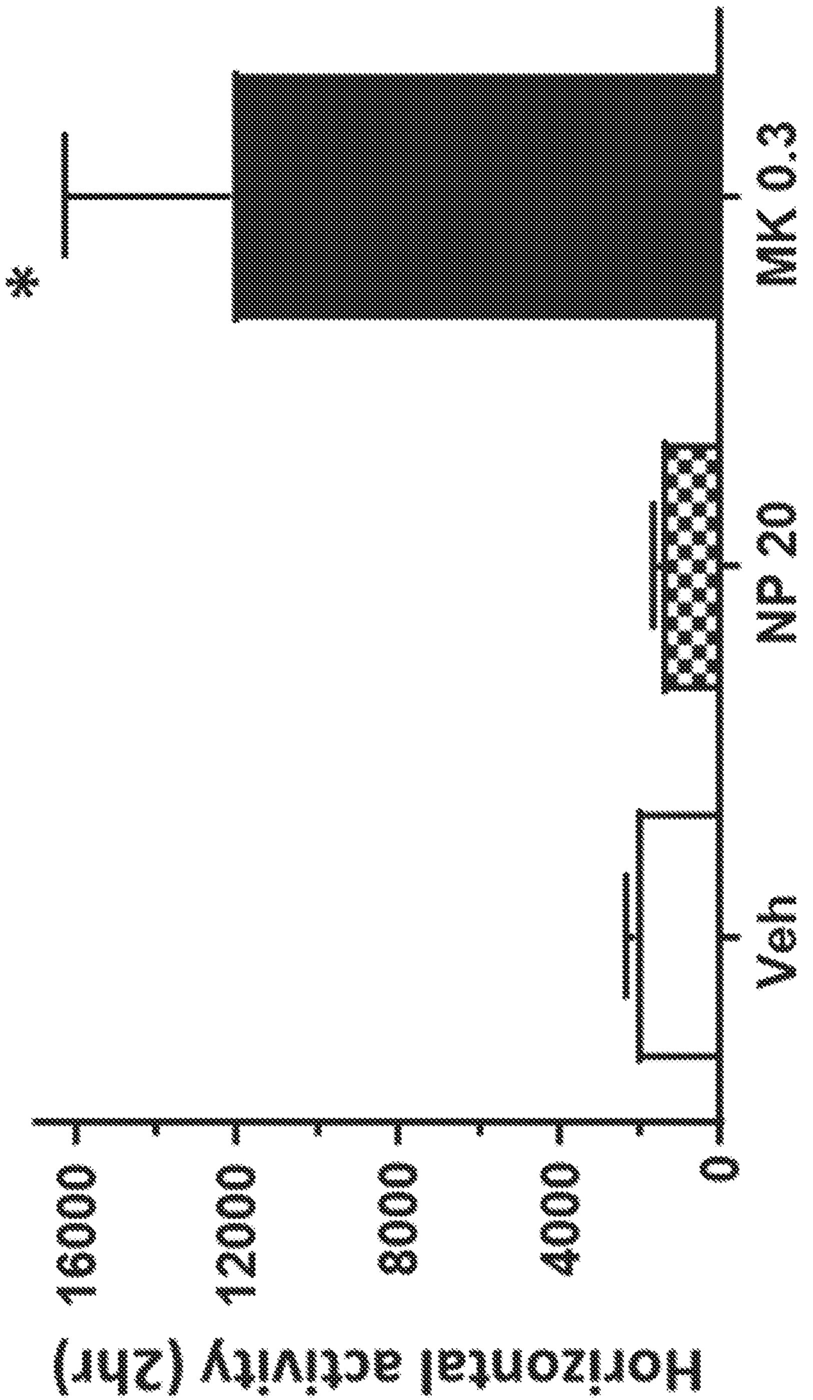
FIG. 4 is a bar graph showing the mice's horizontal activity (within two hours) among three treatment groups, i.e., the vehicle control, MK-801, and an exemplary compound (NP10679). Mice were habituated for 1 hour in a closed locomotor activity box and then removed and administered with vehicle (Veh, n=6), MK-801 (at 0.3 mg/kg, n=4), or NP10679 (at 20 mg/kg, n=6) by IP injection and then placed back in the boxes. The horizontal locomotor activity was measured for 2 hours. * p<0.01 from the vehicle control (ANOVA, Dunnett's). Total number of light beam breaks during the sample time are reported on the abscissa, which is representative of horizontal movement.

The ability of a single dose of NP10679 to alter the locomotor activity of mice was assessed in a closed, lighted chamber (FIG. 4). After a one-hour habituation period, the mice were administered a 20 mg/kg dose of NP10679 or 0.3 mg/kg MK-801 and returned to the closed, lighted chamber and horizontal activity measured for two hours. NP10679 at this dose did not generate any statistically significant decrease in the horizontal activity of mice, compared to the vehicle control (n=6 each). In contrast, administration of 0.3 mg/kg MK-801 led to a significant increase ($p<0.01$) in horizontal activity (n=4).

Taken together, NP10679 shows enhanced inhibition against GluN2B at an extracellular acidic pH value (pH 6.9) relative to pH 7.6. Notably, NP10679 exhibits much higher potency against GluN2B compared to its S enantiomer (NP10309) while maintaining the pH boost.

These properties render NP10679 a more effective inhibitor of NMDARs compared to its S enantiomer at synapses responding to a high frequency of action potentials, since glutamate-containing vesicles are acidic within their lumen. In addition, acidification of penumbral regions around ischemic tissues can also enhance the action of NP10679 for improved neuroprotection.

When tested in nonhuman primates in cognitive tasks and learning paradigms following acute administration, two GluN2B inhibitors, traxoprodil and BMT-108908, produced cognitive impairments in a dose-dependent manner (Weed, et al., *Neuropsychopharm,* 2016, 46:568-577). Traxoprodil does not possess a significant pH sensitivity for inhibition of receptors between pH 6.8 and pH 7.5 (Mott, et al., *Nat Neurosci,* 1998, 1(8):659-67). The high potency against GluN2B and significant pH boost effect of NP10679 provide advantages over existing GluN2B-targeting drugs and drug candidates in separating side effects from the desired on-target activity.

Further, NP10679 has high oral bioavailability with excellent brain penetration, and thus is suitable for both intravenous and oral dosing for therapeutic uses in man.

Example 6. Human Clinical Studies

A. Materials and Methods

Drug Substance and Product

Synthesis of the GMP quality active pharmacological ingredient (API) of NP10679 for use in the drug product was outsourced to DavosPharma (Saddle River, NJ). The manufacturing of the drug product was performed by University of Iowa, Pharmaceuticals (UI-P) according to procedures established for the generation of lyophilized product. To formulate the drug product, the API was solubilized in a vehicle of 25% hydroxypropyl-beta-cyclodextrin (HPBCD) in 50 mM potassium phosphate monobasic buffer (pH 6.0) to a concentration of 5 mg/mL. This solution was then filtered, sterilized, and lyophilized into sterile vials each containing 50 mg API. The lyophilized API was formulated into the drug product for IV infusion at the clinical site by addition of appropriate amounts of 2.5% HPBCD in 0.9% saline.

Methods

Protocols for both the single ascending dose (SAD) and multiple ascending dose (MAD) studies were reviewed and approved by the US Food and Drug Administration under an investigational new drug application. These protocols as well as subject informed consent packages were also reviewed and approved and by the institutional review board (IRB) for the study, IntegReview IRB, Austin TX. The clinical research organization (CRO) for both studies was Pharmaron CPC, Baltimore, Maryland. All subjects were informed of the nature and purpose of the study, and their written informed consent was obtained before any study-related procedures were performed. Studies were conducted in accordance with the principles set forth in the Declaration of Helsinki and the International Conference on Harmonization Tripartite Guidance on Good Clinical Practice.

Inclusion and Exclusion Criteria

Healthy male and female subjects aged 18 to 55 who were capable of providing consent and able to adhere to the visit schedule and other protocol requirements were eligible for the studies. If sexually active and having childbearing potential (both men and women), volunteers were required to agree to use two forms of contraceptive methods (one barrier) for the duration of the study.

Exclusion criteria included inadequate peripheral forearm vein access, pregnancy or lactation, use of nicotine-containing products during the study, current or recent (within 12 months) history of alcohol or drug abuse, recent (within 90 days) blood donation, and previous participation in a clinical trial withing 90 days. Subjects with excessive somnolence and those who had used medications or agents that might cause drowsiness within 7 days were also excluded. Volunteers with significant medical or psychiatric illness by history, examination, or clinical laboratory testing that would influence study results or preclude informed consent and study compliance were also excluded.

Clinical Study Designs

The SAD study (NP10679-101) was a single center, randomized, double blind, placebo controlled, single dose, dose escalation trial to investigate the safety, tolerability, and pharmacokinetics (PK) of NP10679 in healthy adult volunteers in six escalating dosing cohorts. The primary objective of the study was to assess the safety, tolerability, and PK of a single dose of NP10679 when delivered by IV infusion in comparison to placebo. Secondary objectives were to obtain a maximum tolerated dose of NP10679 in healthy adult volunteers and to establish a safe starting dose for the MAD study (NP10679-102).

The study consisted of a 30-day screening period, Day 1 (single IV infusion of NP10679 or placebo, as randomized), Day 2 in clinic/overnight assessments, and Day 3 assessments. Subjects checked into the clinic on Day 1 and remained in the clinic through the 48 h post-dose blood draw on Day 3, after which time they were discharged. Subjects returned to the clinic for a follow-up visit at Day 8 after discharge.

There were six dosing cohorts studied in NP10679-101. Each cohort consisted of 8 subjects. Six subjects of each cohort were administered NP10679 and two subjects received placebo. Doses were evaluated sequentially before escalating to the next dose level. Doses included in the study were 5, 15, 50, 100 and 200 mg. Drug and placebo were administered by IV infusion in 75 ml of dosing vehicle over 30 minutes. A sentinel dosing, adaptive design approach was used for all cohorts, in which the first 2 subjects (1 active, 1 placebo) were dosed on Day 1 and observed for 48 h or until sufficient time had elapsed to review safety. If the safety committee (at a minimum, the Principal Investigator (PI) and Medical Monitor (a subject matter MD independent from the conduct of the study) agreed that it was safe to proceed, the remaining 6 subjects (5 active, 1 placebo) were dosed in that cohort at the same dose level. Safety/tolerability data as well as available PK data were reviewed prior to dosing in the next cohort of subjects. Acceptable results of the interim safety/tolerability review triggered enrollment into the next dosing cohort.

The purpose of the MAD study was to evaluate safety and pharmacokinetics of NP10679 upon repeated dosing until steady state was reached. Based on results from the SAD study, it was determined that 5 days of once daily dosing would lead to steady state. Subjects in the MAD study (NP10679-102) were treated in the same way as those in NP10679-101. The study consisted of a 30-day screening period, dosing Days 1 through 5 (single 75 ml IV infusions of NP10679 or placebo over 30 min, as randomized) and Day 6 in clinic/overnight assessments and Day 7 assessments prior to discharge. Subjects checked into the clinic on Day 1 and remained in the clinic through the 48 h post-dose blood draw on Day 7, after which time they were discharged. Subjects returned to the clinic for a follow-up visit at Day 9. Three dosing cohorts of 8 subjects each (6 drug and 2 placebo) were recruited and dosing decisions were made as in NP10679-101. Dose levels included 25, 50 and 100 mg.

Safety Evaluations

Safety/tolerability parameters were assessed according to the protocol schedule of assessments and included assessment of treatment-emergent adverse events based on physical examinations, infusion site examinations, laboratory findings, neuropsychiatric assessments, vital signs and subject reported tolerability. End points also include hematology, chemistry, urinalysis and 12-lead ECG. The Hamilton Depression Rating Scale (HDRS), the Mini-Mental Status Examination (MMSE), the Suicide Behaviors Questionnaire-Revised (SBQ-R), the 7-item General Anxiety Disorders scale (GAD-7) and the Clinician-Administered Dissociative States Scale (CADSS) were included as standard assessments. Modified Observer's Assessment of Alertness/Sedation (MOAA/S) and the Bond-Lader VAS sleepiness scale were also added.

All subjects who had at least one dose of the trial medication and a safety follow-up, whether withdrawn prematurely or not, were included in the safety analysis. Data were summarized by reporting the number and percentage of subjects in each category for categorical and ordinal measures, and mean, SD, median, and range for continuous measures. Safety endpoint included a summary of treatment-emergent clinical and laboratory-based adverse events and their severity. All adverse events were coded by System Organ Class and Preferred Term according to the Medical Dictionary for Regulatory Activities (MedDRA). The treatment-emergent adverse events were tabulated by dose level, System Organ Class, and Preferred Term.

Pharmacokinetic Measurements

For the SAD study, blood was drawn via a vein opposite the infusion arm (if possible) for determination of systemic NP10679 levels at pre-dose and at end of infusion (20 min 5 min), and 0.5, 1, 2, 4, 6, 8, 10, 12, 18, 24, 36, 48 h post-dose. Collection tubes containing $K_2EDTA$ were be used to collect 5 mL of whole blood sample at each time point. Immediately after collection, tubes were inverted to mix the anticoagulant with the blood sample. Tubes were then centrifuged at a speed of approximately 3000 g force for 10 minutes at 4° C. Within 5 minutes of centrifugation the plasma fraction was transferred into two equal aliquots (1.25 mL each) into 2 mL cryovials and then frozen and stored at −70° C. (±10° C.) until shipment. For the MAD study, blood was also drawn via a vein opposite the infusion arm (if possible) for determination of systemic NP10679 levels at pre-dose and at end of infusion (30 min±5 min), and at 0.5, 1, 2, 4, 6, 8, 10, 12, 18 h on Days 1-5 and at 24, 36, 48 and 96 h following the final dose on day 5.

Sensitive, specific, and reproducible bioanalytical methods were developed and validated at MPI Research (Mattawan, MI) to quantitate NP10679. Standards, controls, and test plasma samples containing NP10679 were quantitated by a validated LC-MS/MS assay(s) subsequent to protein precipitation. A structural analog of NP10679 (NP10767, structure shown below) was used as the internal standard (IS). The method was adapted and used to measure plasma samples by TMD Pharmaceutical Research (Newark, DE). Chromatographic retention of NP10679 and the IS was obtained on an Agilent Poroshell 120 EC-C18, 2.1×30 mm, 2.7 m column (Santa Clara, California) under gradient conditions with a flow rate of 0.3 mL/minute. Analytes were detected by multiple reaction monitoring using an MDS Sciex API 4000 mass spectrometer (AB Sciex, Framingham, MA) in positive mode. Plasma concentrations from the resulting LC-MS/MS data were calculated using a 6-10 point calibration curve constructed from known concentrations of NP10679. The lower limit of quantitation (LLOQ) for NP10679 was 2 ng/mL in diluted plasma.

NP10767

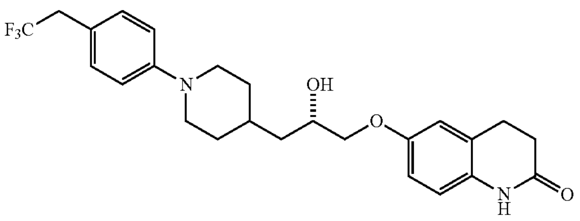

Descriptive pharmacokinetic parameters were calculated based on the plasma concentrations of NP10679. The pharmacokinetic analysis was performed based on the non-compartmental analysis approach (M. Garibaldi and D Perrier, Pharmacokinetics $2^{nd}$ Edition, Chapter 11, Marcel Dekker Inc., New York, 1982) using MS Excel®.

B. Results

Forty-eight subjects were enrolled (Table 6) into the 6 cohorts of the NP10679-101 study and 47 subjects completed. One subject left the study voluntarily due to personal reasons not related to the study. The median age for this study was 33.5 years (Min/Max—22/52 years). There were 30 males and 18 female enrolled into the study. Most subjects were Black (35) followed by White (13: including 10 non-Hispanic and 3 Hispanic) and 1 Asian.

TABLE 6

| Demographics of Study NP10679-101 | | | | | | | | | |
|---|---|---|---|---|---|---|---|---|---|
| | NP10679 | | | | | | | | |
| | 5 mg (N = 6) | 15 mg (N = 6) | 50 mg (N = 6) | 100 mg (N = 6) | 150 mg (N = 6) | 200 mg (N = 6) | Total (N = 36) | Placebo (N = 12) | Total (N = 48) |
| Age at Consent (years) | | | | | | | | | |
| n | 6 | 6 | 6 | 6 | 6 | 6 | 36 | 12 | 48 |
| Mean | 35.8 | 33.0 | 37.0 | 35.7 | 39.8 | 37.3 | 36.4 | 35.3 | 36.1 |
| SD | 11.92 | 8.17 | 8.15 | 4.93 | 12.02 | 11.13 | 9.25 | 10.34 | 9.43 |
| Median | 34.5 | 30.5 | 37.5 | 35.5 | 40.5 | 37.0 | 33.5 | 32.0 | 33.5 |
| Min | 23 | 23 | 28 | 29 | 27 | 22 | 22 | 22 | 22 |
| Max | 51 | 46 | 48 | 42 | 52 | 51 | 52 | 52 | 52 |
| Sex | | | | | | | | | |
| Male | 4 (66.7%) | 2 (33.3%) | 4 (66.7%) | 3 (50.0%) | 4 (66.7%) | 5 (83.3%) | 22 (61.1%) | 8 (66.7%) | 30 (62.5%) |
| Female | 2 (33.3%) | 4 (66.7%) | 2 (33.3%) | 3 (50.0%) | 2 (33.3%) | 1 (16.7%) | 14 (38.9%) | 4 (33.3%) | 18 (37.5%) |
| Race | | | | | | | | | |
| White | 0 | 1 (16.7%) | 0 | 0 | 3 (50.0%) | 3 (50.0%) | 7 (19.4%) | 3 (25.0%) | 10 (20.8%) |
| Black/African American | 6 (100%) | 4 (66.7%) | 4 (66.7%) | 6 (100%) | 3 (50.0%) | 3 (50.0%) | 26 (72.2%) | 9 (75.0%) | 35 (72.9%) |
| Asian | 0 | 0 | 1 (16.7%) | 0 | 0 | 0 | 1 (2.8%) | 0 | 1 (2.1%) |
| Pacific Islander | 0 | 0 | 0 | 0 | 0 | 0 | 0 | 0 | 0 |
| American Indian or Alaskan Native | 0 | 0 | 0 | 0 | 0 | 0 | 0 | 0 | 0 |
| Mixed/Other | 0 | 1 (16.7%) | 1 (16.7%) | 0 | 0 | 0 | 2 (5.6%) | 0 | 2 (4.2%) |

The NP10679-102 MAD study enrolled (Table 7) 24 subjects into 4 cohorts. The median age for this study was 44.5 years (Min/Max—20/54 years). There were 15 males and 9 females enrolled into the study. As in the SAD study, most subjects were Black (15) followed by White (8) and Asian (1).

TABLE 7

| Demographics of Study NP10679-102 | | | | |
|---|---|---|---|---|
| | NP10679 25 mg (N = 6) | NP10679 50 mg (N = 6) | NP10679 100 mg (N = 6) | Placebo (N = 6) |
| Age at Consent (years) | | | | |
| n | 6 | 6 | 6 | 6 |
| Mean | 40.8 | 42.5 | 41.0 | 41.3 |
| SD | 10.03 | 13.10 | 11.42 | 11.89 |
| Median | 41.5 | 48.0 | 42.5 | 45.5 |
| Min | 29 | 20 | 24 | 22 |
| Max | 54 | 53 | 53 | 53 |

TABLE 7-continued

| Demographics of Study NP10679-102 | | | | |
|---|---|---|---|---|
| | NP10679 25 mg (N = 6) | NP10679 50 mg (N = 6) | NP10679 100 mg (N = 6) | Placebo (N = 6) |
| Sex, n (%) | | | | |
| Female | 4 (66.7%) | 1 (16.7%) | 3 (50.0%) | 1 (16.7%) |
| Male | 2 (33.3%) | 5 (83.3%) | 3 (50.0%) | 5 (83.3%) |
| Race, n (%) | | | | |
| White | 2 (33.3%) | 1 (16.7%) | 2 (33.3%) | 3 (50.0%) |
| Black or African American | 4 (66.7%) | 4 (66.7%) | 4 (66.7%) | 3 (50.0%) |
| Asian | 0 | 1 (16.7%) | 0 | 0 |

Table 8 summarizes the treatment emergent adverse events (TEAEs) by organ class and dose for NP10679-101. At the highest dose tested, 200 mg, the most common treatment-emergent adverse event (TEAE) was somnolence.

TABLE 8

| Summary of Treatment-Emergent Adverse Events by System Organ Class and Preferred Term for Study NP10679-101 | | | | | | | | |
|---|---|---|---|---|---|---|---|---|
| | NP10679 | | | | | | | |
| System Organ Class Preferred Term | 5 mg (N = 6) n | 15 mg (N = 6) n | 50 mg (N = 6) n | 100 mg (N = 6) n | 150 mg (N = 6) n | 200 mg (N = 6) n | Total (N = 36) n | Placebo (N = 12) n |
| Subjects Who Had a TEAE | 1 | 4 | 5 | 5 | 5 | 6 | 26 | 3 |
| Nervous system disorders | 1 | 1 | 5 | 5 | 5 | 6 | 23 | 0 |
| Somnolence | 1 | 1 | 5 | 5 | 5 | 6 | 23 | 0 |
| Dizziness | 0 | 0 | 0 | 1 | 3 | 2 | 6 | 0 |

TABLE 8-continued

Summary of Treatment-Emergent Adverse Events by System Organ Class and Preferred Term for Study NP10679-101

| | NP10679 | | | | | | | |
|---|---|---|---|---|---|---|---|---|
| System Organ Class Preferred Term | 5 mg (N = 6) n | 15 mg (N = 6) n | 50 mg (N = 6) n | 100 mg (N = 6) n | 150 mg (N = 6) n | 200 mg (N = 6) n | Total (N = 36) n | Placebo (N = 12) n |
| Headache | 0 | 1 | 0 | 1 | 0 | 3 | 5 | 0 |
| Presyncope | 0 | 0 | 1 | 0 | 1 | 1 | 3 | 0 |
| Tremor | 0 | 0 | 0 | 0 | 1 | 0 | 1 | 0 |
| Eye disorders | 0 | 0 | 0 | 1 | 0 | 4 | 5 | 0 |
| Conjunctival hyperaemia | 0 | 0 | 0 | 0 | 0 | 4 | 4 | 0 |
| Scleral hyperaemia | 0 | 0 | 0 | 0 | 0 | 4 | 4 | 0 |
| Vision blurred | 0 | 0 | 0 | 1 | 0 | 0 | 1 | 0 |
| General disorders and administration site conditions | 0 | 1 | 0 | 1 | 1 | 1 | 4 | 2 |
| Fatigue | 0 | 1 | 0 | 0 | 1 | 0 | 2 | 0 |
| Asthenia | 0 | 0 | 0 | 0 | 1 | 0 | 1 | 0 |
| Discomfort | 0 | 0 | 0 | 0 | 0 | 1 | 1 | 0 |
| Feeling hot | 0 | 0 | 0 | 1 | 0 | 0 | 1 | 0 |
| Infusion site pain | 0 | 0 | 0 | 0 | 0 | 0 | 0 | 1 |
| Injection site bruising | 0 | 0 | 0 | 0 | 0 | 0 | 0 | 1 |
| Blood and lymphatic system disorders | 1 | 1 | 1 | 1 | 0 | 0 | 4 | 0 |
| Anaemia | 1 | 1 | 1 | 1 | 0 | 0 | 4 | 0 |
| Skin and subcutaneous tissue disorders | 0 | 1 | 1 | 1 | 1 | 0 | 4 | 0 |
| Dermatitis contact | 0 | 1 | 0 | 0 | 0 | 0 | 1 | 0 |
| Ecchymosis | 0 | 0 | 1 | 0 | 0 | 0 | 1 | 0 |
| Erythema | 0 | 0 | 0 | 0 | 1 | 0 | 1 | 0 |
| Hyperhidrosis | 0 | 0 | 0 | 1 | 0 | 0 | 1 | 0 |
| Gastrointestinal disorders | 0 | 0 | 0 | 1 | 0 | 1 | 2 | 1 |
| Nausea | 0 | 0 | 0 | 0 | 0 | 1 | 1 | 1 |
| Abdominal pain | 0 | 0 | 0 | 1 | 0 | 0 | 1 | 0 |
| Constipation | 0 | 0 | 0 | 1 | 0 | 0 | 1 | 0 |
| Vascular disorders | 0 | 0 | 0 | 0 | 0 | 1 | 1 | 1 |
| Flushing | 0 | 0 | 0 | 0 | 0 | 1 | 1 | 0 |
| Hypertension | 0 | 0 | 0 | 0 | 0 | 0 | 0 | 1 |
| Ear and labyrinth disorders | 0 | 0 | 0 | 0 | 1 | 0 | 1 | 0 |
| Auditory disorder | 0 | 0 | 0 | 0 | 1 | 0 | 1 | 0 |
| Injury, poisoning and procedural complications | 0 | 0 | 0 | 0 | 1 | 0 | 1 | 0 |
| Infusion related reaction | 0 | 0 | 0 | 0 | 1 | 0 | 1 | 0 |
| Investigations | 0 | 0 | 0 | 0 | 0 | 1 | 1 | 0 |
| Blood creatine phosphokinase increased | 0 | 0 | 0 | 0 | 0 | 1 | 1 | 0 |
| Musculoskeletal and connective tissue disorders | 0 | 0 | 0 | 0 | 1 | 0 | 1 | 0 |
| Myalgia | 0 | 0 | 0 | 0 | 1 | 0 | 1 | 0 |
| Psychiatric disorders | 0 | 0 | 0 | 0 | 1 | 0 | 1 | 0 |
| Intrusive thoughts | 0 | 0 | 0 | 0 | 1 | 0 | 1 | 0 |
| Renal and urinary disorders | 0 | 0 | 1 | 0 | 0 | 0 | 1 | 0 |
| Urinary hesitation | 0 | 0 | 1 | 0 | 0 | 0 | 1 | 0 |
| Respiratory, thoracic and mediastinal disorders | 0 | 0 | 0 | 0 | 0 | 1 | 1 | 0 |
| Nasal discomfort | 0 | 0 | 0 | 0 | 0 | 1 | 1 | 0 |

TEAE = Treatment-emergent adverse event; N = Number of subjects in respective dosing level and treatment in safety population; n = number of subjects with event.

There was a dose response for somnolence (see Table 9), the most prevalent TEAE. The Modified Observer's Assessment of Alertness/Sedation (MOAA/S) scale is scored from 0 to 5 with level 5 representing the lowest level of sedation. At level 5, a subject readily responds to normal spoken tones, level 4 indicates a lethargic response to voice, and level 3 requires a louder voice to elicit a response. Scores below 3 require increasing levels of physical stimuli to arouse subjects. NP10679 elicited moderate effects on the MOAA/S scale at higher dose levels. One of 6 subjects at doses of 5 and 15 mg, and 5 of 6 subjects at doses of 50-200 mg presented with somnolence. Two subjects in each of the 100 and 150 mg cohorts reached a transient level 3 score on the MOAA/S scale. However, no subject in the highest dose group (200 mg) reached this score. There were also moderate increases in the Bond-Lader VAS scale starting at the 50 mg dose and continuing through to the 200 mg dose. The somnolence observed in the study was viewed to be phenomenologically different from that observed with classic sedative hypnotics. This reduced the overall confidence in the tools used to score it. Even at the highest dose tested, when subjects were stimulated, they quickly oriented to their environment within seconds, and were able to perform relatively complicated tasks such as the Digit Symbol Substitution Test (DSST).

TABLE 9

| NP10679-101 Summary of Shift from Baseline in MOAA/S | | | | | | |
|---|---|---|---|---|---|---|
| | Worst Post-baseline* | | | | | |
| Treatment | 5 | 4 | 3 | 2 | 1 | 0 |
| NP10679 5 mg (N = 6) | 6 | 0 | 0 | 0 | 0 | 0 |
| NP10679 15 mg (N = 6) | 6 | 0 | 0 | 0 | 0 | 0 |
| NP10679 50 mg (N = 6) | 2 | 4 | 0 | 0 | 0 | 0 |
| NP10679 100 mg (N = 6) | 1 | 3 | 2 | 0 | 0 | 0 |
| NP10679 150 mg (N = 6) | 1 | 3 | 2 | 0 | 0 | 0 |
| NP10679 200 mg (N = 6) | 2 | 4 | 0 | 0 | 0 | 0 |
| Placebo (N = 12) | 10 | 2 | 0 | 0 | 0 | 0 |

*Worst post-baseline is the lowest score at all post-baseline visits, including any scheduled, unscheduled, and ET/FU visits.

A TEAE of dizziness may have also been more frequent at higher doses at or above 100 mg. This was reported in 1 subject at 100 mg, 2 subjects at 150 mg and 200 mg respectively. Headache and pre-syncope were less common and did not appear to show a dose response. A TEAE of tremor occurred once in a subject dosed with 100 mg. None of these TEAEs were deemed to impact subject safety. Other than Nervous Systems disorders, conjunctival and scleral hyperemia were observed in 3 of 6 subjects at the 200 mg dose. This was thought to be related to a non-clinically significant lower blood pressure (both systolic and diastolic) observed at the highest two doses. However, the lower blood pressure was more profound at the 150 mg dose of NP10679 (−23 mg Hg) at 4 hours post dose than at the 200 mg dose (−7.2 mg Hg). There were no clinically significant changes in vital signs or ECGs in the study. Thus, increases in QTc intervals or hypertension observed with previous GluN2B inhibitors were not observed in the NP10679-101 study.

No serious adverse events (SAEs) were observed in the study. There were no patterns that suggested dissociative symptoms or cognitive impairment related to NP10679 in the study as indicated from the Clinician Administered Dissociative States Scale (CADSS) or the Digit Symbol Substitution Test (DSST). While one subject presented with intrusive thoughts at a dose of 150 mg, there were no patterns that suggested dissociative symptoms related to NP10679 in the study as indicated from the Clinician Administered Dissociative States Scale (CADSS).

Table 10 summarizes the treatment emergent adverse events (TEAEs) by organ class and dose for NP10679-102. As was the case for the SAD study, there were no SAEs in the MAD study. Also mirroring the SAD study, the most encountered adverse effect was somnolence. This side effect was observed in 3 subjects in both the 50 and 100 mg groups. However, it was also noted in 3 subjects in the placebo group. There were no signs of increased somnolence upon repeat dosing. While there may have been some accommodation to the somnolence effect, since observations of this effect occurred for the most part only on the first and second day of dosing, there was not enough of a pattern to support a firm conclusion. There were no patterns that suggested dissociative symptoms related to NP10679 in the study as indicated from the Clinician Administered Dissociative States Scale (CADSS).

TABLE 10

NP10679-102 Summary of Treatment-Emergent Adverse Events by System Organ Class and Preferred Term

| System Organ Class Preferred Term | NP10679 25 mg (N = 6) n (%) | NP10679 50 mg (N = 6) n (%) | NP10679 100 mg (N = 6) n (%) | Placebo (N = 6) n (%) |
|---|---|---|---|---|
| Subjects with at least one TEAE | 5 (83.3%) | 3 (50.0%) | 6 (100%) | 6 (100%) |
| Nervous system disorders | 3 (50.0%) | 3 (50.0%) | 4 (66.7%) | 5 (83.3%) |
| Somnolence | 0 | 3 (50.0%) | 3 (50.0%) | 3 (50.0%) |
| Headache | 2 (33.3%) | 0 | 2 (33.3%) | 1 (16.7%) |
| Dysgeusia | 1 (16.7%) | 0 | 0 | 0 |
| Syncope | 0 | 0 | 1 (16.7%) | 0 |
| Dizziness | 0 | 0 | 0 | 1 (16.7%) |
| General disorders and administration site conditions | 1 (16.7%) | 2 (33.3%) | 1 (16.7%) | 3 (50.0%) |
| Fatigue | 1 (16.7%) | 1 (16.7%) | 0 | 2 (33.3%) |
| Pain | 0 | 1 (16.7%) | 1 (16.7%) | 0 |
| Asthenia | 0 | 0 | 1 (16.7%) | 1 (16.7%) |
| Peripheral swelling | 0 | 1 (16.7%) | 0 | 0 |
| Injury, poisoning and procedural complications | 2 (33.3%) | 1 (16.7%) | 1 (16.7%) | 1 (16.7%) |
| Contusion | 2 (33.3%) | 1 (16.7%) | 0 | 1 (16.7%) |
| Head injury | 0 | 0 | 1 (16.7%) | 0 |
| Blood and lymphatic system disorders | 2 (33.3%) | 0 | 1 (16.7%) | 0 |
| Anaemia | 2 (33.3%) | 0 | 1 (16.7%) | 0 |
| Vascular disorders | 0 | 0 | 1 (16.7%) | 1 (16.7%) |
| Phlebitis | 0 | 0 | 1 (16.7%) | 1 (16.7%) |
| Gastrointestinal disorders | 0 | 0 | 1 (16.7%) | 0 |
| Nausea | 0 | 0 | 1 (16.7%) | 0 |
| Investigations | 1 (16.7%) | 0 | 0 | 0 |
| Blood pressure diastolic decreased | 1 (16.7%) | 0 | 0 | 0 |
| Skin and subcutaneous tissue disorders | 0 | 1 (16.7%) | 0 | 0 |
| Erythema | 0 | 1 (16.7%) | 0 | 0 |

TABLE 10-continued

NP10679-102 Summary of Treatment-Emergent Adverse Events by System Organ Class and Preferred Term

| System Organ Class<br>Preferred Term | NP10679 25 mg (N = 6) n (%) | NP10679 50 mg (N = 6) n (%) | NP10679 100 mg (N = 6) n (%) | Placebo (N = 6) n (%) |
|---|---|---|---|---|
| Eye disorders | 0 | 0 | 0 | 1 (16.7%) |
| Vision blurred | 0 | 0 | 0 | 1 (16.7%) |
| Musculoskeletal and connective tissue disorders | 0 | 0 | 0 | 1 (16.7%) |
| Back pain | 0 | 0 | 0 | 1 (16.7%) |

TEAE = Treatment-emergent adverse event; N = Number of subjects in respective treatment in Safety Population; n = Number of subjects with event; % = n/N*100.
Adverse events are coded with MedDRA version 21.1.
Subjects with multiple occurrences of adverse events in the same preferred term are counted only once within that preferred term.
Subjects with multiple occurrences of adverse events in the same system organ class are counted only once within that system organ class.
System organ class as well as preferred terms under system organ class are sorted in descending order of frequency in combined NP10679 group first and then placebo.

Figure 5:
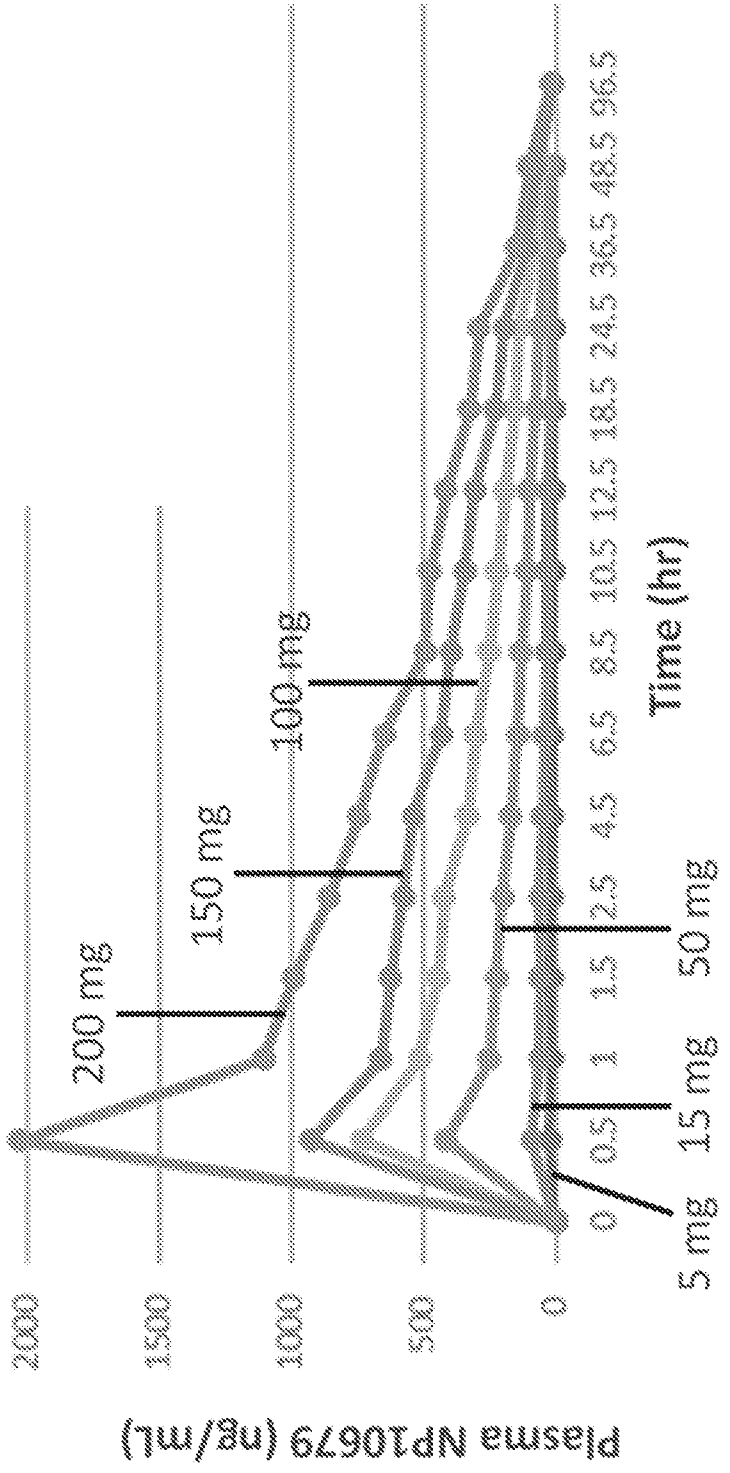
FIGS. 5 and 6 are graphs showing plasma exposure of an exemplary compound (NP10679) after a single intravenous dose in human subjects. Plasma collection and quantification were performed as described herein. Data presented as ng/mL represent the mean of 6 subjects per dose except for the 150 mg group which was the mean of 5 subjects.

In the NP10679-101 study, NP10679 plasma concentrations (see FIG. 5 and Table 11) increased linearly with dose with a mean $C_{max}$ of 30.0±14.8 ng/mL at the 5 mg dose to 2066±798 ng/mL at the 200 mg dose. Thereafter, plasma concentrations declined multi-exponentially with a terminal half-life of 27.6±12.0 hours to 17.4±2.8 hours, respectively. The total clearance ranged from 9.82 L/h±2.89 to 10.4±2.51 L/h over the doses studied. When compared to the hepatic blood flow in human of 87 L/h, NP10679 cleared in the body slowly at less than 12% of the hepatic blood flow. NP10679 appears to distribute extensively throughout the body with a volume of distribution of more than 221 L equating to 4.5 times of the total body water space.

Based on the power model approach, there was a linear and dose proportional increase with $AUC_{(0\text{-}inf)}$ suggesting NP10679 follows linear kinetics from 5 to 200 mg.

TABLE 11

NP10679 Pharmacokinetic Parameters Following an Intravenous Administration in NP10679-101

| | Cohort 1 | Cohort 2 | Cohort 3 | Cohort 4 | Cohort 5 | Cohort 6 |
|---|---|---|---|---|---|---|
| Dose (mg) | 5 | 15 | 50 | 100 | 150 | 200 |
| N | 6 | 6 | 6 | 6 | 5 | 6 |
| $C_{max}$ (ng/mL) | 26.96 ± 14.76 | 99.19 ± 66.60 | 415.40 ± 106.68 | 746.10 ± 222.79 | 953.76 ± 370.47 | 2066.00 ± 797.66 |
| $AUC_{(0\text{-}T)}$ (ng * h/mL) | 335 ± 46 | 1135 ± 233 | 3976 ± 544 | 9366 ± 3085 | 13555 ± 1220 | 19740 ± 4371 |
| $AUC_{(0\text{-}inf)}$ (ng * h/mL) | 533 ± 204 | 1278 ± 227 | 4676 ± 797 | 9865 ± 3223 | 13849 ± 1280 | 20158 ± 4605 |
| $AUMC_{(0\text{-}T)}$ (ng * $h^2$/mL) | 5794 ± 807 | 18219 ± 5732 | 61442 ± 13054 | 201642 ± 103878 | 286984 ± 37671 | 407581 ± 138911 |
| $AUMC_{(0\text{-}inf)}$ (ng * $h^2$/mL) | 35856 ± 43169 | 34553 ± 14287 | 114675 ± 34777 | 253651 ± 126027 | 323299 ± 49874 | 459611 ± 171457 |
| CL (L/h) | 9.82 ± 2.89 | 11.99 ± 1.83 | 11.00 ± 2.18 | 10.96 ± 3.07 | 10.90 ± 0.96 | 10.39 ± 2.51 |
| Vss (L) | 435 ± 178 | 306 ± 41 | 255 ± 20 | 259 ± 57 | 250 ± 23 | 221 ± 34 |
| MRT (h) | 52.9 ± 43.3 | 26.1 ± 5.9 | 23.8 ± 4.1 | 24.5 ± 4.8 | 23.0 ± 1.9 | 21.9 ± 4.0 |
| λ (1/η) | 0.0252 ± 0.0121 | 0.0339 ± 0.0058 | 0.0388 ± 0.0069 | 0.0351 ± 0.0026 | 0.0387 ± 0.0035 | 0.0397 ± 0.0062 |
| $T_{1/2}$* (h) | 27.6 ± 12.0 | 20.4 ± 3.5 | 17.8 ± 3.3 | 19.8 ± 1.5 | 17.9 ± 1.7 | 17.4 ± 2.8 |
| $r^2$ | 0.9737 ± 0.0445 | 0.9652 ± 0.0403 | 0.9874 ± 0.0118 | 0.9972 ± 0.0025 | 0.9975 ± 0.0031 | 0.9955 ± 0.0037 |

*Expressed as harmonic mean and pseudo SD based on jackknife variance.

Figure 6:
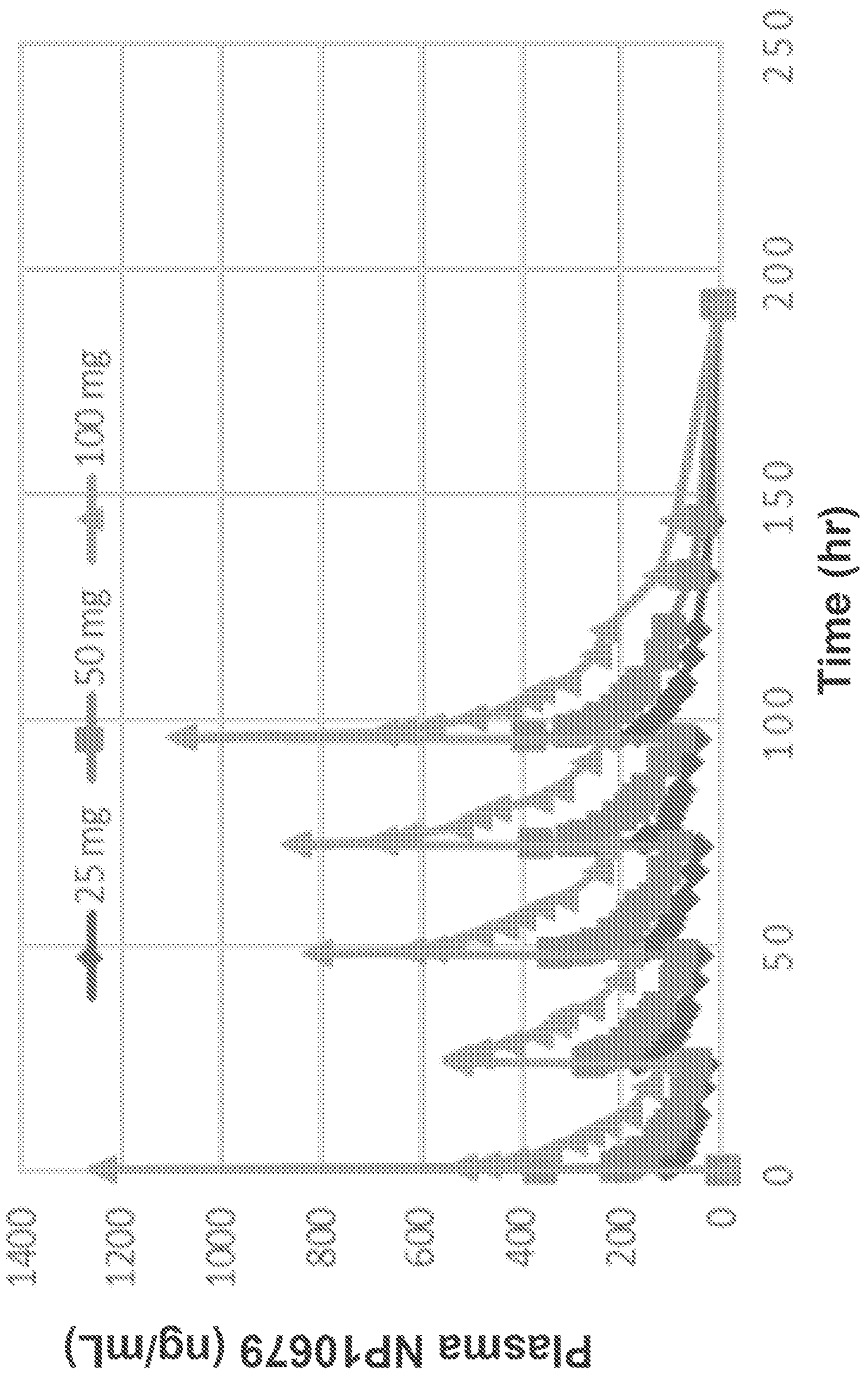

In the NP10679-102 MAD study, all subjects had quantifiable concentrations of NP 10679 in plasma out to 24 hours (pre-dose timepoint of following day) after the first 4 doses and out to 96 hours (last PK timepoint) following the fifth dose (Day 5) except for one subject in the 50 mg Cohort. Mean $C_{max}$ increased with increasing dose (FIG. 6). Over the doses studied, 25 to 100 mg, there was a 5.9-fold and 2.7-fold increase in $C_{max}$ on Day 1 and Day 5 respectively (see Table 12 for pharmacokinetic parameters). Mean AUC also increased with increasing dose. From 25 to 100 mg, there was a 3.8-fold increase in $AUC_{0\text{-}24\ h}$ on Day 1 and a 4.0-fold and 3.6-fold increase on Day 5 for $AUC_{0\text{-}24\ h}$ and $AUC_{0\text{-}96\ h}$, respectively. Thus, both $C_{max}$ and AUC there were roughly linear with increases in dose. Terminal half-life was similar across all doses and days studied with a mean range of 15.4 hours to 36.2 hours, 15.5 hours to 25.6 hours, and 12.5 hours to 34.0 hours for 25 mg, 50 mg, and 100 mg cohorts, respectively. Clearance at steady state was similar across the doses studied with means of 11.5 L/h, 11.8 L/h and 11.2 L/h for 25 mg, 50 mg, and 100 mg cohorts, respectively. Volume of distribution at steady state was decreased slightly as doses increased with means of 360 L, 302 L and 252 L for 25 mg, 50 mg, and 100 mg cohorts, respectively.

TABLE 12

NP10679-102 Pharmacokinetics Parameters of Plasma NP10679

| NP10679 Dose | Day | $C_{max}$ (ng/mL) | $T_{max}$ (h) | $AUC_{0\text{-}24\ h}$ (h * ng/mL) | $AUC_{0\text{-}96\ h}$ (h * ng/mL) | CL (L/h) | Vss (L) | $T_{1/2}$ |
|---|---|---|---|---|---|---|---|---|
| 25 mg | 1 | 208 ± 72 | 0.5 ± 0.0 | 1471 ± 186 | | | | 15 ± 3 |
| | 2 | 211 ± 57 | 0.9 ± 0.8 | 1920 ± 305 | | | | 17 ± 2 |
| | 3 | 207 ± 35 | 0.8 ± 0.4 | 2088 ± 303 | | | | 16 ± 3 |
| | 4 | 250 ± 34 | 0.5 ± 0.0 | 2170 ± 397 | | | | 19 ± 5 |
| | 5 | 213 ± 26 | 0.5 ± 0.0 | 2255 ± 478 | 3877 ± 1143 | 12 ± 3 | 360 ± 51 | 36 ± 15 |
| 50 mg | 1 | 376 ± 99 | 0.8 ± 0.8 | 2652 ± 283 | | | | 18 ± 4 |
| | 2 | 276 ± 60 | 1.0 ± 0.4 | 3295 ± 479 | | | | 18 ± 3 |
| | 3 | 335 ± 73 | 0.8 ± 0.5 | 3885 ± 424 | | | | 26 ± 16 |
| | 4 | 389 ± 116 | 0.8 ± 0.5 | 4109 ± 485 | | | | 16 ± 1 |
| | 5 | 394 ± 72 | 0.7 ± 0.4 | 4293 ± 500 | 6962 ± 1172 | 12 ± 1 | 302 ± 19 | 21 ± 3 |

Adverse events seen in the clinical trial were modest, limited to modest somnolence. This appeared to be dose-related starting from the mid dose of 50 mg in the SAD study. The observation of somnolence did not appear to worsen over the course of 5 days of dosing in the MAD study. The somnolence observed was not similar to that observed with classical sedatives. Even at the highest dose (200 mg) in the SAD study, subjects were readily aroused and were able to complete complex tasks such as the digit symbol substitution test (DSST).

Of note, no dissociative symptoms or reduction cognitive performance were observed in either the SAD or MAD studies. Additionally, no clinically significant events related to the cardiovascular system were noted.

Pharmacokinetic data from the SAD and MAD studies indicate exposures linear with doses and a half-life (~20 hours) suitable for once daily dosing.

In conclusion, the initial human studies NP10679-101 and NP10679-102 demonstrate that NP10679 is safe at the tested doses.

The invention claimed is:

1. A compound having a structure of Formula I or a pharmaceutically acceptable salt, hydrate, or hydrated salt thereof, Formula I

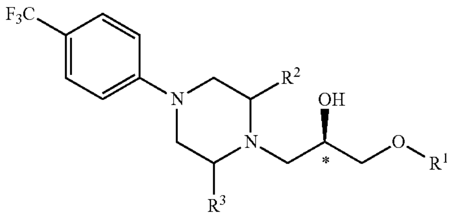

wherein the stereocenter labeled by the * sign has R configuration, wherein $R^1$ is selected from the group consisting of:

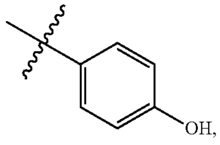

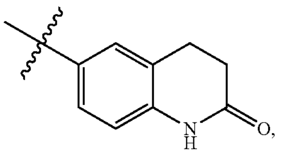

-continued

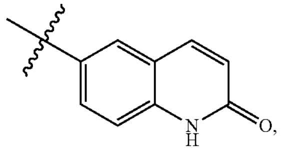

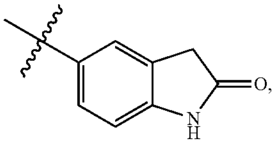

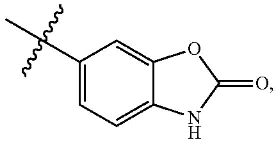

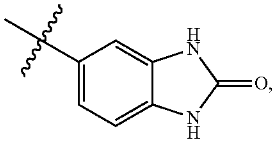

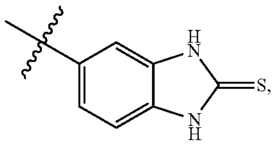

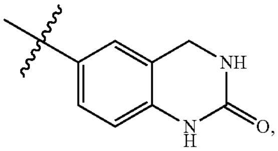

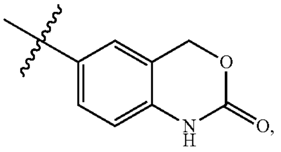

and

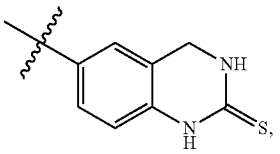

wherein $R^2$ and $R^3$ are independently selected from the group consisting of hydrogen, methyl, and halomethyl.

2. The compound according to claim 1, wherein $R^1$ is:

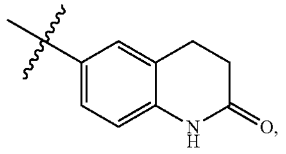

or

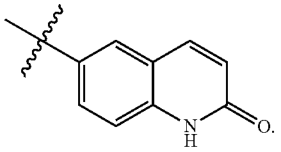

3. The compound according to claim 1, wherein both $R^2$ and $R^3$ are hydrogen.

4. The compound according to claim 1, selected from the group consisting of:

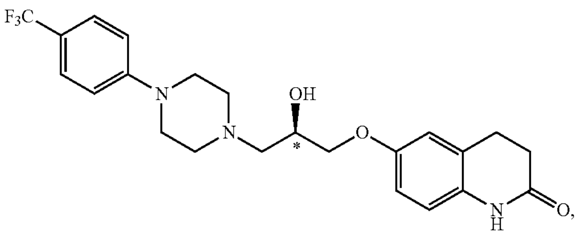

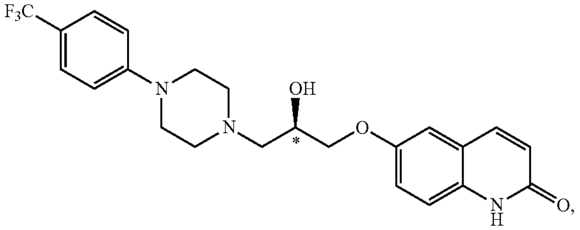

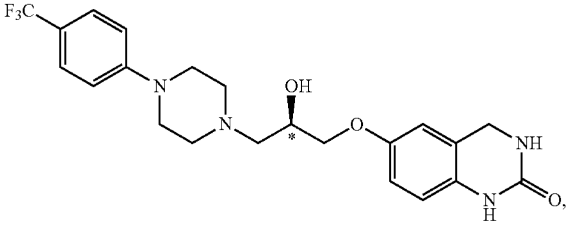

and pharmaceutically acceptable salts, hydrates, and hydrated salts thereof.

5. A compound having a structure of Formula II or a pharmaceutically acceptable salt, hydrate, or hydrated salt thereof, Formula II

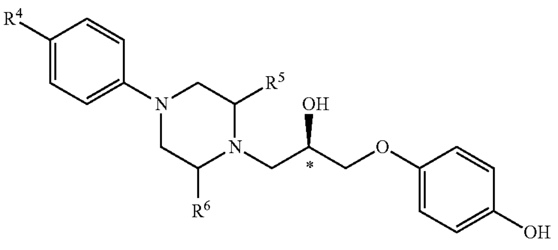

wherein the stereocenter labeled by the * sign has R configuration, wherein $R^4$ is hydrogen, methyl, halomethyl, ethyl, haloethyl, isopropyl, or haloisopropyl, and wherein $R^5$ and $R^6$ are independently selected from the group consisting of hydrogen, methyl, and halomethyl.

6. The compound according to claim 5, wherein:

(i) $R^4$ is methyl or halomethyl, or (ii) both $R^5$ and $R^6$ are hydrogen.

7. A composition comprising the compound according to claim 1, wherein the compound is in greater than 80%, 85%, 90%, or 95% enantiomeric excess for the R configuration, with respect to the stereocenter labeled by the * sign, as depicted in Formula I.

8. The composition according to claim 7, wherein the compound is in greater than 95% enantiomeric excess for the R configuration, with respect to the stereocenter labeled by the * sign, as depicted in Formula I.

9. A pharmaceutical formulation comprising the compound according to claim 1, wherein the pharmaceutical formulation further comprises a pharmaceutically acceptable excipient.

10. The pharmaceutical formulation according to claim 9, wherein the pharmaceutical formulation is in a form selected from the group consisting of tablets, capsules, caplets, pills, beads, granules, particles, powders, gels, creams, solutions, suspensions, emulsions, and nanoparticulate formulations.

11. The pharmaceutical formulation according to claim 9, wherein the pharmaceutical formulation is:

(i) an oral or intravenous formulation, (ii) in the form of a lyophilized powder, or (iii) in the form of a sterile aqueous solution.

12. A method of treating a condition, disorder or disease in a subject in need thereof, comprising administering an effective amount of the compound according to claim 1 or a composition according to claim 9 to the subject, optionally wherein the subject is a human, wherein the condition, disorder or disease is stroke, subarachnoid hemorrhage, cerebral ischemia, cerebral vasospasm, hypoxia, acute CNS injury, spinal cord injury, traumatic brain injury, coronary artery bypass graft, persistent or chronic cough, substance abuse disorder, opiate withdrawal, opiate tolerance, bipolar disorder, suicidal ideation, pain, fibromyalgia, depression, postpartum depression, resting tremor, dementia, epilepsy, seizure disorder, movement disorder, or neurodegenerative disease.

13. The method according to claim 12, wherein the condition, disorder or disease is pain, depression, stroke, or subarachnoid hemorrhage.

14. The method according to claim 12, wherein:

(i) the pain is neuropathic pain, (ii) the pain is chronic pain, (iii) the pain is cancer pain, or (iv) the depression is treatment-resistant depression.

15. The method according to claim 12, wherein:

(i) the neurodegenerative disease is Huntington's disease, Alzheimer's disease, or Parkinson's disease, (ii) the epilepsy is caused by a genetic mutation, (iii) the seizure disorder is infantile spasms, (iv) the dementia is AIDS-induced dementia, or (v) the hypoxia is induced by respiratory insufficiency, prolonged use of ventilator, or both.

16. The method according to claim 12, wherein the hypoxia is induced by respiratory insufficiency, prolonged use of ventilator, or both, and wherein the respiratory insufficiency, prolonged use of ventilator, or both is associated with COVID-19.

17. The method according to claim 12, wherein the compound or composition is administered orally or intravenously.

18. A composition comprising the compound according to claim 5, wherein the compound is in greater than 80%, 85%, 90%, or 95% enantiomeric excess for the R configuration, with respect to the stereocenter labeled by the * sign, as depicted in Formula II.

19. The composition according to claim 18, wherein the compound is in greater than 95% enantiomeric excess for the R configuration, with respect to the stereocenter labeled by the * sign, as depicted in Formula II.

20. A pharmaceutical formulation comprising the composition according to claim 7, wherein the pharmaceutical formulation further comprises a pharmaceutically acceptable excipient.

21. The method of claim 12, wherein the condition, disorder or disease is persistent or chronic cough.

* * * * *